(12) United States Patent
Brodsky et al.

(10) Patent No.: US 11,675,073 B2
(45) Date of Patent: Jun. 13, 2023

(54) MODULAR PORTABLE ULTRASOUND SYSTEMS

(71) Applicant: Teratech Corporation, Burlington, MA (US)

(72) Inventors: Michael Brodsky, Brookline, MA (US); Alice M. Chiang, Wayland, MA (US); David Christopher Maurer, Stoneham, MA (US); William M. Wong, Milton, MA (US)

(73) Assignee: Teratech Corporation, Burlington, MA (US)

( * ) Notice: Subject to any disclaimer, the term of this patent is extended or adjusted under 35 U.S.C. 154(b) by 1177 days.

(21) Appl. No.: 16/197,754

(22) Filed: Nov. 21, 2018

(65) Prior Publication Data

US 2019/0196011 A1 Jun. 27, 2019

Related U.S. Application Data

(63) Continuation of application No. 13/930,808, filed on Jun. 28, 2013, now Pat. No. 10,139,489, which is a
(Continued)

(51) Int. Cl.
*A61B 8/00* (2006.01)
*G01S 15/89* (2006.01)
*G01S 7/52* (2006.01)

(52) U.S. Cl.
CPC .............. *G01S 15/89* (2013.01); *A61B 8/00* (2013.01); *A61B 8/4427* (2013.01); *A61B 8/4438* (2013.01); *A61B 8/58* (2013.01); *G01S 7/5208* (2013.01); *G01S 7/52082* (2013.01); *G01S 15/899* (2013.01); *A61B 8/4472* (2013.01); *A61B 2560/0456* (2013.01)

(58) Field of Classification Search
None
See application file for complete search history.

(56) References Cited

U.S. PATENT DOCUMENTS 4,733,229 A * 3/1988 Whitehead .......... G06F 3/04842
345/20
5,199,299 A 4/1993 Hughes et al.
(Continued)

FOREIGN PATENT DOCUMENTS

EP 1215510 A2 6/2002
JP 2002-000602 A 1/2002
(Continued)

OTHER PUBLICATIONS

European Search Report for EP Application 14195281.2 dated Mar. 27, 2015, pp. 1-9.
(Continued)

*Primary Examiner* — Patricia J Park
(74) *Attorney, Agent, or Firm* — McCarter & English, LLP

(57) ABSTRACT

The present invention relates to a lightweight, high resolution portable ultrasound system using components and methods to improve connectivity and ease of use. A preferred embodiment includes an integrated system in which the beamformer control circuitry can be inserted into the host computer as a peripheral or within the processor housing.

55 Claims, 53 Drawing Sheets

Related U.S. Application Data continuation of application No. 10/997,062, filed on Nov. 24, 2004, now abandoned.

(60) Provisional application No. 60/525,208, filed on Nov. 26, 2003.

(56) References Cited

U.S. PATENT DOCUMENTS

| | | | |
|---|---|---|---|
| 5,205,175 A | 4/1993 | Garza et al. | |
| 5,251,631 A | 10/1993 | Tsuchiko et al. | |
| 5,310,352 A | 5/1994 | Mroczkowski et al. | |
| 5,318,027 A | 6/1994 | Fukui | |
| 5,385,490 A | 1/1995 | Demeter et al. | |
| 5,417,578 A | 5/1995 | Mroczkowski et al. | |
| 5,460,595 A | 10/1995 | Hall et al. | |
| 5,487,386 A | 1/1996 | Wakabayashi et al. | |
| 5,497,661 A | 3/1996 | Stripf et al. | |
| 5,505,203 A | 4/1996 | Deitrich et al. | |
| 5,558,638 A | 9/1996 | Evers et al. | |
| 5,564,935 A | 10/1996 | Yagi et al. | |
| 5,615,678 A | 4/1997 | Kirkham et al. | |
| 5,617,864 A | 4/1997 | Stouffer et al. | |
| 5,617,866 A | 4/1997 | Marian, Jr. | |
| 5,630,419 A | 5/1997 | Ranalletta | |
| 5,656,124 A | 8/1997 | Krayenhagen et al. | |
| 5,678,551 A | 10/1997 | Stevens | |
| 5,820,549 A | 10/1998 | Marian, Jr. | |
| 5,865,650 A | 2/1999 | Marian, Jr. et al. | |
| 5,880,936 A | 3/1999 | Anderson | |
| 5,882,310 A | 3/1999 | Marian, Jr. | |
| 5,913,688 A | 6/1999 | Marian, Jr. | |
| 5,924,988 A | 7/1999 | Burris et al. | |
| 5,957,727 A | 9/1999 | Page, Jr. | |
| 5,997,479 A | 12/1999 | Savord et al. | |
| 6,007,490 A | 12/1999 | Pawluskiewicz | |
| 6,063,035 A | 5/2000 | Sakamoto et al. | |
| 6,106,472 A * | 8/2000 | Chiang | A61B 8/463 600/447 |
| 6,117,084 A | 9/2000 | Green et al. | |
| 6,149,451 A | 11/2000 | Weber | |
| 6,162,093 A | 12/2000 | Sudol et al. | |
| 6,248,073 B1 | 6/2001 | Gilbert et al. | |
| 6,248,101 B1 * | 6/2001 | Whitmore, III | A61B 1/00149 606/1 |
| 6,261,130 B1 | 7/2001 | Huynh et al. | |
| 6,312,381 B1 * | 11/2001 | Knell | A61B 8/488 600/443 |
| 6,338,716 B1 | 1/2002 | Hossack et al. | |
| 6,364,839 B1 | 4/2002 | Little et al. | |
| 6,371,918 B1 | 4/2002 | Bunce | |
| 6,440,076 B1 | 8/2002 | Sudol et al. | |
| 6,447,451 B1 | 9/2002 | Wing et al. | |
| 6,450,958 B1 | 9/2002 | Linkhart et al. | |
| 6,457,898 B1 | 10/2002 | Donovan et al. | |
| 6,468,212 B1 | 10/2002 | Scott et al. | |
| 6,471,651 B1 | 10/2002 | Hwang et al. | |
| 6,500,120 B1 | 12/2002 | Anthony | |
| 6,500,126 B1 * | 12/2002 | Brock-Fisher | G01S 7/52079 600/459 |
| 6,520,912 B1 | 2/2003 | Brooks et al. | |
| 6,524,244 B1 | 2/2003 | Knell et al. | |
| 6,530,887 B1 | 3/2003 | Gilbert et al. | |
| 6,569,101 B2 | 5/2003 | Quistgaard et al. | |
| 6,575,908 B2 | 6/2003 | Barnes et al. | |
| 6,602,194 B2 | 8/2003 | Roundhill et al. | |
| 6,659,955 B1 | 12/2003 | Marian, Jr. | |
| 6,669,633 B2 | 12/2003 | Brodsky et al. | |
| 6,689,055 B1 | 2/2004 | Mullen et al. | |
| 6,716,167 B1 | 4/2004 | Henderson et al. | |
| 6,780,154 B2 | 8/2004 | Hunt et al. | |
| 6,837,853 B2 | 1/2005 | Marian | |
| 6,969,352 B2 | 11/2005 | Chiang et al. | |
| 6,980,419 B2 | 12/2005 | Smith et al. | |
| 7,022,080 B2 | 4/2006 | Marian, Jr. | |
| 7,297,115 B2 | 11/2007 | Bates et al. | |
| 7,352,570 B2 | 4/2008 | Smith et al. | |
| 7,534,211 B2 | 5/2009 | Hwang et al. | |
| 7,591,786 B2 | 9/2009 | Holmberg et al. | |
| 7,849,250 B2 | 12/2010 | Diener et al. | |
| 8,088,071 B2 | 1/2012 | Hwang et al. | |
| 9,402,601 B1 | 8/2016 | Berger et al. | |
| 10,139,489 B2 | 11/2018 | Brodsky et al. | |
| 2002/0032380 A1 | 3/2002 | Acker et al. | |
| 2002/0035328 A1 | 3/2002 | Roundhill et al. | |
| 2002/0067359 A1 | 6/2002 | Brodsky et al. | |
| 2002/0077548 A1 | 6/2002 | Amemiya | |
| 2002/0138002 A1 | 9/2002 | Tarakci et al. | |
| 2002/0173721 A1 | 11/2002 | Grunwald et al. | |
| 2003/0013966 A1 | 1/2003 | Barnes et al. | |
| 2003/0036704 A1 | 2/2003 | Cerofolini | |
| 2003/0073894 A1 | 4/2003 | Chiang et al. | |
| 2003/0097071 A1 | 5/2003 | Halmann et al. | |
| 2003/0120153 A1 | 6/2003 | Erikson | |
| 2003/0195418 A1 | 10/2003 | Barnes et al. | |
| 2004/0002657 A1 * | 1/2004 | Marian | A61B 8/4438 600/459 |
| 2004/0015079 A1 | 1/2004 | Berger et al. | |
| 2004/0152982 A1 | 8/2004 | Hwang et al. | |
| 2004/0179332 A1 | 9/2004 | Smith et al. | |
| 2005/0251035 A1 | 11/2005 | Wong et al. | |

FOREIGN PATENT DOCUMENTS

| | | |
|---|---|---|
| WO | 2001/12068 A1 | 2/2001 |
| WO | 2002/068992 A2 | 9/2002 |

OTHER PUBLICATIONS

European Communication pursuant to Article 94(3) EPC for European Application No. 14195281.2 dated Apr. 16, 2019, pp. 1-5.
Cannon, ITT Industries. DL/DLM/DLD, Zero Insertion Force Connectors. ITT Industries, Inc., 76 pages, (1999).
Dallas Semiconductor, DS2433-Z01 4kbit 1-Wire EEPROM. Data sheet, retrieved from the Internet: www.pdfserv.maximic.com, Mar. 20, 2002, 2 pages.
FujiFilm, V-Universal Stand SonoSite, Inc. Retrieved online at: http://www.sonosite.com/accessories/h-universal-stand. 5 pages, (2013).
Philips, ClearVue 550 Ultrasound System. Retrieved online at: http://www.healthcare.philips.com. 1 page. Retrieved Jan. 22, 2013.
Samsung, MySono U6, General Specification. Retrieved online at: http://www.samsungmedisonusa.com/ultrasound/general-imaging/mysono-u6/. 16 pages, (2012).
European Office Action for Application No. 14195281.2, dated May 30, 2018. 4 pages.

* cited by examiner

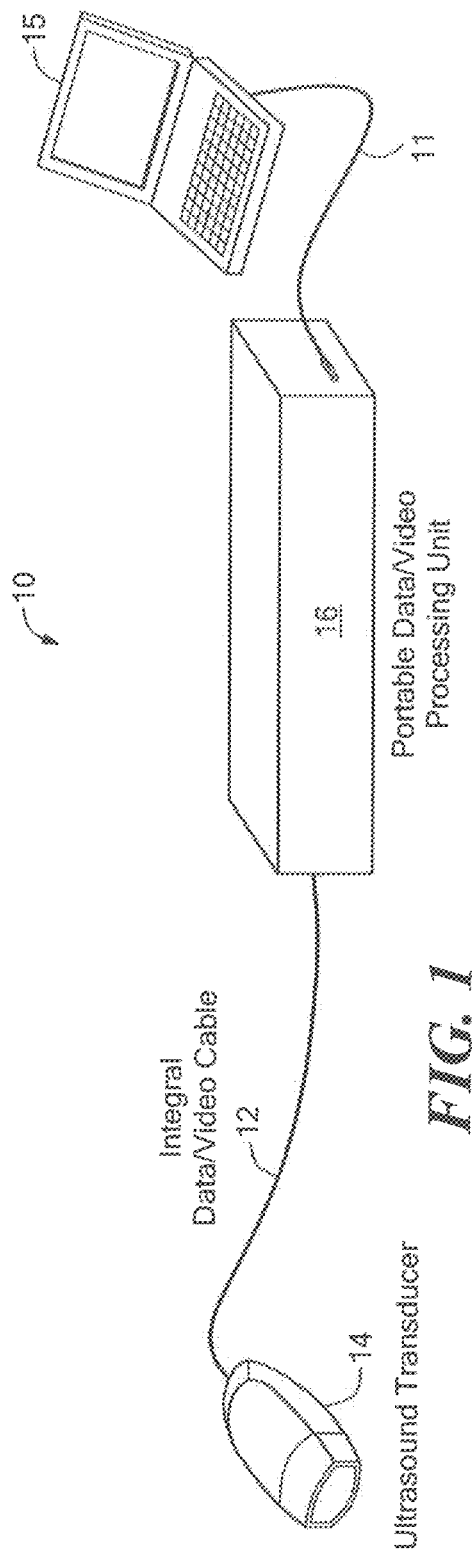
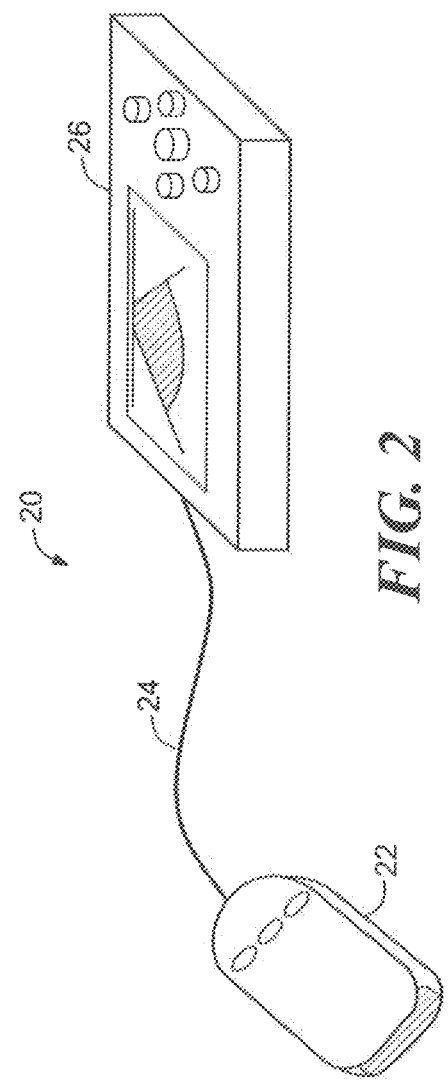

Typical Transducer ID Chip Memory Map:

| Word Address | Bits 31-24 | Bits 23-16 | Bits 15-8 | Bits 7-0 |
|---|---|---|---|---|
| IDENTIFICATION Segment | | | | |
| 0 | Major Revision # | Minor Revision # | Transducer Type ID# | |
| 1 | Transducer Serial # | | | |
| 2 to 7 | Reserved | Reserved | Reserved | Reserved |
| USAGE Segment | | | | |
| 8 | Inauguration System Serial # | | Inauguration Date Code | |
| 9 | Recent System Serial # | | Recent System Date Code | |
| 10 | Previous System Serial # | | Previous System Date Code | |
| 11 | Cumulative Usage Counter | | | |
| 12 to 31 | Reserved | Reserved | Reserved | Reserved |
| FACTORY Segment | | | | |
| 32 to 63 | Per Element Gain Adjustments: 256 Entries of 4 Bits Each. | | | |
| 64 to 95 | Per Element Propagation Delay Adjustments: 256 Entries of 4 Bits | | | |
| USER Segment | | | | |
| 96 to 127 | Reserved For User Defined Calibration data | | | |

*FIG. 15B*

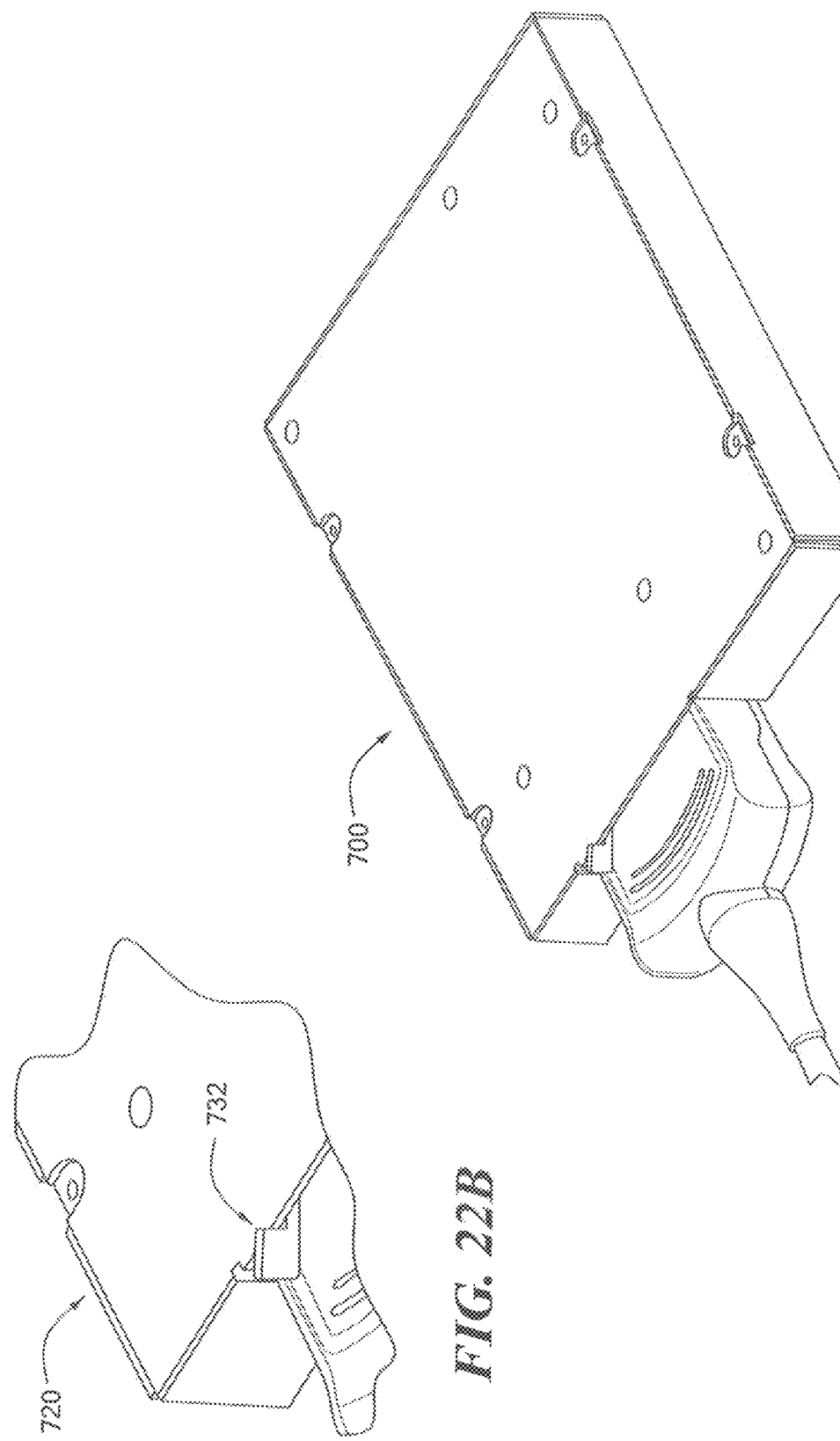

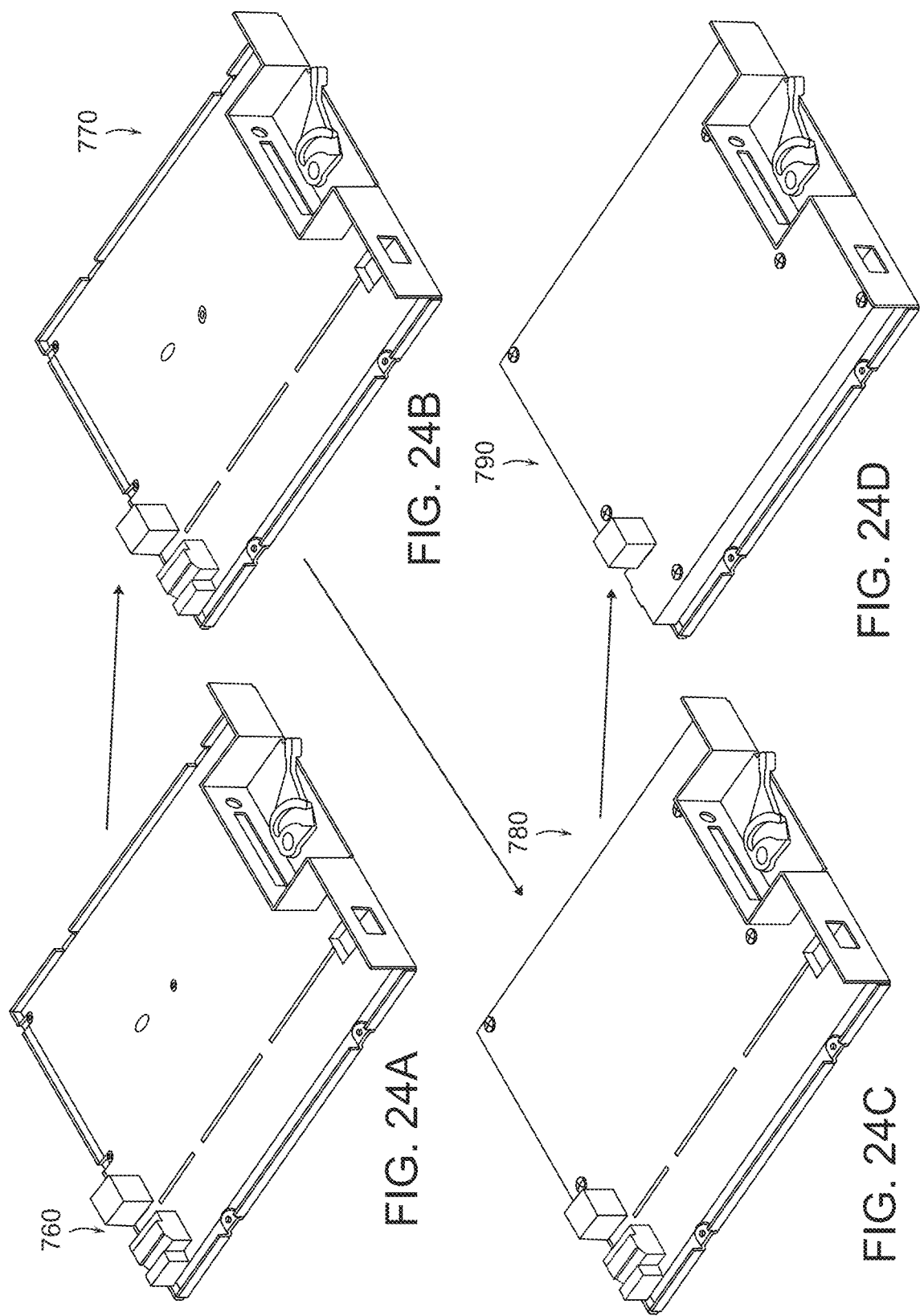

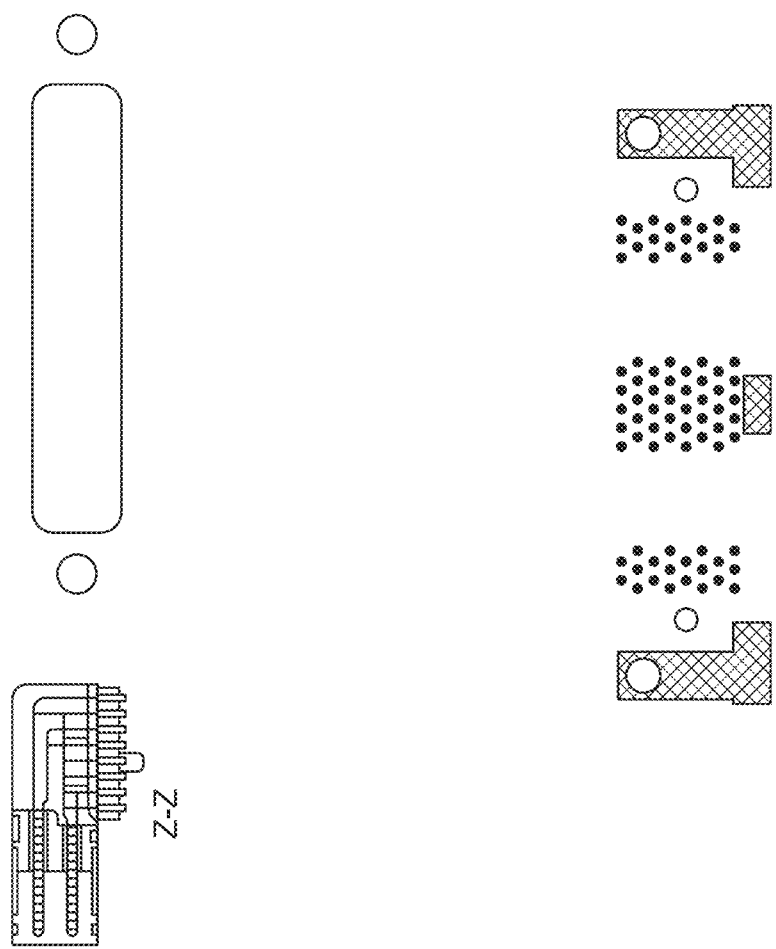
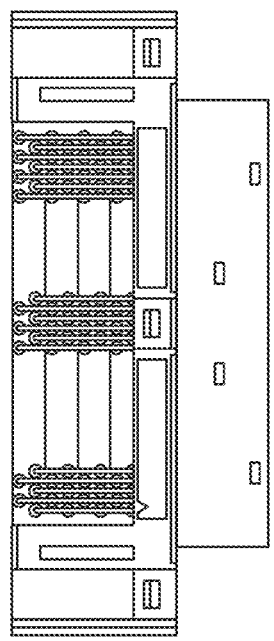
FIG. 27B
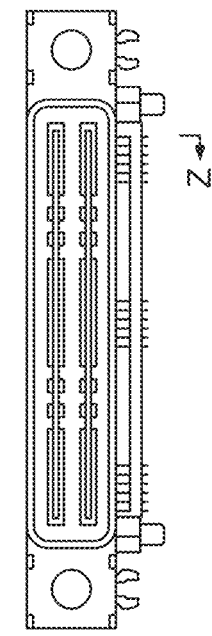
FIG. 27C

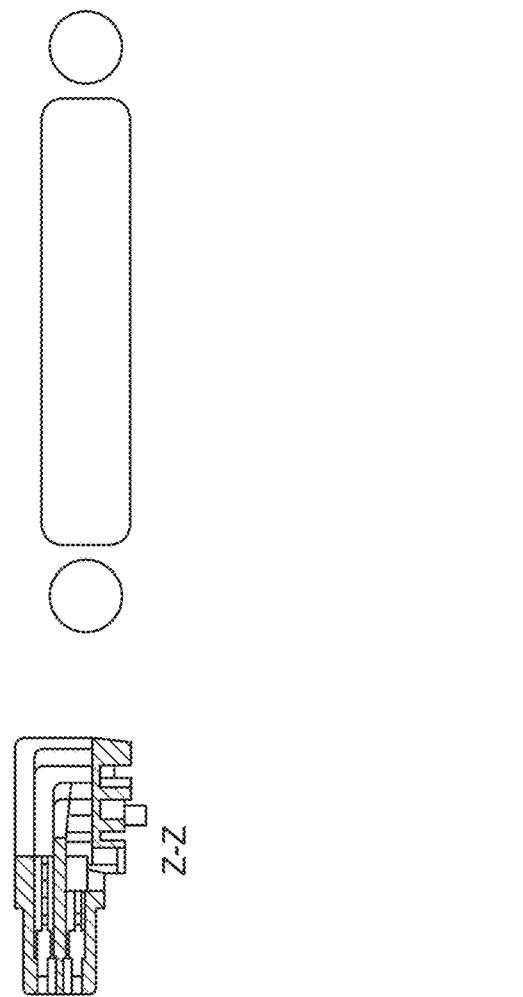
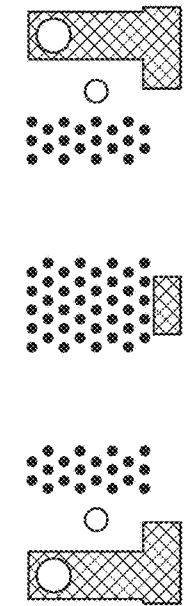
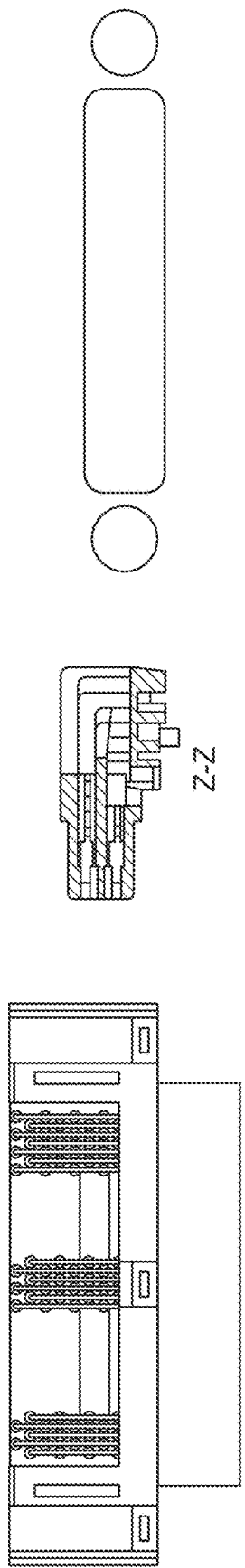
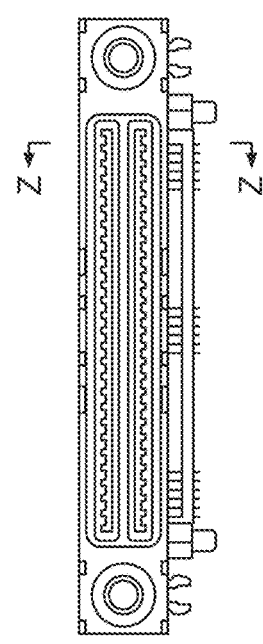
FIG. 28B
FIG. 28C

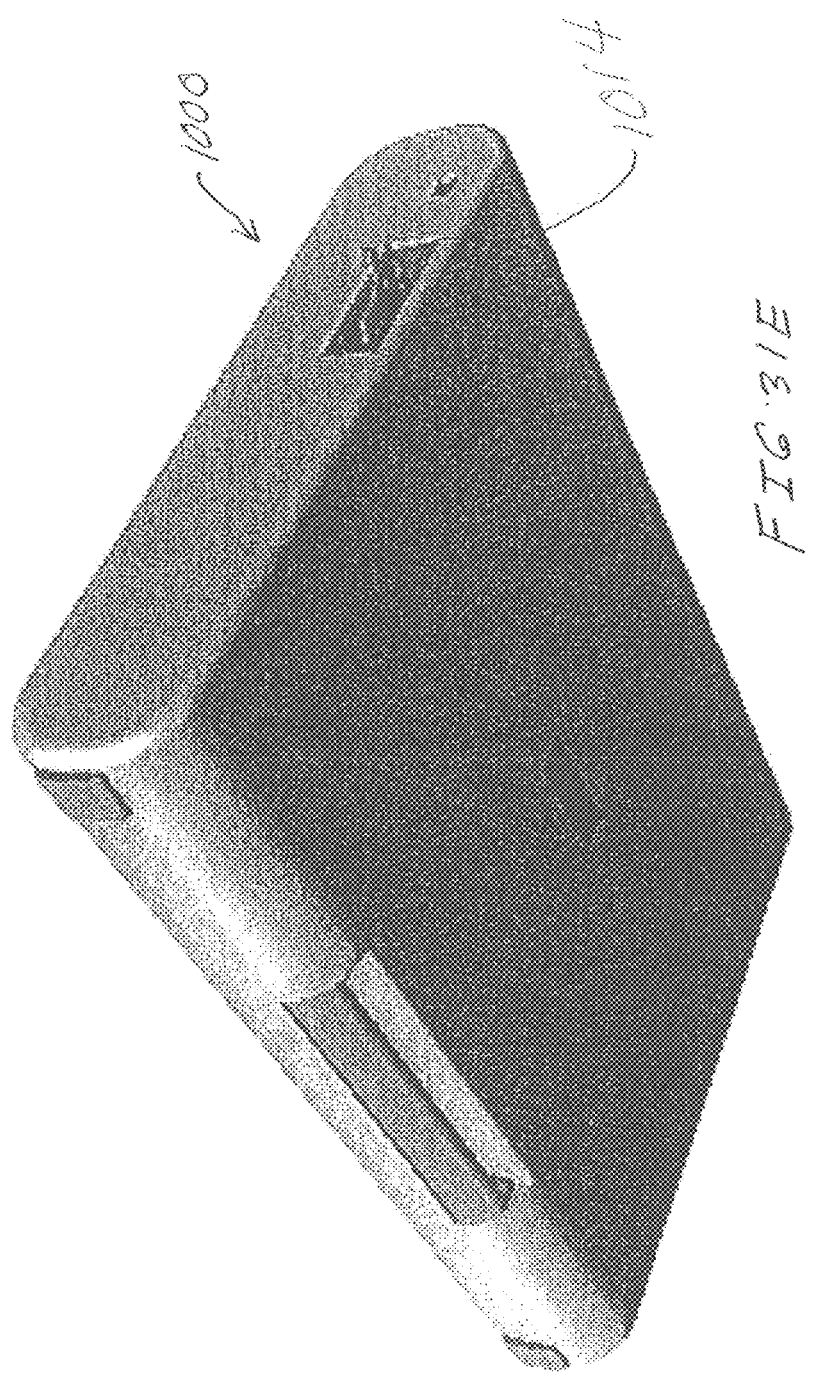

MODULAR PORTABLE ULTRASOUND SYSTEMS

CROSS REFERENCE TO RELATED APPLICATIONS

This application is a continuation of U.S. application Ser. No. 13/930,808, filed Jun. 28, 2013, which is a continuation of U.S. application Ser. No. 10/997,062 filed Nov. 24, 2004, which claims priority to U.S. Provisional Application No. 60/525,208 filed Nov. 26, 2003 entitled: MODULAR PORTABLE ULTRASOUND SYSTEMS.

BACKGROUND OF THE INVENTION

Conventional ultrasound imaging systems typically include a hand-held probe coupled by cables to a large rack-mounted console processing and display unit. The probe typically includes an array of ultrasonic transducers which transmit ultrasonic energy into a region being examined and receive reflected ultrasonic energy returning from the region. The transducers convert the received ultrasonic energy into low-level electrical signals which are transferred over the cable to the processing unit. The processing unit applies appropriate beam forming techniques to combine the signals from the transducers to generate an image of the region of interest.

Typical conventional ultrasound systems include a transducer array each transducer being associated with its own processing circuitry located in the console processing unit. The processing circuitry typically includes driver circuits which, in the transmit mode, send precisely timed drive pulses to the transducer to initiate transmission of the ultrasonic signal. These transmit timing pulses are forwarded from the console processing unit along the cable to the scan head. In the receive mode, beamforming circuits of the processing circuitry introduce the appropriate delay into each low-level electrical signal from the transducers to dynamically focus the signals such that an accurate image can subsequently be generated.

There still remains a need to provide stand-alone processing ultrasound units with the necessary hardware, for example, connectors to enable truly portable ultrasound systems that can function on an independent platform. There is a need for an ultrasound transducer connector assembly with an electrical connector of minimal mechanical complexity, size and cost.

SUMMARY OF THE INVENTION

The system and method of the present invention includes a hand held transducer probe that is connected by wire or wireless connection to a lightweight processing unit including a housing and internal circuitry for processing signals received from the probe. In a preferred embodiment the processing unit housing includes a display and manual and/or virtual controls that can control the display and processor operation, and a battery providing power to the processor housing and the transducer array. A preferred embodiment includes a console of a cart system to provide control features of the modular system.

In a preferred embodiment of the invention, the processor housing includes a transmit/receive (T/R) chip that communicates with the transducer array. A system controller communicates with the T/R chip, a local memory, a preamplifier/TGC chip, a charge domain beamformer circuit and a standard high speed communication interface such as IEEE 1394 USB connection to a system processor.

A preferred embodiment of the invention includes a connector system to secure the cable from the transducer probe to the processor housing. The connector system preferably uses a smaller lightweight connector than prior art systems yet meeting the standard shielding and mechanical strength and integrity requirements for medical ultrasound imaging systems. A preferred embodiment of the invention includes a circuit that identifies the type of transducer array that has been connected to the housing. The circuit can be a single integrated circuit contained in the housing connector module that communicates with the processor and can include a memory storing calibration data for each probe. The display screen will display probe type information for the user. The connector system can include a connector actuator or lock that can be manually actuated by the user to secure the male and female connector elements. In a preferred embodiment a lever is rotated from a first position to a second position such that a cam element attached to the lever mates with a catch element on the cable connector element attached to the probe cable. The lever pulls the connector in and also operates to push the connector element out when actuated in the reverse direction thereby reducing the strain often caused by the user in pulling the cable connector element out of the housing connector element.

In accordance with a preferred embodiment, the method for performing an ultrasound scan on a region of interest of a patient includes connecting a probe to a portable processing unit with a connector system, locking the connector in place, employing the onboard identification circuit to identify the probe and display probe information on the display prior to the scan, entering patient information and performing the scan. Another preferred embodiment of the invention includes a cart system in which the processor housing and display can be connected or docked with a mobile station or cart having a control panel and a port assembly for receiving one or more transducer probes.

The foregoing and other features and advantages of the system and method for ultrasound imaging will be apparent from the following more particular description of preferred embodiments of the system and method as illustrated in the accompanying drawings in which like reference characters refer to the same parts throughout the different views.

BRIEF DESCRIPTION OF THE DRAWINGS

FIG. 1 illustrates a portable ultrasound imaging system including a hand-held probe in accordance with a preferred embodiment of the present invention.

FIG. 2 illustrates a modular portable system having a hand-held ultrasound transducer connected to a processing and display unit in accordance with the present invention.

FIG. 15B illustrates in tabular from characteristics of the ID chip system.

FIGS. 22A and 22B illustrate views of an ultrasound transducer connector assembly inserted into an ultrasound processing unit having a lever to secure the connector assembly in accordance with a preferred embodiment of the present invention.

FIGS. 24A-24D illustrate different views of the ultrasound processing unit showing the ultrasound transducer connector assembly in accordance with a preferred embodiment of the present invention.

FIGS. 27A, 27B, and 27C illustrate views of an ultrasound transducer connector in accordance with a preferred embodiment of the present invention.

FIGS. 28A-28C illustrate views of an ultrasound transducer connector that mates with the connector of FIGS. 27A-27C in accordance with a preferred embodiment of the present invention.

FIGS. 31A-31F illustrate preferred embodiments of a modular ultrasound imaging system in accordance with the invention.

Figure 3:
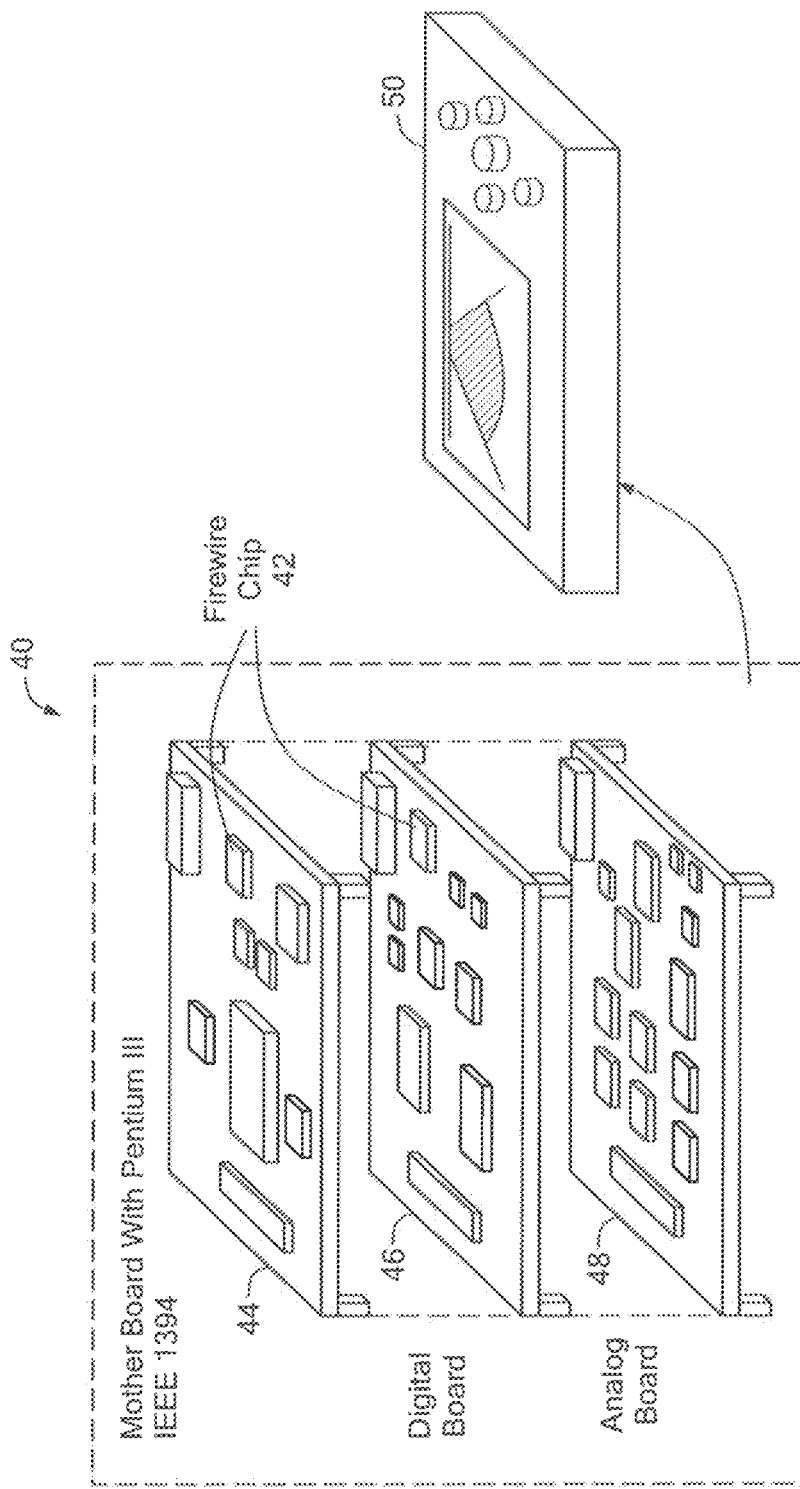
FIG. 3 illustrates a single board computer and beamformer circuits that form the processing unit in accordance with a preferred embodiment of the present invention.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Preferred embodiments of the present invention include modular, portable ultrasound 5 systems that can be used as a stand-alone system. The preferred embodiments integrate the display with the processing unit which is then connected to different ultrasound transducer probes. Preferred embodiments as described in U.S. patent application Ser. No. 10/386,360, filed on Mar. 11, 2003, the entire teachings of which are incorporated herein by reference, include a display integrated on the ultrasound transducer. The operator can easily view the image and operate the probe or scan head, as well as perform operations in the same local area with the other hand. The data/video processing unit is also compact and portable, and may be placed close to the operator or alternatively at a remote location. Optionally, in another embodiment, a display is also integrated into the data/video processing unit. The processing unit also provides an external monitor port for use with traditional display monitors.

FIG. 1 illustrates a preferred embodiment of a portable ultrasound imaging system 10 including a hand-held ultrasound transducer with integrated display and a portable processing unit. The ultrasound transducer 14 comprises any of the standard ultrasound transducer arrays. The interface 12 delivers signals from the array 14 to an interface processor housing 16 that can include a system controller and beamformer as described in detail below. A second cable interface 11 can include a Firewire® (IEEE 1394) connection delivering a beamformed representation for further processing to a personal computer 15.

FIG. 2 illustrates a modular portable system having an ultrasound transducer connected to a processing and display unit in accordance with the present invention. In this preferred embodiment, the video and power wires for the display are integrated with the transducer data wires for the transducer to form a single cable assembly 24 that connects the ultrasound transducer to the portable data/video processing unit 26.

Figure 4A:
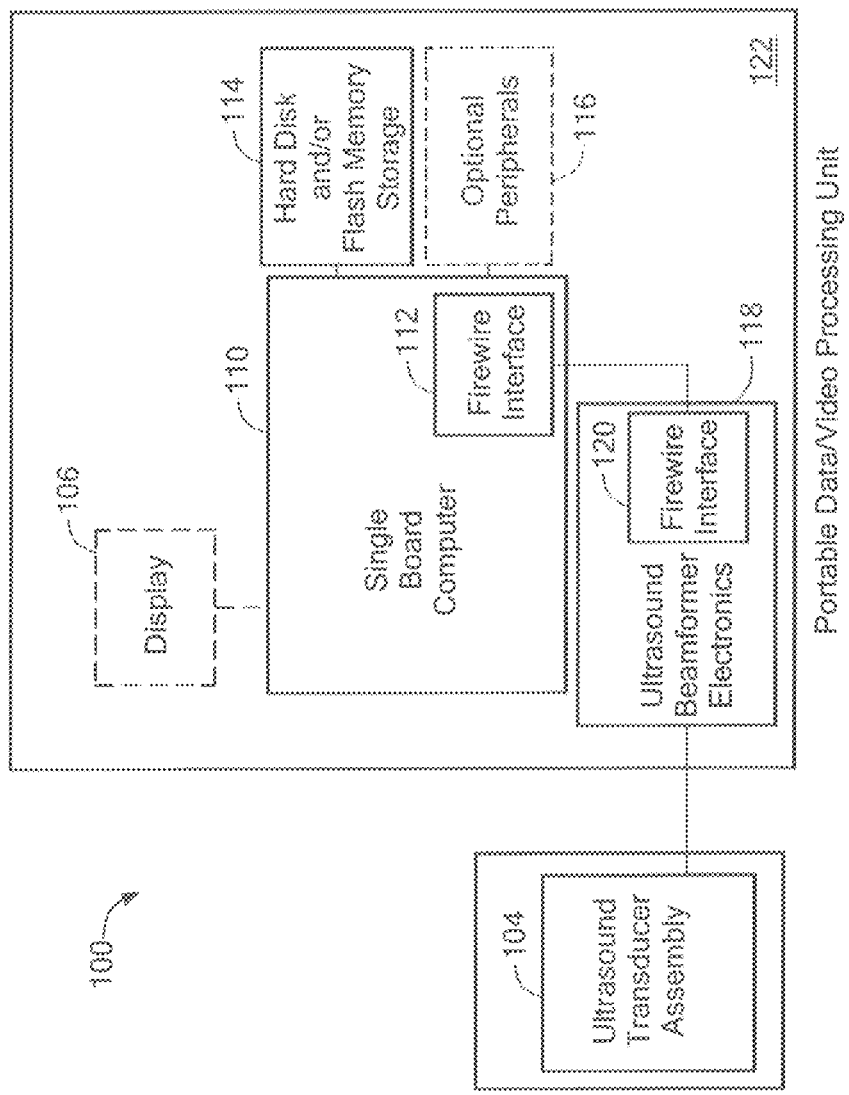
FIGS. 4A and 4B illustrate block diagrams of preferred embodiments of a modular, portable ultrasound system including a hand-held transducer assembly interfacing with a processing unit having the beamformer electronics in accordance with the present invention.

The data/video processing unit 16 is compact and portable. In a preferred embodiment, the beamformer electronics is an integral part of the processing unit and communicating with a single board computer 110 using a Firewire® (IEEE 1394) cable as illustrated in FIG. 4A.

Figure 4B:
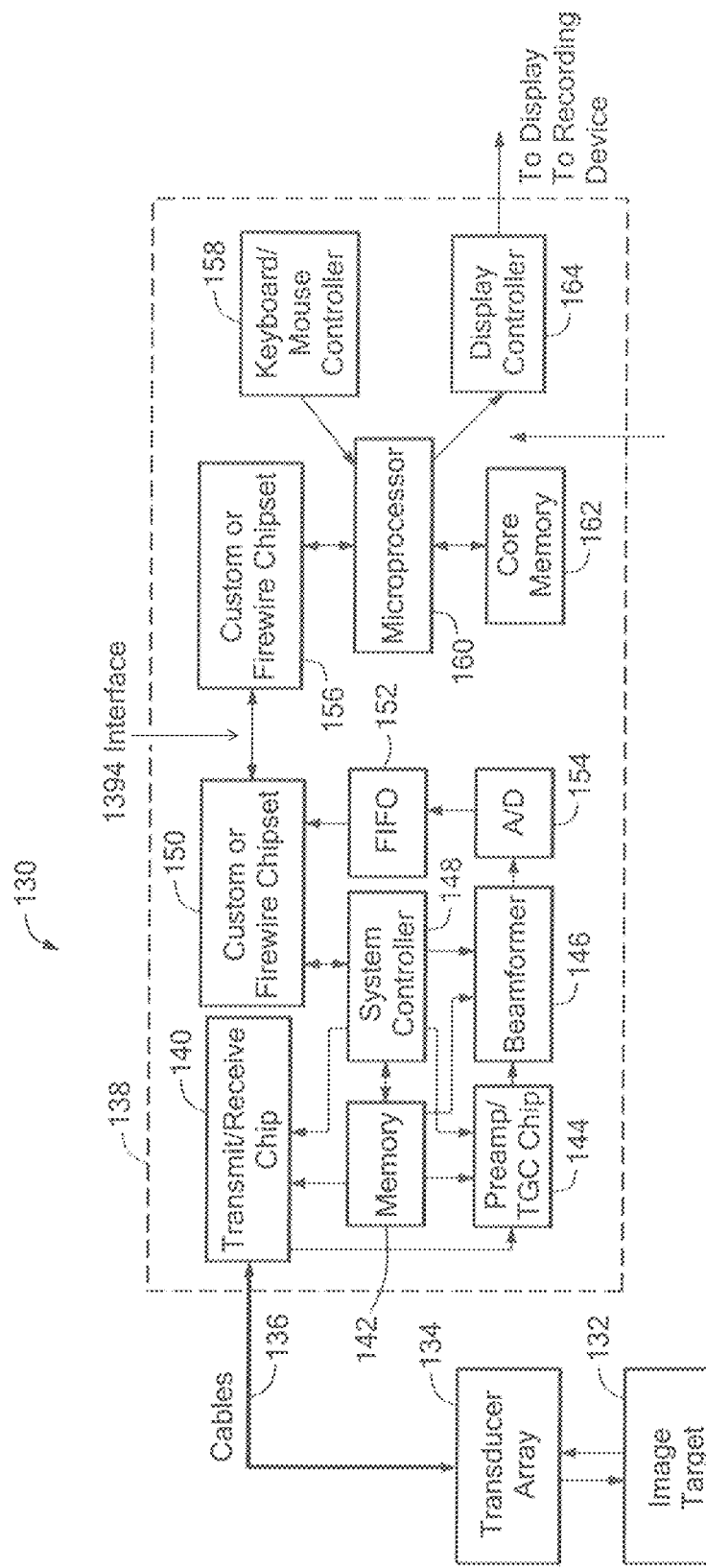

FIG. 3 illustrates the single board computer and beamformer circuits that form the processing unit in accordance with a preferred embodiment of the present invention. FIGS. 4A and 4B illustrate block diagrams of preferred embodiments of a modular, portable ultrasound system including a hand-held transducer assembly interfacing with a processing unit in accordance with the present invention.

In a preferred embodiment, the beamformer electronics is moved inside the processing unit to further reduce the size and weight of the hand-held transducer as illustrated in FIG. 4B. The processing unit 138 can comprise a compact single board 44 computer and the 5 beamformer electronics as illustrated in FIG. 3. The beamformer electronics includes a digital processing printed circuit board and an analog processing printed circuit board 48. The beamforming electronics communicates with the single board computer via a Firewire® (IEEE 1394) chip.

An operating environment for the system includes a processing system with at least one high speed processing unit and a memory system. In accordance with the practices of persons skilled in the art of computer programming, the present invention is described with reference to acts and symbolic representations of operations or instructions that are performed by the processing system, unless indicated otherwise. Such acts and operations or instructions are sometimes referred to as being "computer-executed", or "processing unit executed."

It will be appreciated that the acts and symbolically represented operations or instructions include the manipulation of electrical signals by the processing unit. An electrical system with data bits causes a resulting transformation or reduction of the electrical signal representation, and the maintenance of data bits at memory locations in the memory system to thereby reconfigure or otherwise alter the processing unit's operation, as well as other processing of signals. The memory locations where data bits are maintained are physical locations that have particular electrical, magnetic, optical, or organic properties corresponding to the data bits.

The data bits may also be maintained on a computer readable medium including magnetic disks, optical disks, organic disks, and any other volatile or non-volatile mass storage system readable by the processing unit. The computer readable medium includes cooperating or interconnected computer readable media, which exist exclusively on the processing system or is distributed among multiple interconnected processing systems that may be local or remote to the processing system.

In an embodiment, the compact single board computer has a printed circuit board size of a 5¼ inch disk drive or a 3½ inch disk drive. One embodiment of the present invention uses a NOVA-7800-P800 single board computer in a 5¼ inch form factor, with a low power Mobile Pentium-III® 800 MHz processor, 512 Mbytes of memory, and has on board interface ports for Firewire® (IEEE 1394), local area network (LAN), Audio, integrated device electronics (IDE), personal computer memory card international association (PCMCIA) and Flash memories.

For some dedicated applications, the entire ultrasound system includes the hand-held ultrasound transducer with an integrated display and the portable data/video processing unit. The system can be operated without any controls other than power on/off. For other applications, the system is equipped with an optional operator interface such as buttons and knobs, either on the processing unit, or integrated in the transducer assembly, or both. The processing unit can provide an additional video output to drive an external monitor, or optionally an integrated display on the processing unit itself.

The microprocessor in FIG. 4B provides the functionality for down conversion, scan conversion, M-mode, Doppler processing, color flow imaging, power Doppler, spectral Doppler and post signal processing.

Figure 4C:
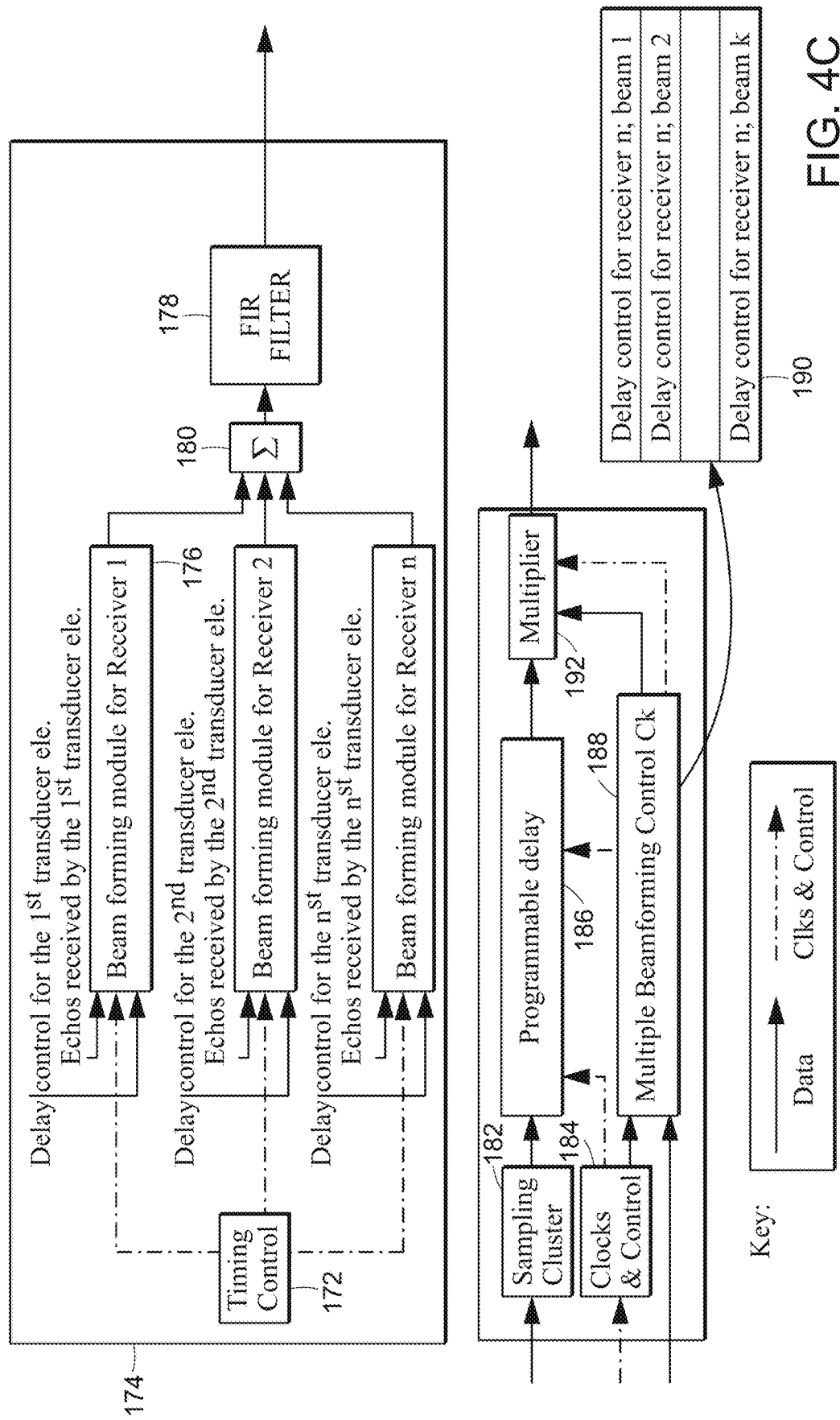
FIG. 4C illustrates a single chip, N-channel, time-multiplexed multiple beamforming processor with on-chip apodization and bandpass filter.

FIG. 4C illustrates a single chip, N-channel time-multiplexed beamforming processor with on-chip apodization and bandpass filter in accordance with a preferred embodiment of the present invention. Beamforming circuits in accordance with preferred embodiments are described in U.S. Pat. No. 6,379,304, issued on Apr. 30, 2002, the entire teachings of which are incorporated herein by reference.

Figure 4D:
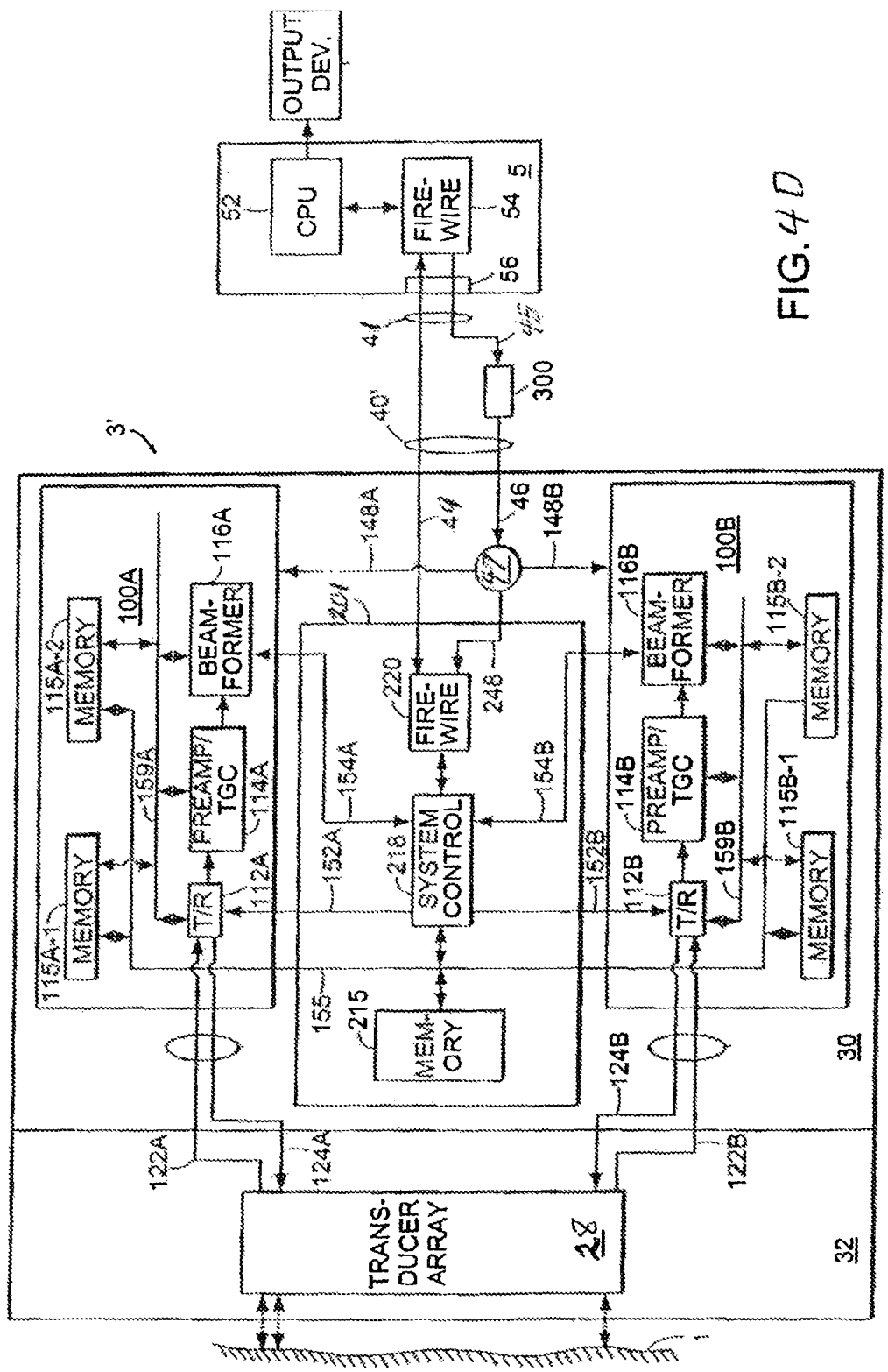
FIG. 4D is a schematic block diagram of a particular embodiment of an integrated probe system.

FIG. 4D is a schematic block diagram of a particular embodiment of an integrated probe system. The host computer 5 can be a commercially available personal computer having a microprocessor CPU 52 and a communications chipset 54. A communications cable 41 is connected through a communications port 56 to the communications chipset 54.

The front-end probe 3' includes a transducer head 32, which can be an off-the-shelf commercial product, and an ergonomic hand-held housing 30. The transducer head 32 houses the transducer array 28. The housing 30 provides a thermally and electrically insulated molded plastic handle that houses the beamforming and control circuitry.

The beam forming circuitry, as shown, can be embodied in a pair of analog circuit boards 100A, 100B. Each analog circuit board 100A, 100B includes a respective transmit/receive chip 112A, 112B; a preamp/TGC chip 114A, 114B; a beamformer chip 116A, 116B; all of which are interconnected with a pair of the memory chips 115A-1, 115B-1, 115A-2, 115B-2 via an operational bus 159A, 159B. In a particular embodiment of the invention, the memory chips are Video Random Access Memory (VRAM) chips and the operational bus is 32 bits wide. Furthermore, preamp/TGC chips 114 and beamformer chips 116 operate on 32 channels simultaneously. The transmit/receive chips 112 include a 64 channel driver and a 64-to-32 demultiplexer.

The control circuitry, as shown in FIG. 4D, is embodied in a digital circuit board 200. The digital circuit board 201 includes a FireWire® chipset 220, a system control chip 218 to control the scan head, and a memory chip 215. In a particular embodiment of the invention, the memory chip 215 is a VRAM chip and the system control chip 218 is interconnected to the various memory chips 115, 215 over a control bus 155, which in this particular application is 16 bits wide.

As illustrated, the system control chip 218 provides scan head control signals to the transmit/receive chips 112A, 112B over respective signal lines 152A, 152B. The transmit/receive chips 112A, 112B energize the transducer array 28 over transmit lines 124A, 124B. Received energy from the transducer array 28 is provided to the transmit/receive chips 112A, 112B over receive lines 122A, 122B. The received signals are provided to the pre-amp/TGC chips 114A, 114B. After being amplified, the signals are provided to the beamformer chips 116A, 116B. Control signals are exchanged between the beamformer and the system controller over signal lines 154A, 154B to adjust the scan beam.

The standard FireWire® cable 41 includes a plurality of FireWire® signal lines 42 and a FireWire® power line 44. In order to provide the necessary voltages, the FireWire® power line 44 is fed to an inline DC-DC converter 300. The DC-DC converter 300 generates the necessary voltages and provides them over a plurality of power lines 46. These new power lines 46 are repackaged with the FireWire® signal lines 49 in a custom cable 40'. In the probe housing 3', the FireWire® signal lines 49 are connected to the FireWire® chipset 220 and the custom power lines 46 are connected to a power distributor 47, which filters and distributes the various voltages over respective internal voltage lines 148A, 148B, 248. In addition, the power distributor 48 may perform additional DC-DC conversions, as described in more detail below.

Figure 5A:
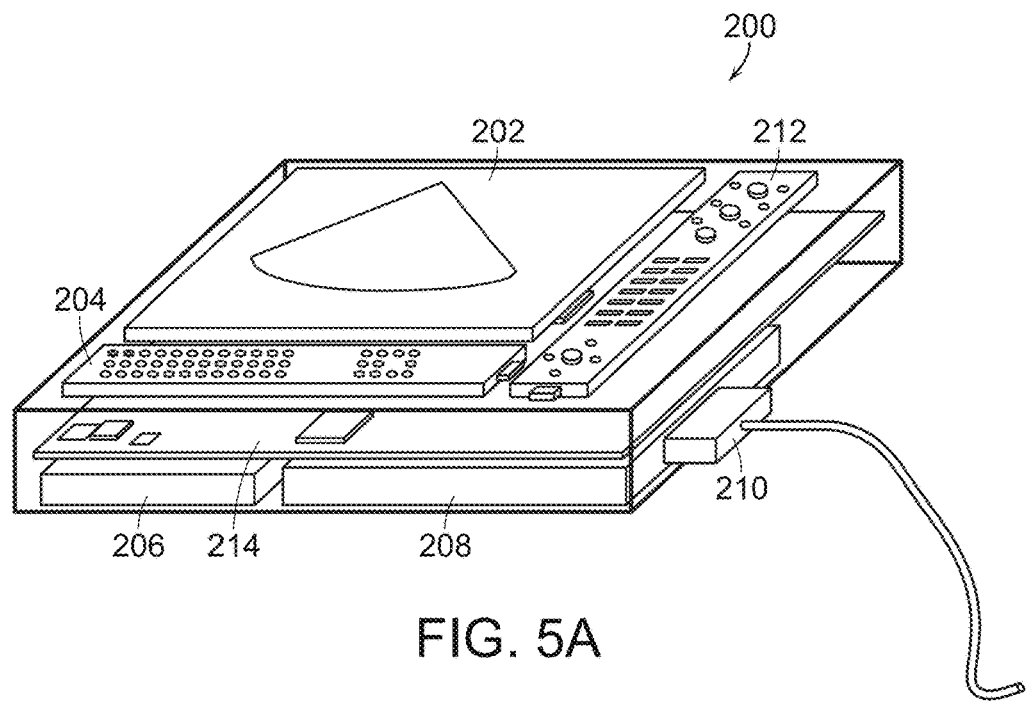
FIG. 5A illustrates a view of a stand alone portable ultrasound processing and display unit in accordance with a preferred embodiment of the present invention.

FIG. 5A illustrates a view of a stand alone portable ultrasound processing and display unit in accordance with a preferred embodiment of the present invention. The processing unit includes a motherboard single board computer.

In a preferred embodiment, the motherboard has the following requirements that are fulfilled by a Pentium® M, 512 MB of RAM or more, 10 GB hard drive, hard drive-free configuration. It includes a flash memory (approximately 1 GB) with a larger RAM (approximately 1 GB). The display that can be integrated into the processing unit may include a 10-inch or 12-inch display, having 1024×768 resolution, 200 Nits brightness as a minimum (after touch screen), 250 desirable, 400:1 contrast ratio, and have a large viewing angle. The ultrasound module can be connected using a 6 pin Firewire® connection. The ultrasound module operates with 12 watt as maximum power.

The graphical user interface includes a touch screen having no drift, and providing for finger operation (no RF pens). The ports for the processing unit include at least 2 universal serial bus (USB) ports to connect an external keyboard, mouse, CDW, and an Ethernet port. The processing unit provides for battery operation, two hours minimum at peak processing power of 7 watt required for ultrasound.

Figure 7:
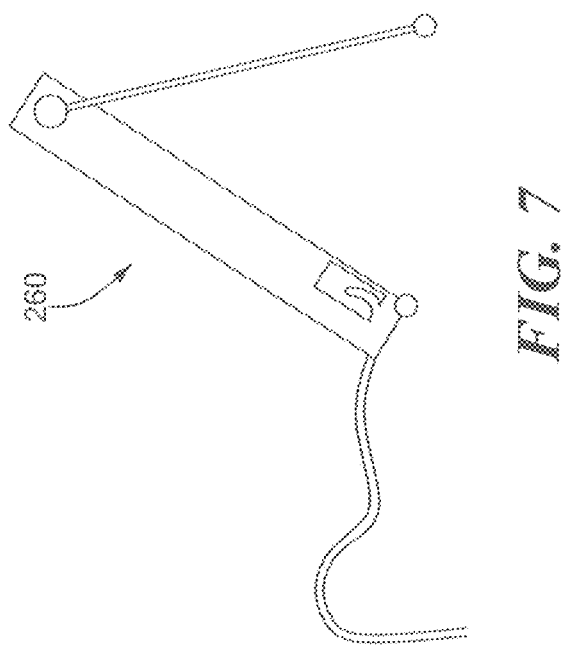
FIG. 7 is a side view of an ultrasound processing and display unit in accordance with a preferred embodiment of the present invention.

A preferred embodiment of the processing unit provides for modularity with a removable processing unit 208 residing inside the ultrasound system. An ultrasound control pad module 212 and custom keyboard 204 can be made removable or configurable. The module 200 itself can also be used as an outside remote control module (USB or wireless) or as an OEM building block. The display module 202 can be made configurable (10-inch or 12-inch), Sun readable or configurable with different platforms. The module has a stand, as illustrated in FIG. 7. There is a protective cover for the display and controls in accordance with a preferred embodiment of the present invention. The unit may be re-used as a stand. A probe holder may be located on the side or on the top of the unit. In alternate preferred embodiments, the probe holder may also be engaged from the side when needed. The probe holder is easy to clean. A handle is provided for ease of carrying the unit. A universal mount that accommodates different holders, for example, tripods, arms, stands, is provided in accordance with a preferred embodiment of the present invention. The ultrasound unit can be docked and is rugged.

Figure 5B:
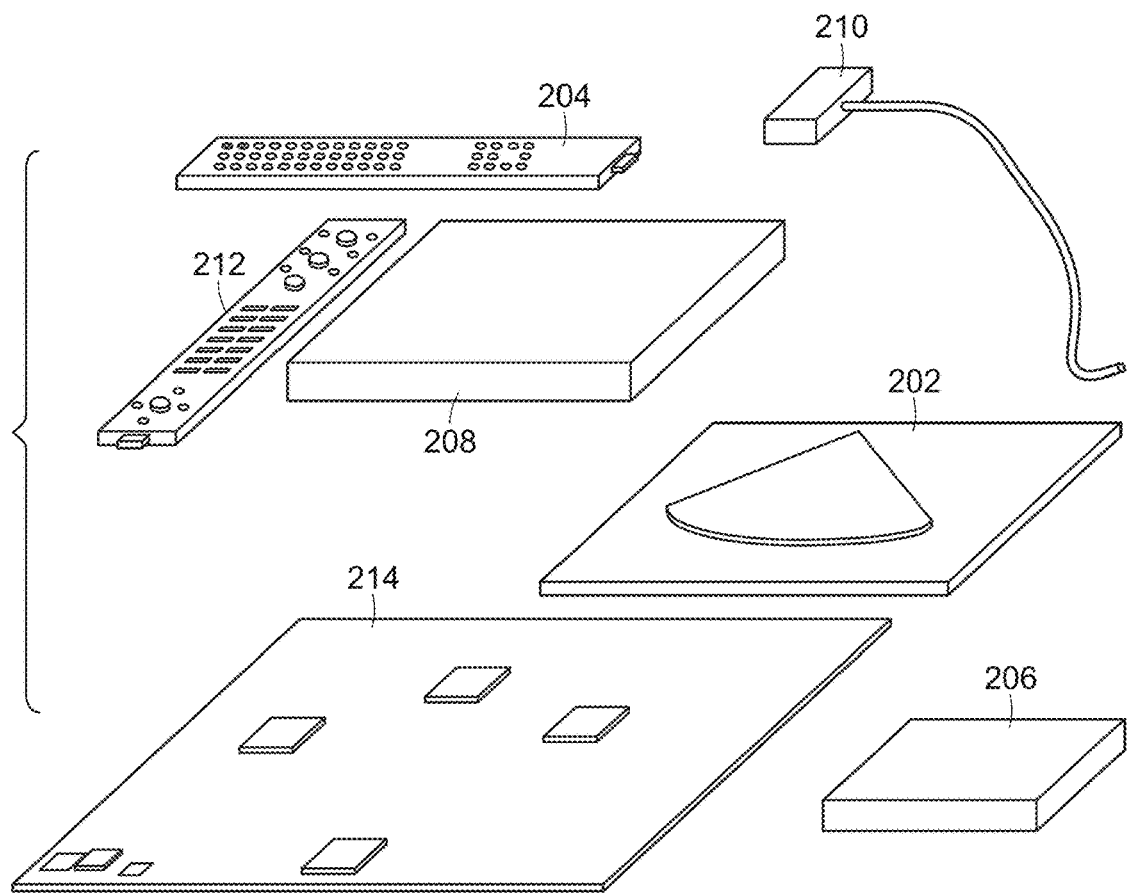
FIG. 5B illustrates an exploded view of the ultrasound processing and display unit shown in FIG. 5A in accordance with a preferred embodiment of the present invention.

FIG. 5B illustrates an exploded view of the ultrasound processing and display unit shown in FIG. 5A in accordance with a preferred embodiment of the present invention. The unit 200 includes the modular display 202, the ultrasound processing unit 208 that includes the beamforming circuitry, a keyboard 204, a control pad module 204, a battery module 206 and the single board computer 214.

Figure 6A:
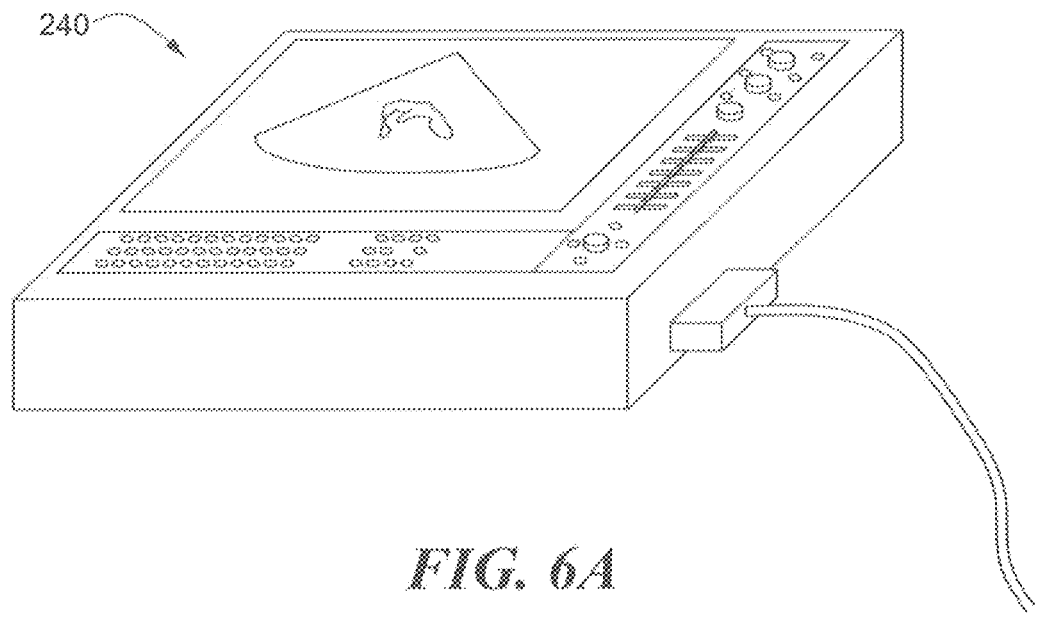
FIGS. 6A and 6B illustrate a 10-inch and 12-inch display, respectively, that can be included in an ultrasound stand-alone unit in accordance with a preferred embodiment of the present invention.
Figure 6B:
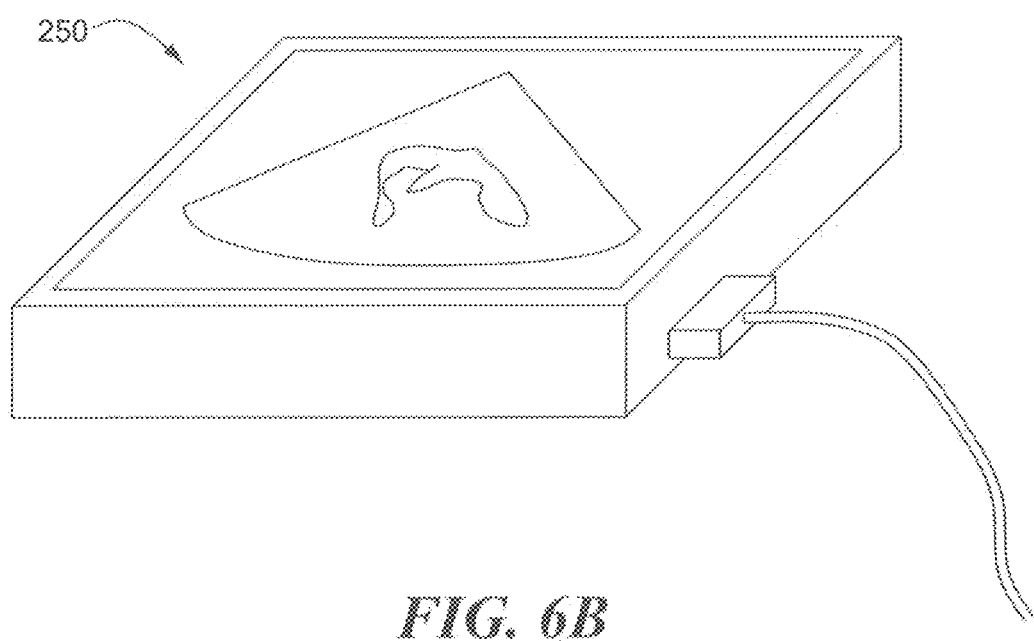

FIGS. 6A and 6B illustrate a 10-inch and 12-inch display, respectively, that can be included in an ultrasound stand-alone unit in accordance with a preferred embodiment of the present invention. As described hereinbefore, the display in accordance with a preferred embodiment of the present invention provides a resolution of 1024×768 and a large viewing angle.

FIG. 7 is a side view of an ultrasound processing and display unit having a stand in accordance with a preferred embodiment of the present invention.

Figure 8A:
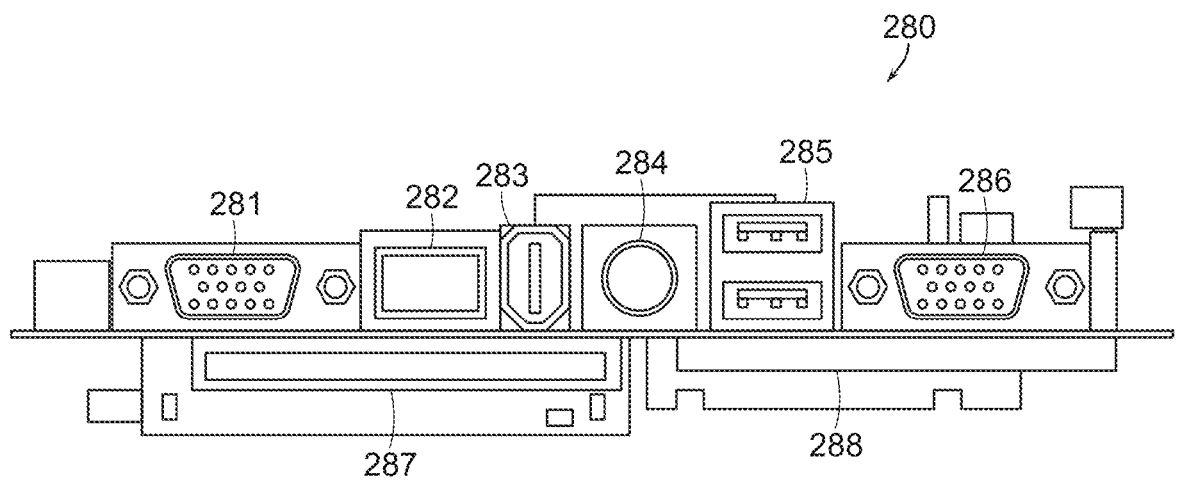
FIGS. 8A-8B illustrate views of a single board computer included in the ultrasound stand alone unit in accordance with a preferred embodiment of the present invention.
Figure 8B:
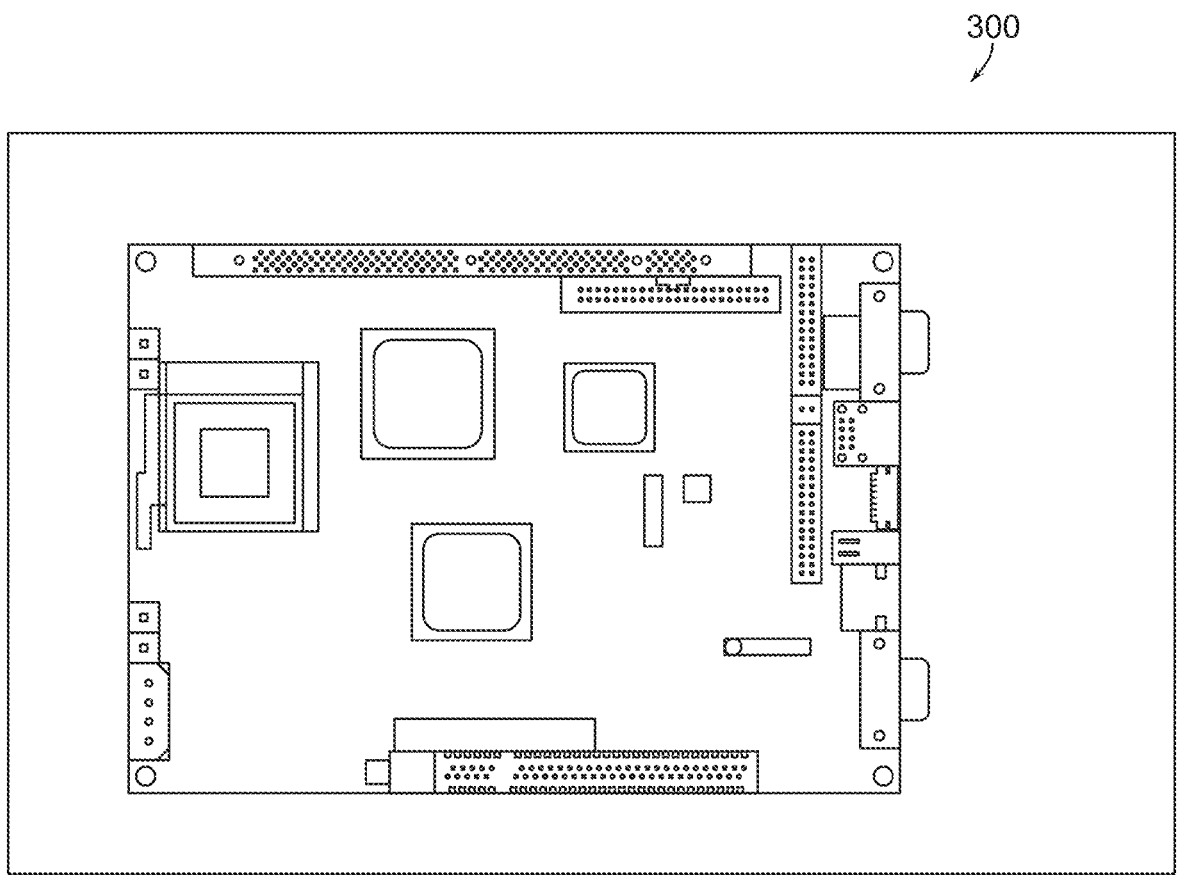
Figure 9:
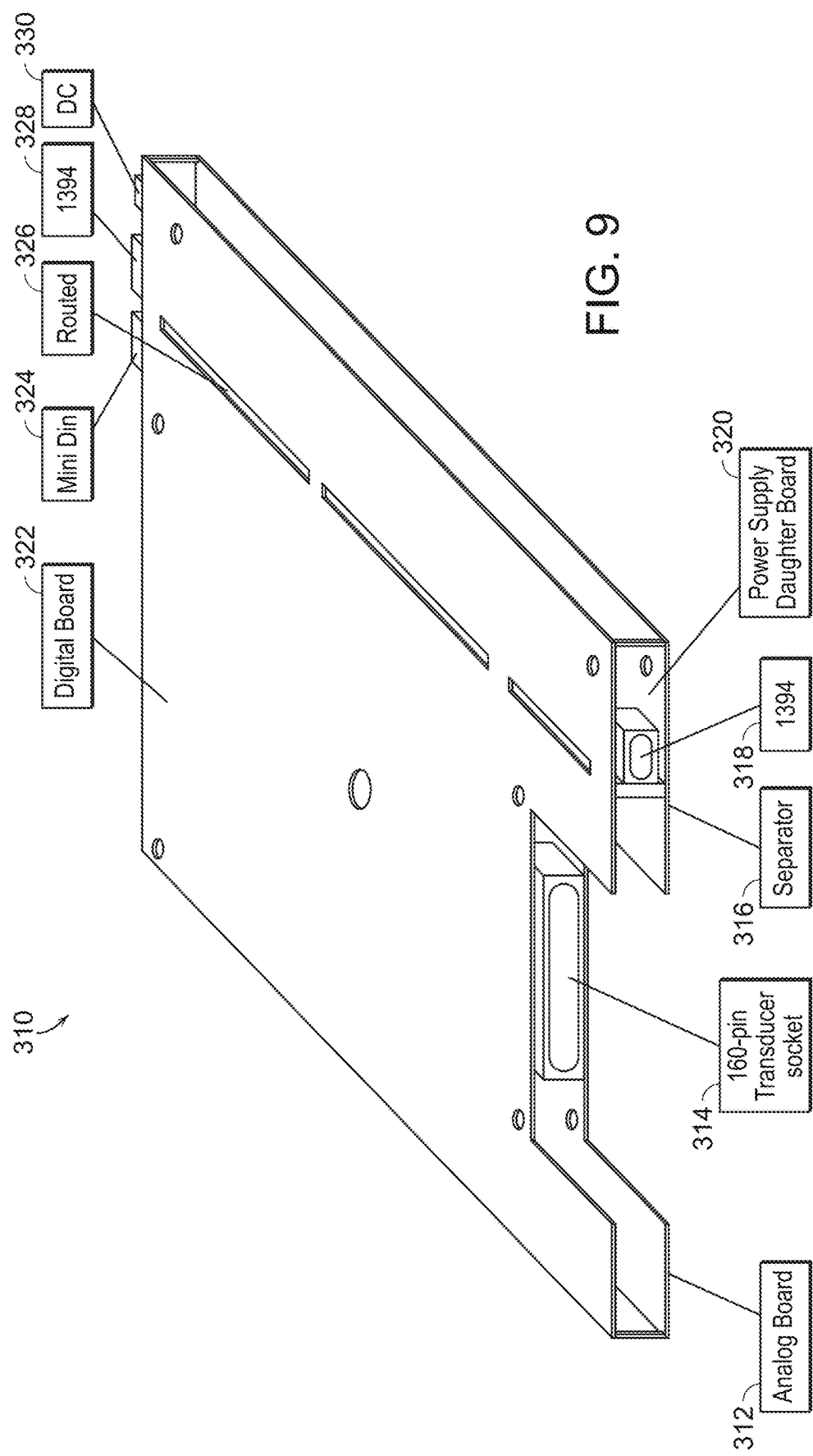
FIG. 9 illustrates a view of the configuration of the computer boards in a stand alone ultrasound unit in accordance with a preferred embodiment of the present invention.

FIGS. 8A-8B illustrates views of a single board computer included in the ultrasound stand alone unit in accordance with a preferred embodiment of the present invention. FIG. 8A illustrates a view of a single board computer 270 used in the ultrasound portable unit. The interface ports of the single board are illustrated in detail in FIG. 8B. The interfaces include video graphics adapter (VGA) 281, a local area network (LAN) interface 282, a IEEE 1394 interface 283 and a PS/2 bus interface 284 which has a microchannel architecture. Further, the interfaces include a universal serial bus (USB) interface 285, a COM1 interface 286 which is a serial communications port, a Personal Computer Memory Card International Association (PCMCIA) interface 297 for PC-cards and a CFII interface 288. FIG. 9 illustrates a view of the configuration 310 of the computer boards in a stand alone ultrasound unit in accordance with a preferred embodiment of the present invention. An analog board 312 is spaced from a digital board 322. A transducer socket 314 having a 160 pin socket is provided. A power supply daughter board 320 is provided and spaced from the analog and digital boards by a separator 316. A plurality of interfaces are also provided, for example, IEEE 1394 interface 318, and a Deutsch Industrie Norm (DIN) connector 324 which is a multipin connector conforming to the specifications of the German National Standards Organization.

FIGS. 10A-10F illustrate views of the ultrasound processing unit configured for different applications such as different processing unit configured in different applications such as different original engineering manufacture (OEM) configurations and stand alone configurations in accordance with a preferred embodiment of the present invention. A preferred embodiment includes the motherboard, display driver and ultrasound interface in the housing with the provisions for plug-in transducer arrays. An alternate embodiment includes stand-alone unit with a plug-in transducer array.

Figure 10A:
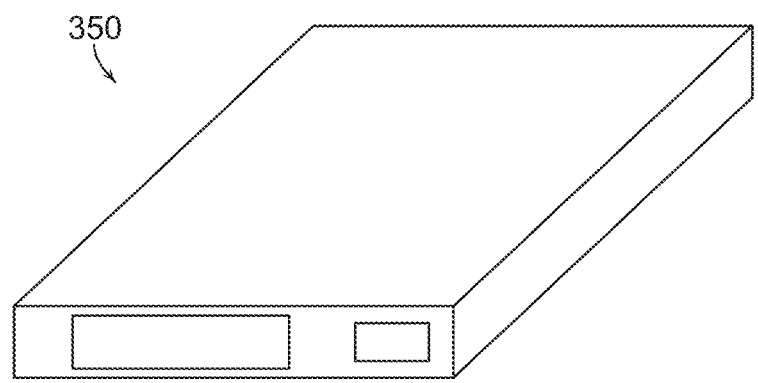
FIGS. 10A-10F illustrate views of the ultrasound processing unit configured for different applications such as different processing unit configured in different applications such as different original engineering manufacture (OEM) configurations and stand alone configurations in accordance with a preferred embodiment of the present invention.
Figure 10B:
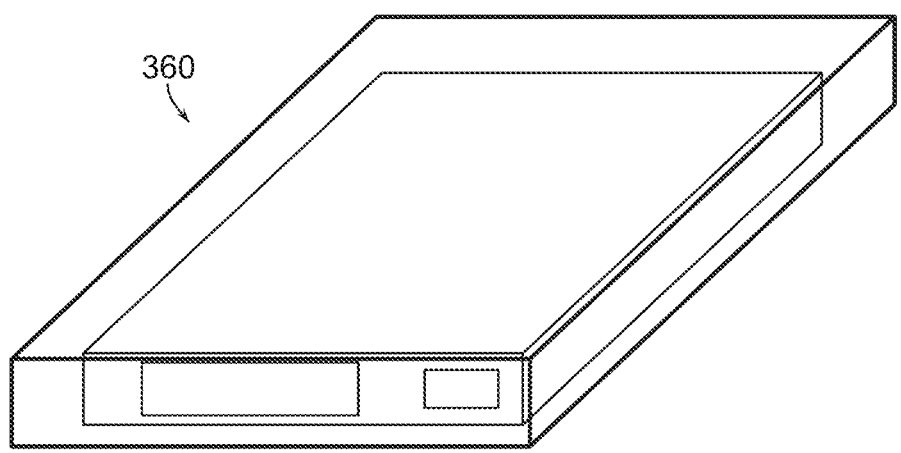
Figure 10C:
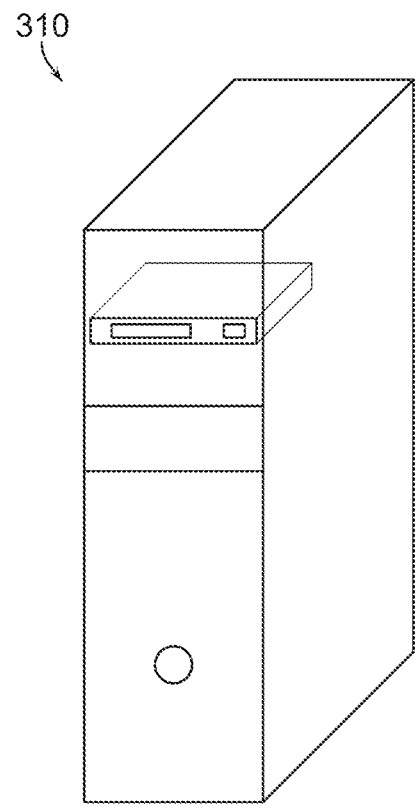
Figure 10D:
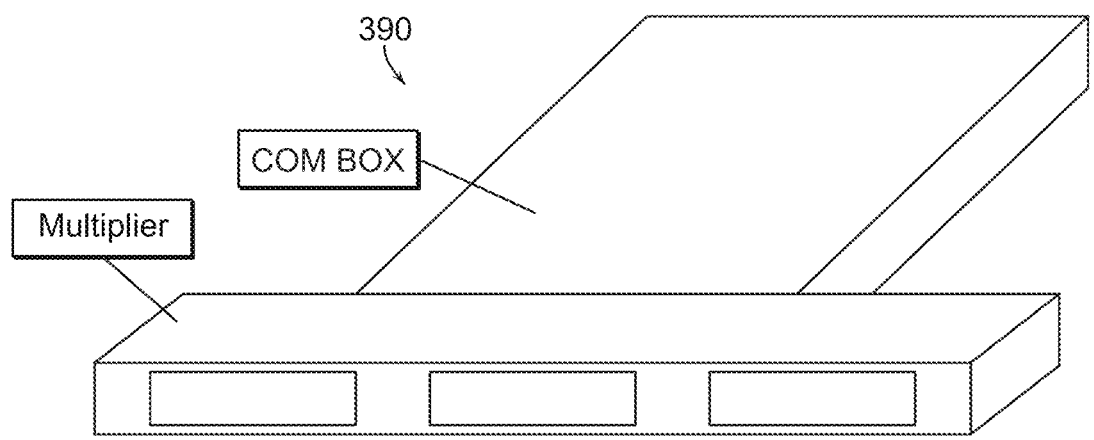
Figure 10E:
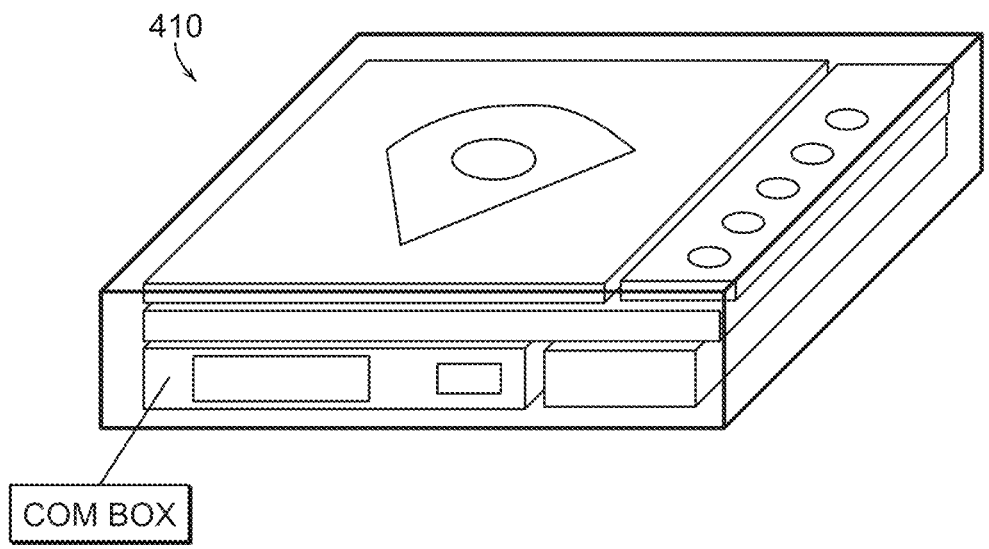
Figure 10F:
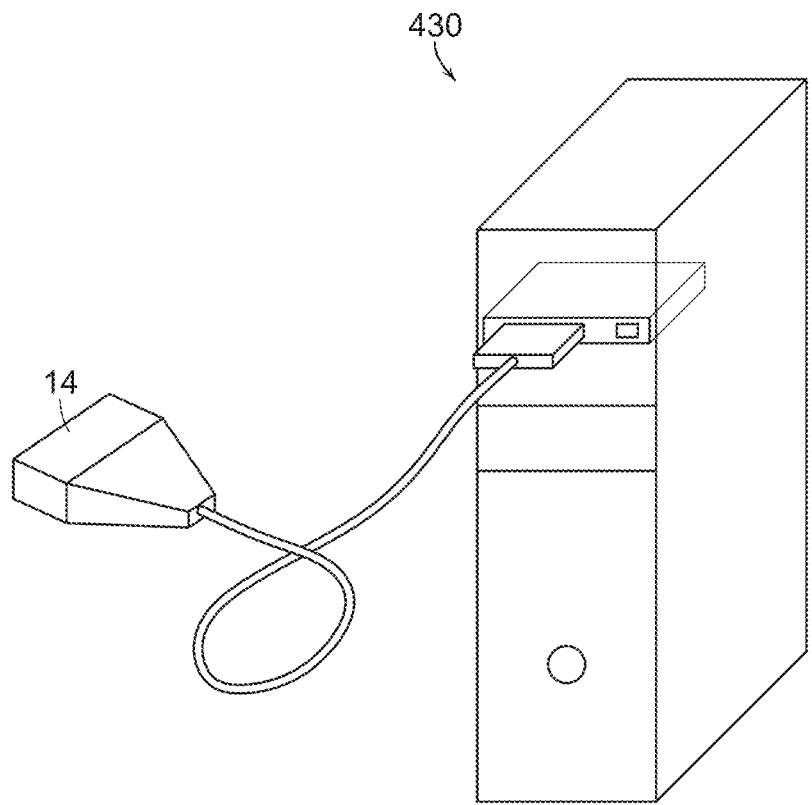

FIG. 10A illustrates an OEM configuration having a basic aluminum box with mounting holes. FIG. 10B illustrates the ultrasound processor inside a housing. FIG. 10C illustrates the ultrasound processing unit inside a PC drive bay. FIG. 10D illustrates an OEM configuration with a multiplexor. FIG. 10E is a view of a stand-alone configuration having an OEM housing, a single board computer, a LCD, and a battery module. FIG. 10F illustrates the processing unit that can be connected in an OEM configuration or be a stand-alone unit.

An interlock is included to sense if a probe is present and to determine the calibration coefficient in accordance with a preferred embodiment of the present invention. A one wire identification (ID) chip for identifying the transducer is included in accordance with a preferred embodiment of the present invention. The computer can be pre-programmed with signal conditioning for each probe in accordance with a preferred embodiment of the present invention. By effectively connecting the probe, the circuit identifies the probe and accesses the pre-programmed conditions for that probe. Calibration coefficients are stored for each probe in the memory of the processing unit. The system can include a multiplexor to provide multiple connection ports that allows for the connection of two or three probes to one system using a multiplexed interface.

Figure 11:
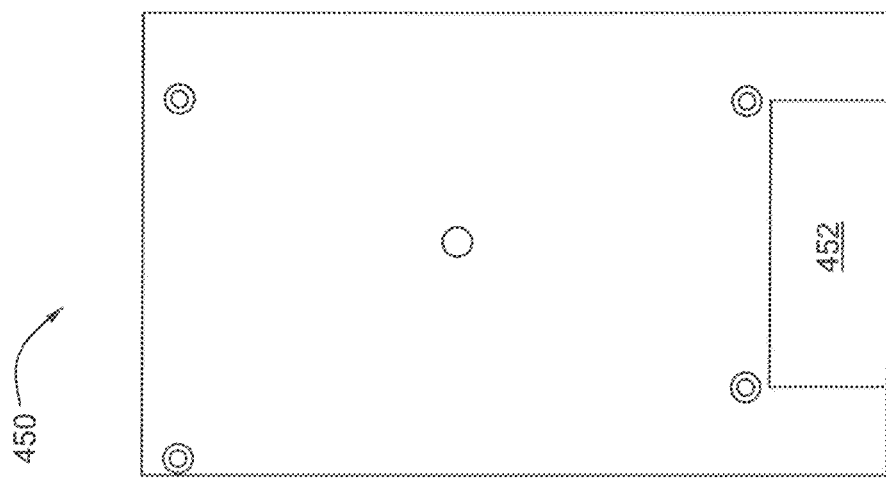
FIG. 11 illustrates a schematic drawing of an analog board included in an ultrasound processing unit in accordance with a preferred embodiment of the present invention.

FIG. 11 illustrates a schematic drawing of an analog board included in an ultrasound processing unit in accordance with a preferred embodiment of the present invention. A transducer connector is accommodated in region 452.

Figure 12:
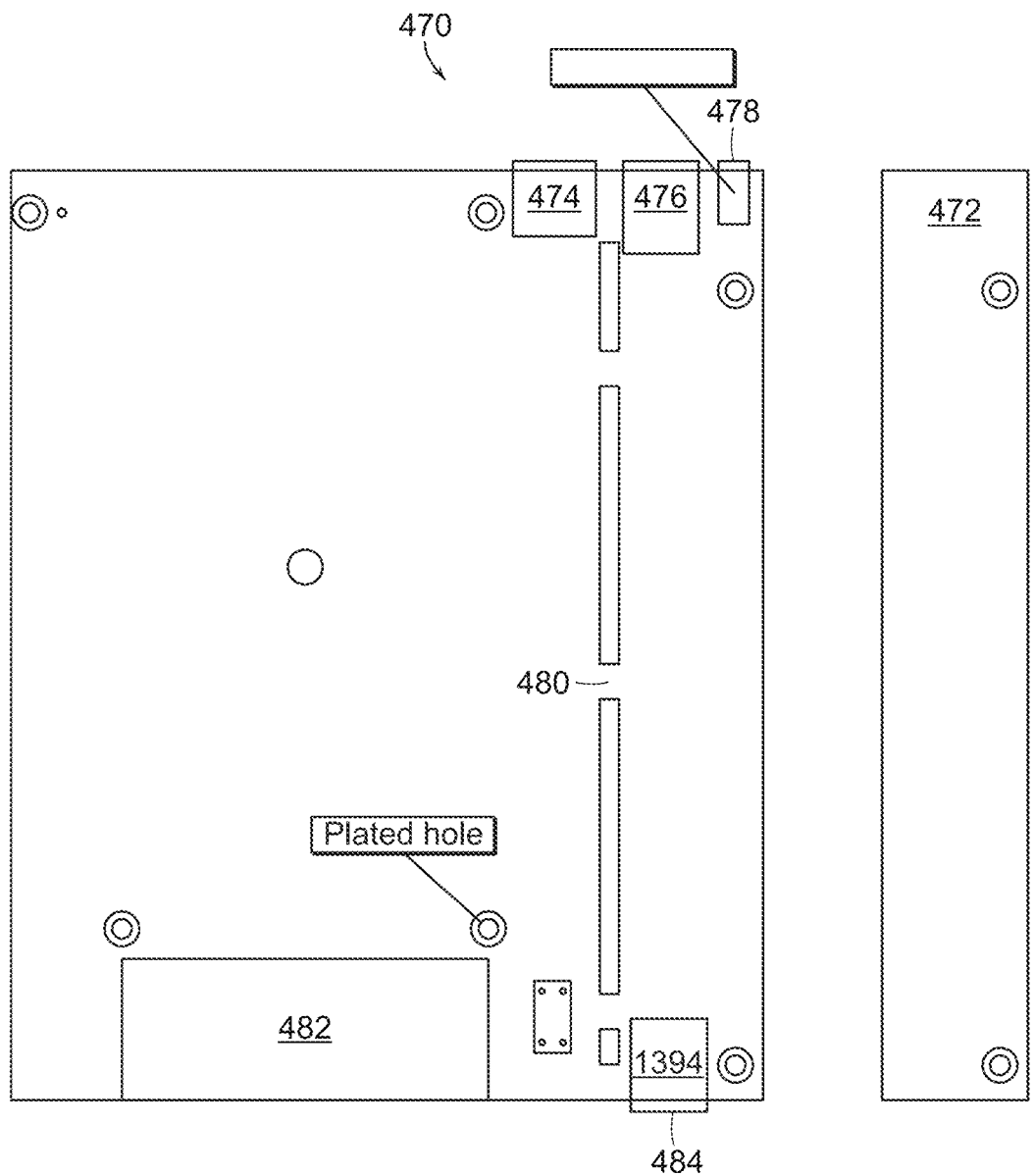
FIG. 12 illustrates a schematic view of a digital board and a power supply daughter board included in an ultrasound processing unit in accordance with a preferred embodiment of the present invention.

FIG. 12 illustrates a schematic view of a digital board 470 and a power supply daughter board 472 included in an ultrasound processing unit in accordance with a preferred embodiment of the present invention. Also provided is a mini-DIN interface 474, and IEEE 1394 interfaces 476, 484.

Figures 13A, 13B:
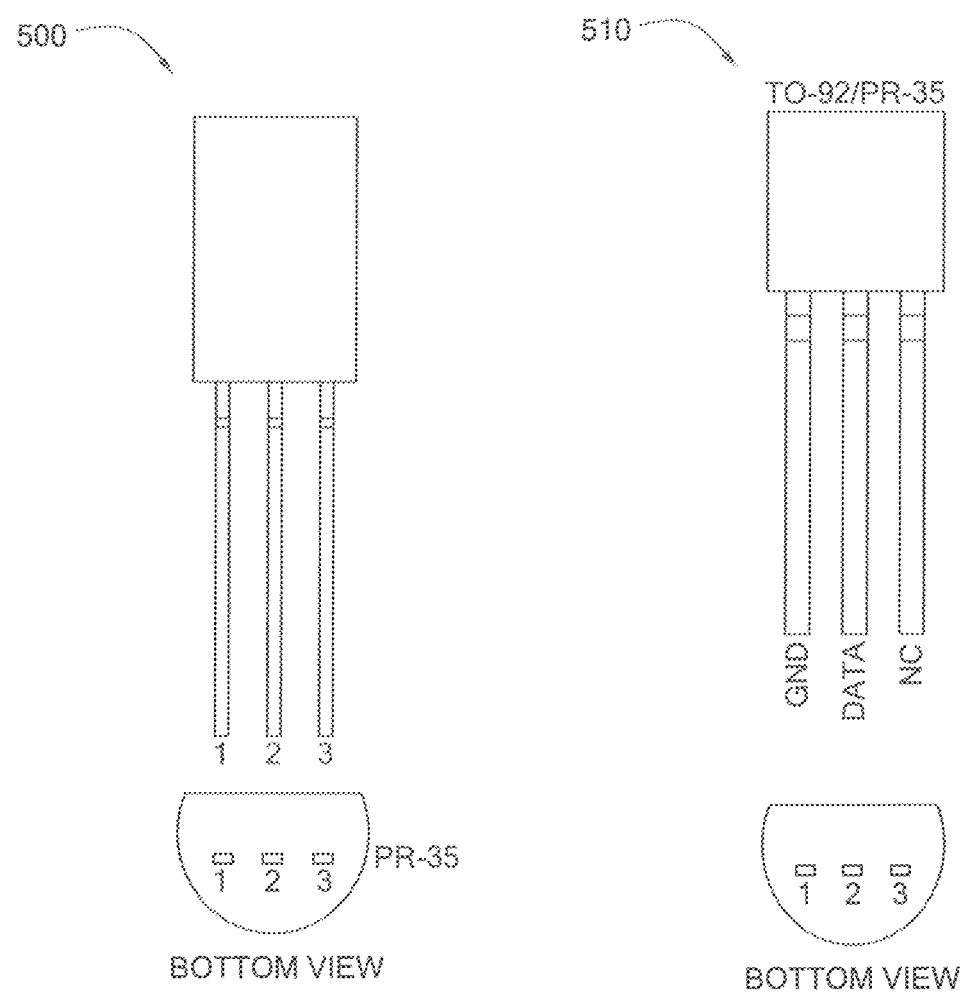
FIGS. 13A-13B illustrate the pin assignment of an electrically erasable programmable read only memory (EE-PROM) and an electrically programmable read only memory integrated circuits, respectively, that can be included in the ultrasound processing unit in accordance with a preferred embodiment of the present invention.

FIGS. 13A-13B illustrate the pin assignment of an electrically erasable programmable read only memory (EEPROM) and an electrically programmable read only memory integrated circuits, respectively, that can be included in the ultrasound processing unit in accordance with a preferred embodiment of the present invention.

FIG. 13A illustrates a 4096 bits, one-wire EEPROM that assures absolute identity as no two parts are alike. It includes a built-in multi-drop controller. The memory is partitioned into sixteen 256-bit pages for packetizing data. This EEPROM identifies and stores relevant information about each ultrasound transducer to which it is associated. It is easily interfaced with using a single port pin of a microcontroller. The 4 Kb, one-wire EEPROM can be, for example, but not limited to a DS2433 circuit provided by Dallas Semiconductor.

FIG. 13B illustrates, for example, a DS2502/5/6 UNW UniqueWare™ add only memory chip provided by Dallas Semiconductor. The EPROM can be a 1024 bits, 16 kbits or 65 kbits memory and can communicate with the economy of one signal plus ground.

Preferred embodiment of the medical ultrasound systems use many transducers depending upon the application. These systems also identify which transducer is attached at any given time in accordance with a preferred embodiment of the present invention.

Figure 14:
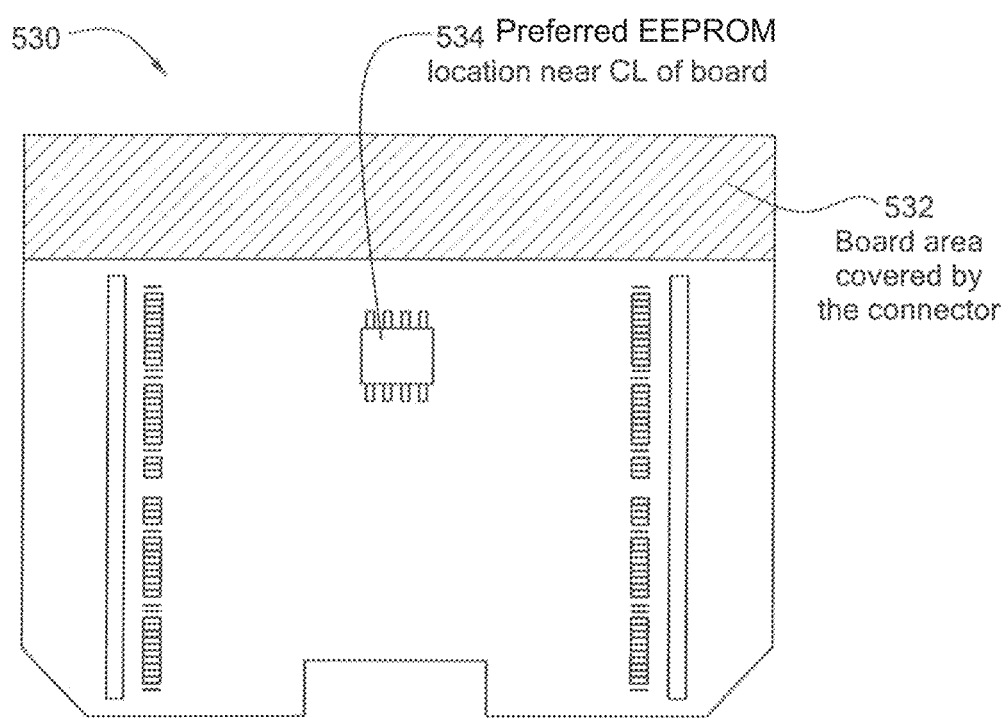
FIG. 14 illustrates a semiconductor one-wire identification integrated circuit chip installed in transducer assemblies in accordance with a preferred embodiment of the present invention.

In addition to identifying the transducer type, preferred embodiments also identify the individual probe of the same type, such that calibration information can be associated with a particular probe. The one-wire ID circuits described with respect to FIGS. 13A and 13B provide identification of each transducer and corresponding calibration information by installing the semiconductor one-wire identification chips in each transducer assembly as shown in FIG. 14. FIG. 14 illustrates a semiconductor one-wire identification integrated circuit chip installed in transducer assemblies in accordance with a preferred embodiment of the present invention.

Figure 15A:
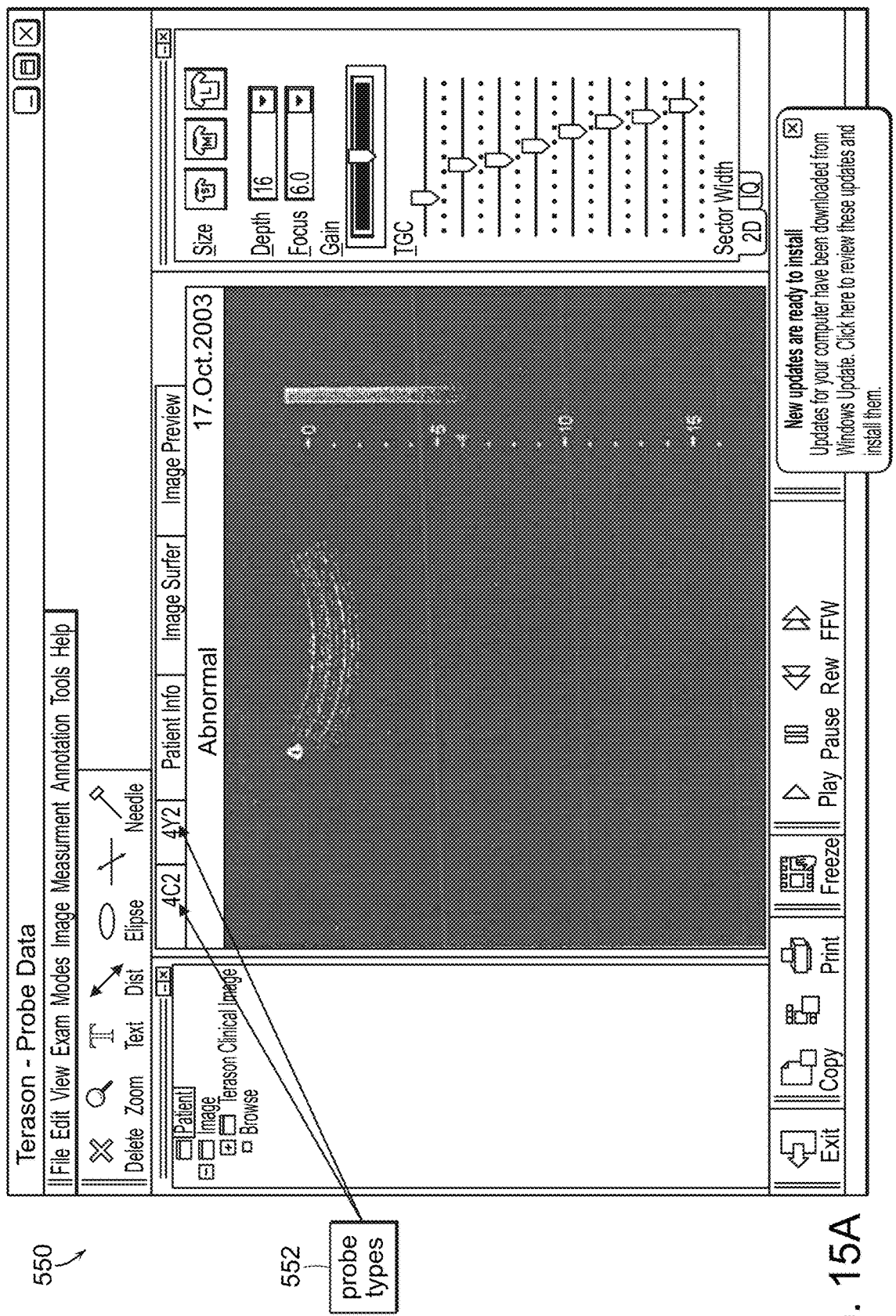
FIG. 15A illustrates a view of a graphical user interface display screen showing the appropriate transducer parameters upon connection of a transducer probe with the ultrasound processing unit in accordance with a preferred embodiment of the present invention.

Each ID chip has a unique serial number, plus a writable/readable memory for storage of calibration or additional identification data. In an ultrasound application of a preferred embodiment, the serial number and probe type information are accessed from memory upon probe insertion. The information is used to call up the appropriate transducer parameters and the new probe is then made available to the user on the display screen, as shown in FIG. 15A. FIG. 15A illustrates a view of a graphical user interface display screen showing the appropriate transducer parameters upon connection of a transducer probe with the ultrasound processing unit in accordance with a preferred embodiment of the present invention.

In addition to the identification, each transducer is unique and it is desirable to calibrate out these differences in accordance with a preferred embodiment of the present invention. Therefore, software executable instructions are provided by the ultrasound applications control for storing and retrieving individual calibration data to the ID chip. Examples of calibration differences can include electrical, acoustic and mechanical differences. These may be used, but are not limited to, procedures such as mounting of needle guides for biopsy, three-dimensional positioning sensing devices and transducer element variation calibration.

A method of probe type identification is usually provided by using multiple connector pins which are tied to logic zero or one. To differentiate between 32 probe types, 5 connector wires are required. In the one-wire method, only a single wire is required, and the data is passed between the probe and the host system serially.

The invention incorporates a read/writable non-volatile memory chip (ID chip) in the transducer termination board, as shown in FIG. 14. An example of the memory chip is the Dallas Semiconductor DS2433 One-wire Identification chip with 4096 bits of non-volatile storage. Other non-volatile read/writable memory can be used, but the One-wire chip has the advantage of using only one signal wire and one ground wire, and does not require additional pins for power supply.

The memory of the ID chip is organized as 128 words of 32 bits wide, divided into four segments: The IDENTIFICATION segment, the USAGE segment, the FACTORY segment and the USER segment shown in FIG. 15B.

The IDENTIFICATION segment holds the information which identifies the transducer type and hardware revision and serial number. The Ultrasound Application reads these information when a transducer is attached to a system and performs the appropriate set up based on the transducer type and hardware revisions. This segment is written at the factory and is not modifiable by the user.

The USAGE segment holds the statistical information about the usage of the transducer. The first entry logs the serial number and date when the transducer is first used outside of the factory (the Inauguration System Serial # and Date code). The second and third entries in this segment logs the serial number and the date of the two systems most recently the transducer was attached to. The Date Code values are Julian date of the connection date minus the Julian date of Jan. 1, 2000. The 16 bit date code field can store dates of more than a century starting from the year 2000. The 16 but date code filed can store dates of more than a century starting from the year 2000. The fourth word of the USAGE segment is a counter which increments once per 5 minutes when a transducer is attached and activated in a system. These statistical information are updated in the field by the Ultrasound Application software, and is not modifiable by the user. The values are set to zeros before the transducer leaves the factory. These statistical information are read and recorded when a transducer is returned to the factory for service.

The FACTORY segment holds the factory calibration information for the transducer. Examples of factory calibration data are the per element gain and propagation delay fine adjustments. When a transducer is attached and activated by the Ultrasound Application, the application first reads the transducer ID information from the IDENTIFICATION segment and loads up the appropriate set ups for that particular transducer type. The application then reads the FACTORY segment and applies the fine adjustments to the transducer set up. This segment is written at the factory and is not modifiable by the user.

The USER segment is reserved for the end user to store post-factory calibration data. Example of post-factory calibration data are position information of needle guide brackets and 3-D position sensing mechanism. The USER segment is the only segment which the user application software can modify.

Figure 15C:
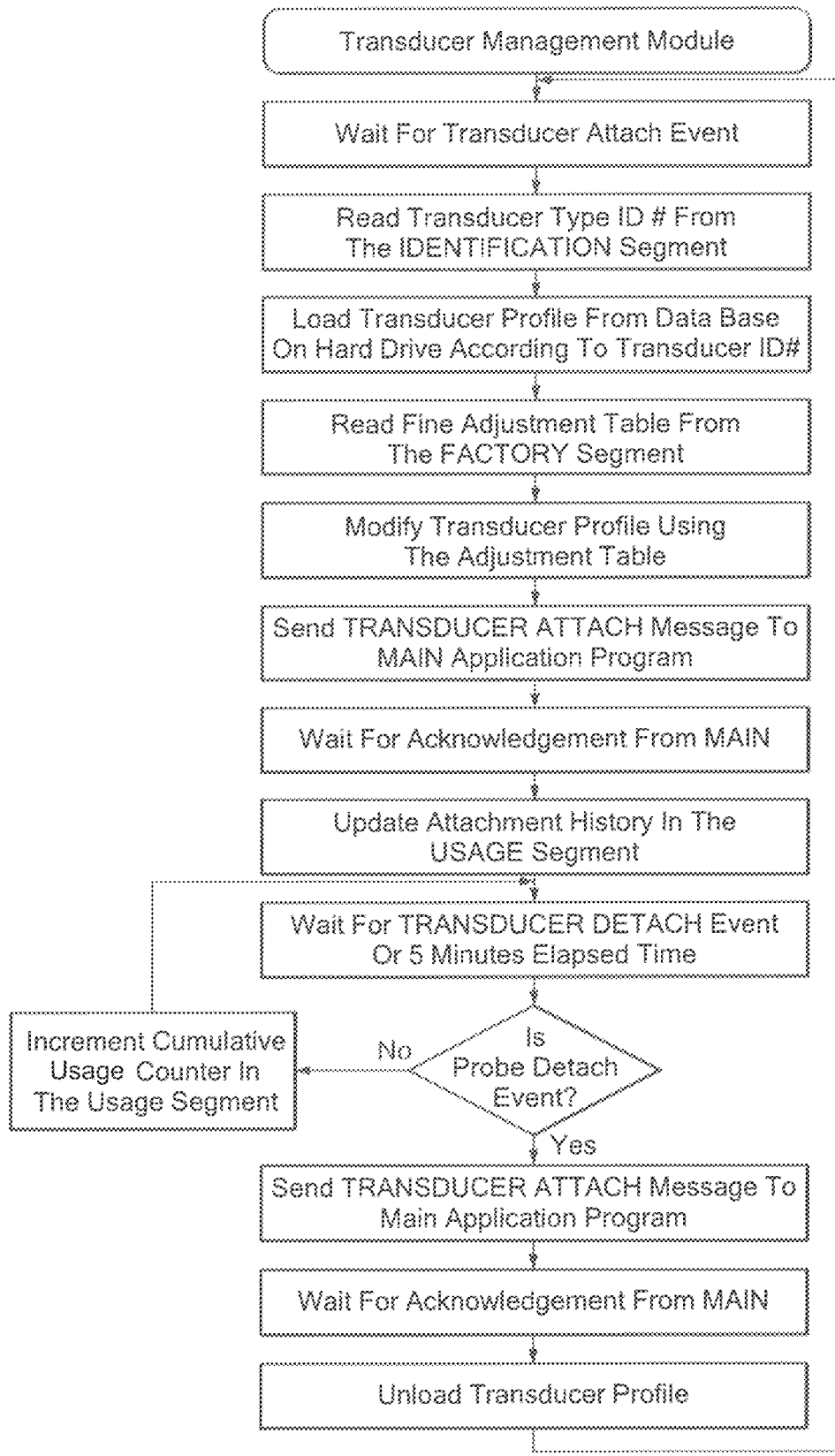
FIG. 15C illustrates a process sequence using the ID Chip.

FIG. 15C shows the software flow-chart of a typical transducer management module within the ultrasound application program.

When a TRANSDUCER ATTACHE event is detected, the Transducer Management Software Module first reads the Transducer Type ID and hardware revision information from the IDENTIFICATION Segment. The information is used to fetch the particular set of transducer profile data from the hard disk and load it into the memory of the application program. The software then reads the adjustment data from the FACTORY Segment and applies the adjustments to the profile data just loaded into memory. The software module then sends a TRANSDUCER ATTACHE Message to the main ultrasound application program, which uses the transducer profile already loaded and perform ultrasound imaging. The Transducer Management Software Module then waits for either a TRANSDUCER DETACH event, or the elapse of 5 minutes. If a TRANSDUCER DETACH is detected, the transducer profile data set is removed from memory and the module goes back to wait for another TRANSDUCER ATTACHE event. If a 5 minutes time period expires without TRANSDUCER DETACH, the software module increments the Cumulative Usage Counter in the USAGE Segment, and waits for another 5 minutes period or a TRANSDUCER DETACH event.

There are many types of ultrasound transducers. They differ by geometry, number of elements, and frequency response. For example, a linear array with center frequency of 10 to 15 MHz is better suited for breast imaging, and a curved array with center frequency of 3 to 5 MHz is better suited for abdominal imaging.

It is often necessary to use different types of transducers for the same or different ultrasound scanning sessions. For ultrasound systems with only one transducer connection, the operator will change the transducer prior to the start of a new scanning session.

In some application, it is necessary to switch among different types of transducers during one ultrasound scanning session. In this case, it is more convenient to have multiple transducers connected to the same ultrasound system, and the operator can quickly switch among these connected transducers by hitting a button on the operator console, without having to physically detach and re-attach the transducers, which takes a longer time.

Traditionally, the switching among different connected transducers is implemented either by arrays of relays, or by arrays of high voltage Multiplexer integrated circuits. (switching between two 128-elements transducers). These relays or MUXIC's form an additional layer of circuits between the ultrasound transmitter/receiver circuits and the transducer connectors.

Figure 15D:
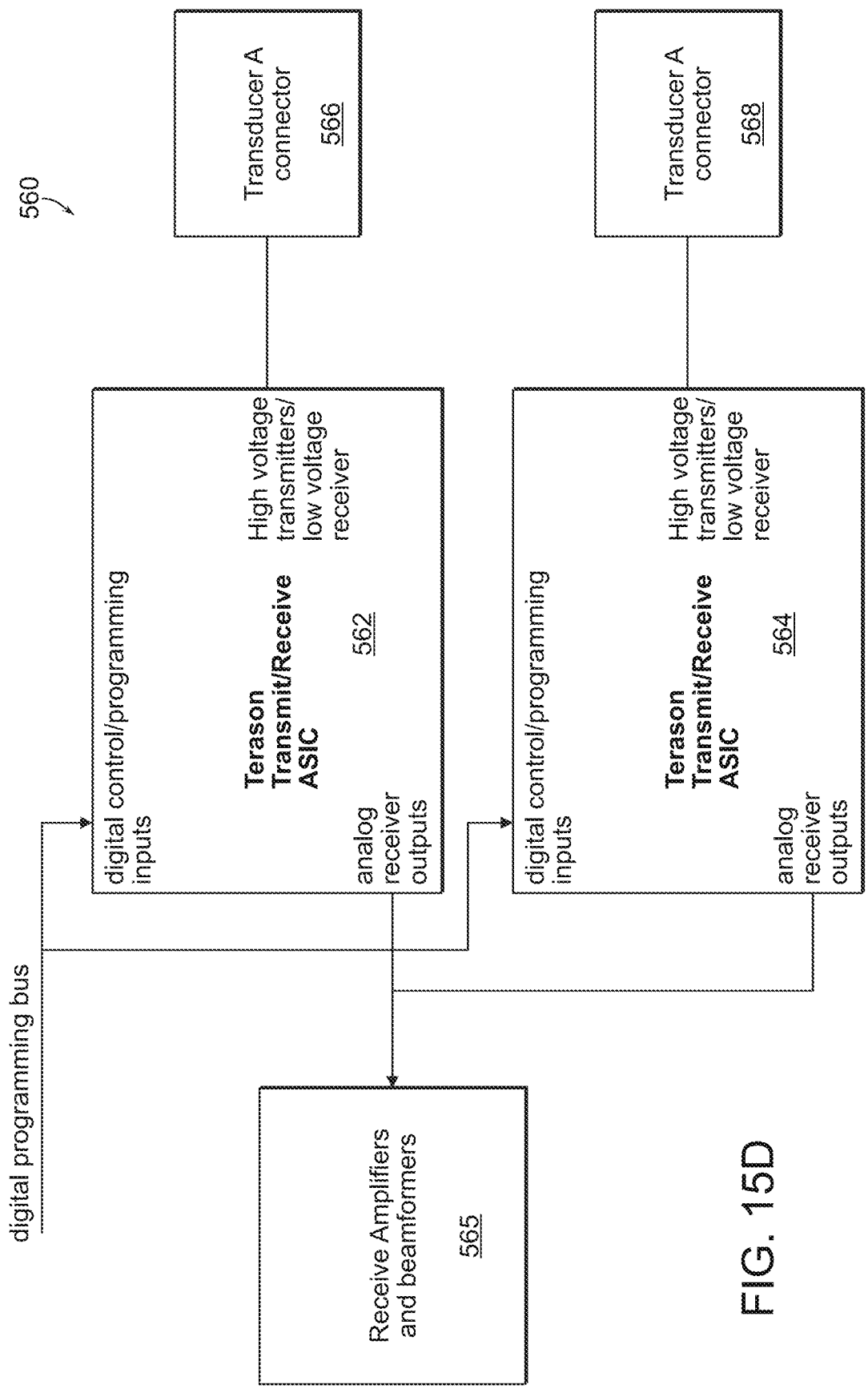
FIG. 15D shows a circuit diagram for a multiple connector assembly in accordance with the invention.
Figure 15E:
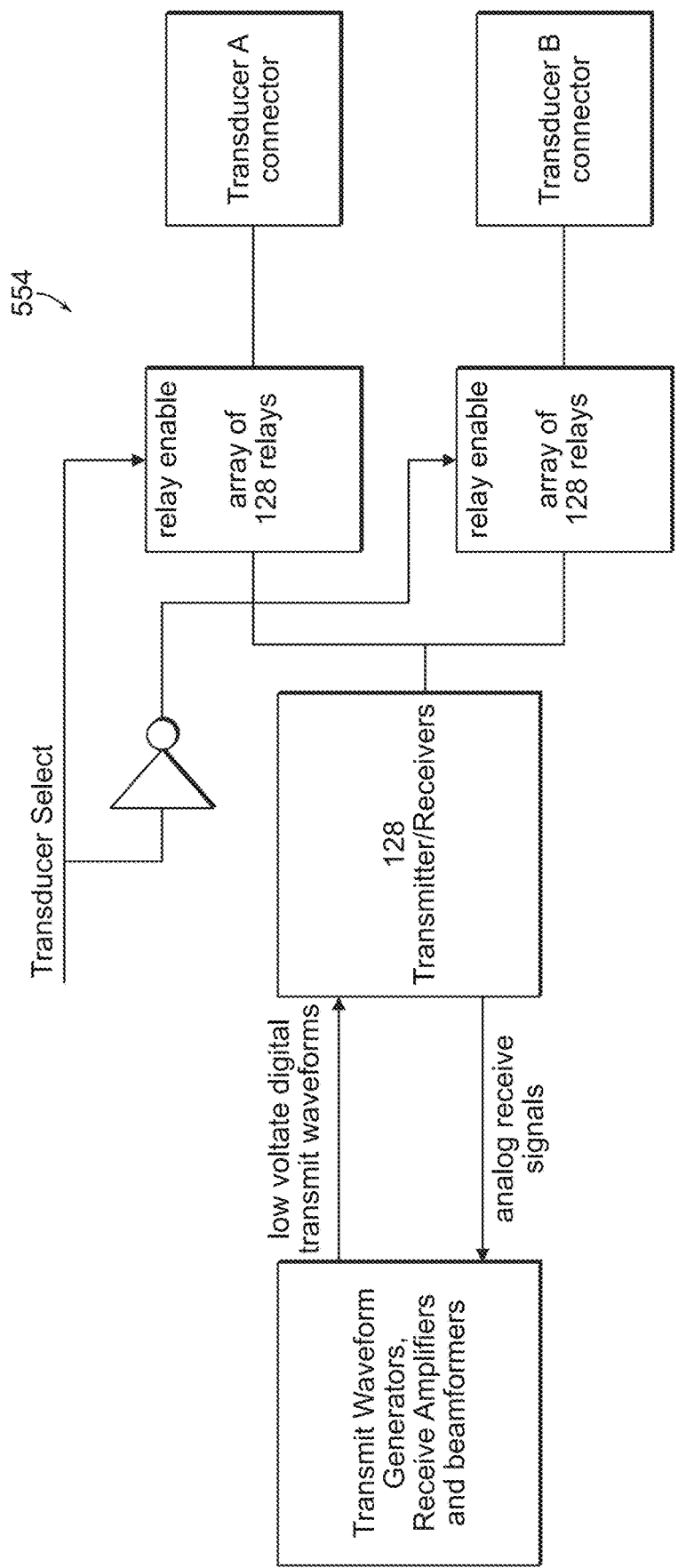
FIG. 15E illustrates a schematic circuit diagram for a multiplexed multiconnector system for transducer arrays.
Figure 15F:
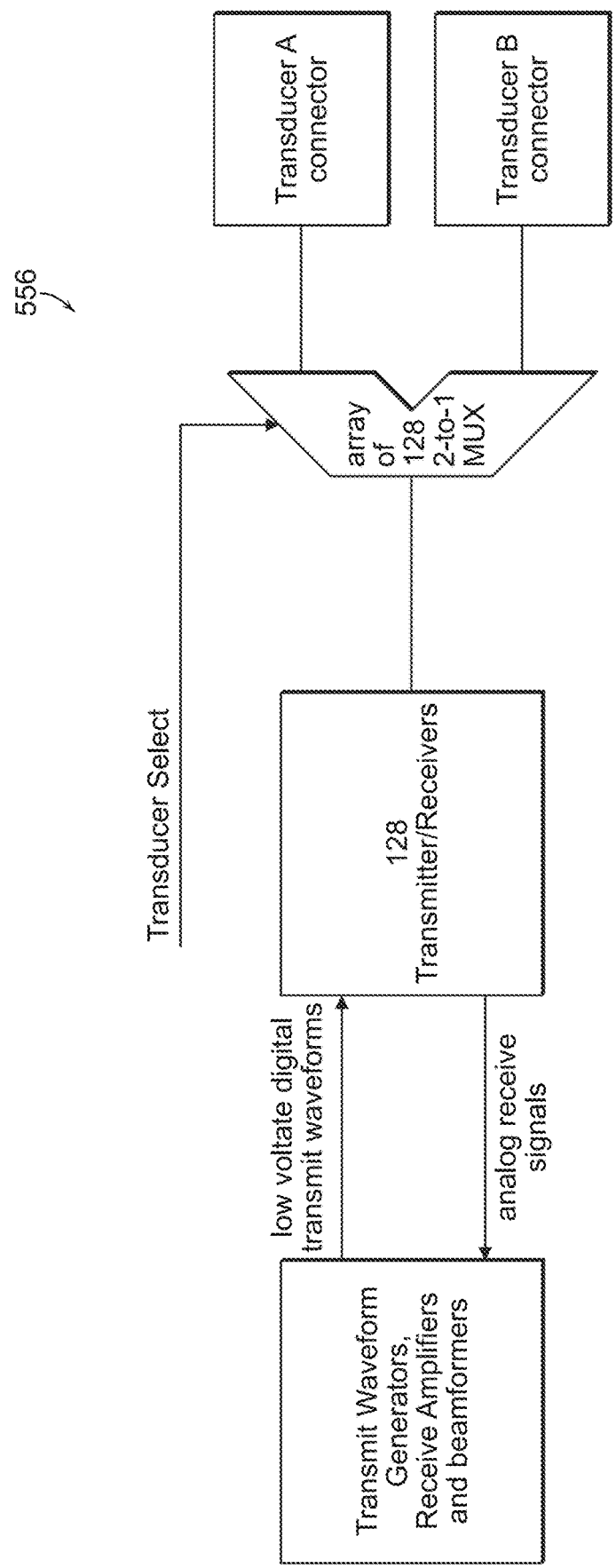
FIG. 15F illustrates another preferred schematic circuit diagram for a multiconnector system for transducer arrays.

The present invention utilizes a system that performed a method of multi-transducer switching using multiple Transmit/Receive integrated circuits, without the use of relays or commercial multiplexer integrated circuits. A typical two transducer switching circuit using an integrated circuit in accordance with the invention is shown in FIG. 15D.

The Transmit/Receive integrated circuit includes multiple channel devices with a programmable waveform generator and high voltage driver for each transducer element, and a receive routing circuit for each element pair. The receive output is programmable to receive from transducer element A or B of the element pair, or turned off. The outputs of multiple integrated circuits are wired together. Connection to different transducers in the same system 5 is achieved by programming the On/Off states of individual receive channels among the multiple integrated circuits, and by programming the transmit sequence of each of the transmit channels on all of the integrated circuits.

One advantage of this approach is the higher integration over the use of commercial available relays and multiplexer chips, especially when compared to a relay switching approach, because relays are mechanical devices and are generally larger. There are two versions of the these, Transmit/Receive integrated circuits, one version has 64 transducer element channels and another version has 32 transducer channels. This high channel count integration of at least 32 channels combined with the small high pin density transducer connector, allows implementation of a multiple transducer configuration in a very compact size.

Another advantage is the elimination of an extra circuit layer, when compared to the multiplexer chips approach.

Typical commercial multiplexer chips suitable for ultrasound channel switching typically have an ON resistance of greater than 20 ohms (example, Supertex HV20220), and therefore have measureable attenuation of both the transmit and receive signals compared with a direct connection in a single transducer system. The present approach has identical transmit/receive circuit for single transducer system, or multiple transducers system, with no additional signal attenuation resulting from adding the multiple transducers switching function.

Yet another advantage of the present approach is the added ability to operate a very large element count transducer with a true full transmit aperture. For example, a 128 channel ultrasound engine can operate a 768 element linear array by adding a one to six multiplexer array. A traditional implementation using relays of multiplexers can switch among six segments of 128 elements each across the entire 768 elements at any one time. The present approach will have 768 programmable transmitter, and therefore can use any size of transmit aperture anywhere on transducer array, including using the entire 768 element at the same time. The ability to use larger than 128 element transmit aperture allows the ultrasound system to have better penetration and resolution, compared to systems that are limited to 128.

Figure 15G:
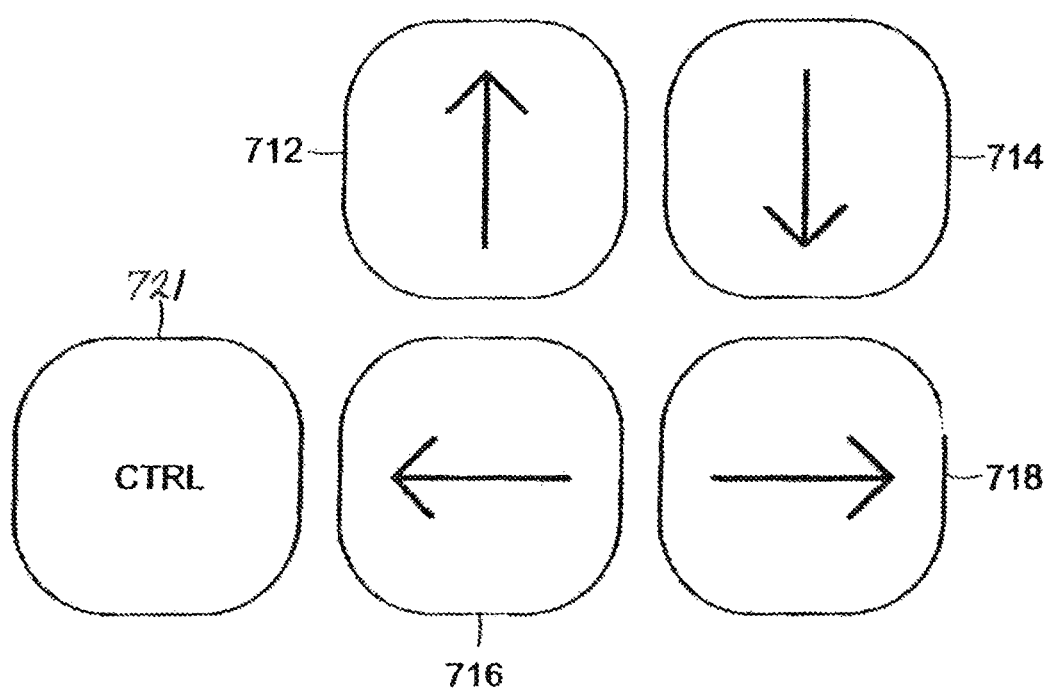
FIG. 15G shows a unitary control keypad for use in conjunction with e GUI of FIGS. 15H-15I.

FIG. 15G shows the unitary, directional keypad which provides a single operating position from which to control the ultrasonic imaging operations. The quantitative parameters may be in a range of discrete values, or may span a continuum. A control key 721, employed in conjunction with the up arrow key 712 or down arrow key 714 allows an operator to toggle between two control tabs depicted in FIGS. 15H and 15I, as will be described further below. Since all keys 712, 714, 716, 718 employed in controlling and selecting the ultrasonic imaging operations are accessible from a common operating position, an operator may focus on the ultrasonic image of the subject and on the hand-held probe, and need not be distracted by unwieldy controls. Traditional directional keypads allow only directional control to be applied by the directional keypads, and do not allow both qualitative and quantitative selection of operations from a common, unitary operating position accessible by a single hand.

Figure 15H:
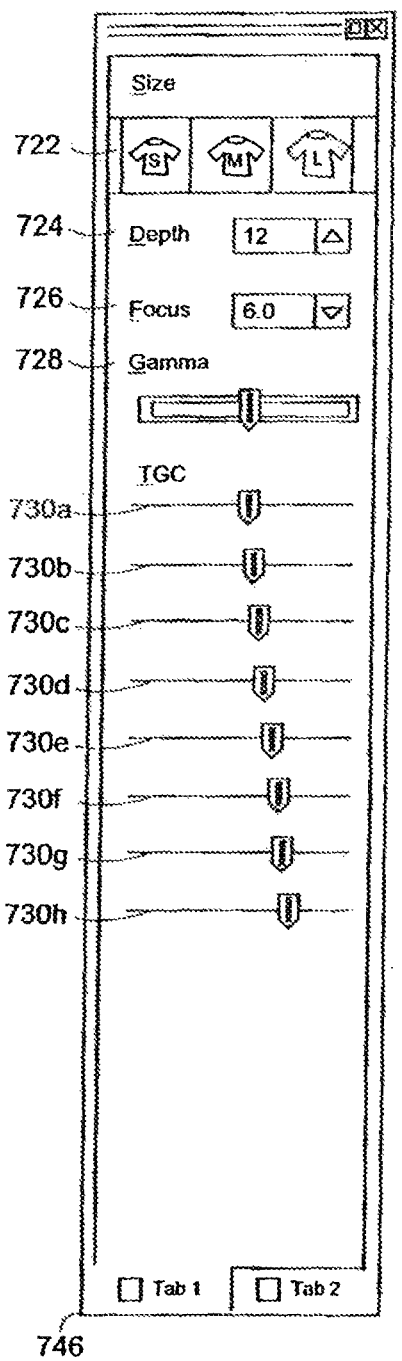
FIG. 15H shows a graphical user interface (GUI) for controlling the scanning operations of the ultrasonic imaging system.
Figure 15I:
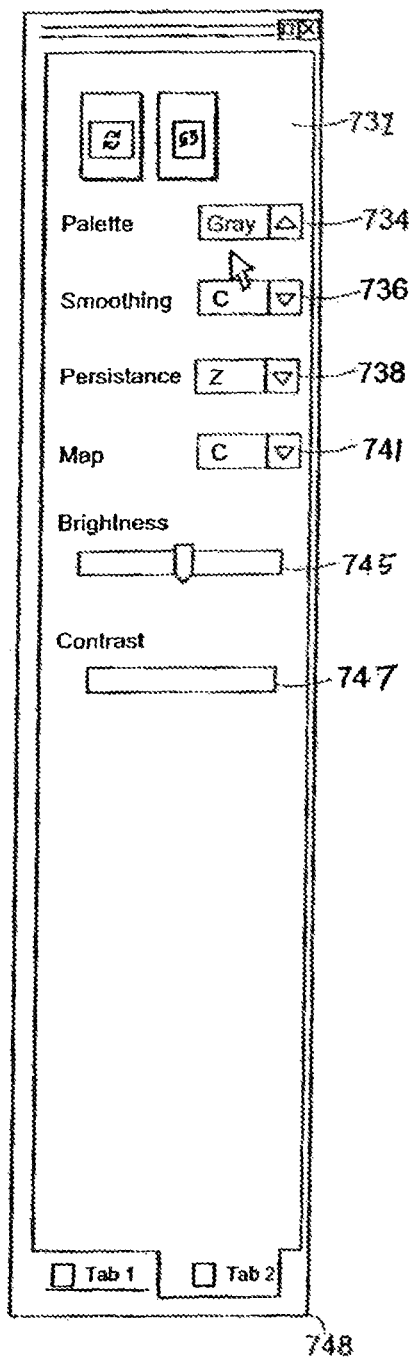
FIG. 15I shows a graphical user interface (GUI) for controlling the processing operations of the ultrasonic imaging system.

FIGS. 15H and 15I show qualitative and quantitative selection of ultrasonic imaging operations via invoking the unitary directional keypad. Referring to FIG. 15H, ultrasonic imaging operations applicable to scanning are shown. The scanning operations are directed to active acquisition of real-time, dynamic ultrasonic image data, and are typically applied as the hand-held probe is manipulated over the subject imaging area. A size operation 722 sets a series of predetermined defaults for other ultrasonic imaging operations. A small, medium, or large subject may be selected via the left 716 and right 718 arrow keys. A depth operation 724 allows selection of a depth parameter via the arrow keys. Focus is controlled by a focus 726 operation. Gain 728 control adjusts the TGC for all TGC settings 730*a*-730*h*. TGC operations 730*a*-730*h* adjusts amplification of return signals at varying depth, ranging from the least depth 730*a* to greatest depth 730*h*, via the arrow keys.

Referring to FIG. 15I, ultrasonic imaging operations applicable to processing are shown. The processing operations may be applied to static real-time or frozen images. An inversion operation is controlled by the inversion 731 selection, and rotates the image via the arrow keys. Palette, smoothing, persistence, and mapping 734, 736, 738 and 741, respectively are selected via the up and down arrow keys, and parameters selected via the arrow keys. Brightness and contrast scales are selected via sliders 745 and 747, respectively, and are changed using arrow keys.

Figure 15J:
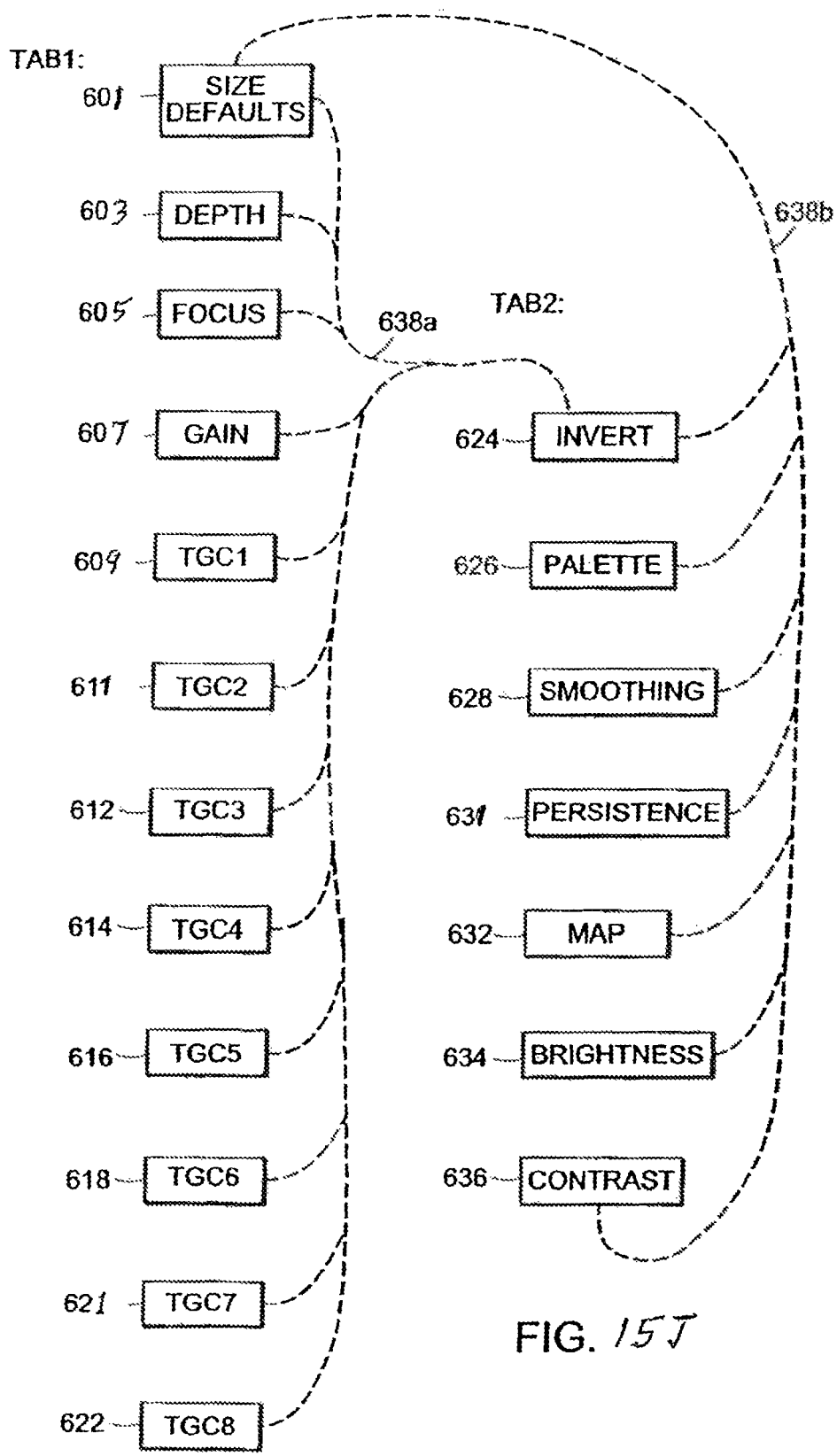
FIG. 15J shows a state diagram corresponding to the GUI of FIGS. 15H-15I.

FIG. 15J shows a state diagram depicting transition between the ultrasonic imaging operations depicted in FIGS. 15H and 15I. Tab 1 operations are selected via the up and down arrow keys and transition according to the following state sequence: size 601, depth 603, focus 605, Gain 607 and TGC degrees 609, 611, 612, 614, 616, 618, 621 and 622. Similarly, the Tab 2 operations are selected according to the following sequence: invert 624, palette 626, smoothing 628, persistence 631, map 632, brightness 634, and contrast 636. As indicated above, selection of operations may be toggled between Tab 1 and Tab 2 using control key and arrow keys.

The scanning operations shown in FIG. 15H are displayed on Tab 1. The processing operations shown in FIG. 15I are displayed and selected on Tab 2. Control is toggled between Tab 1 and Tab 2 using a combination of the control key and either the up or down arrow keys as shown by dotted lines 638*a* and 638*b*.

In general the use of medical ultrasound systems requires the user to have significant training and regular practice to keep skills at a high level. Another embodiment of the invention involves providing the user with an intuitive and simple way to use the interface, and with the ability to quickly and automatically set imaging parameters based on a software module. This enables general medical personnel with limited ultrasound experience to obtain diagnostic-quality images without having to adjust the controls. The "Quick Look" feature provides the user with a very simple mechanism of image optimization. It allows the user to simply adjust the image so as to obtain appropriate diagnostic image quality with one push of one button.

The benefits of programmed image parameters are many. The user no longer is required to adjust multiple controls in order to obtain a good image. Exams may be performed in a shorter period of time as a result. The use of this feature also results in more uniform images, regardless of the skills and expertise of the user. This approach is advantageous when performing exams under adverse circumstances such as emergency medical procedures performed in ambulances or remote locations.

The procedure involves the use of predefined histograms. Separate histograms are provided for different anatomical structures that are to be examined. The user chooses a structure, similar to the existing method of choosing a preset. Once the structure is chosen, the user places the transducer on the area of interest in the scanning window. At that time, pressing the selected control button triggers the system to adjust the system contrast and brightness control values so that a histogram of the gray levels in the image closely matches the corresponding pre-defined histogram for that structure. The result is an image of diagnostic image quality that is easily recreated.

The procedure is highly dependent upon the brightness and contrast controls. As a result, a preferred embodiment provides an independent control which allows the user to adjust for ambient lighting changes. In many applications the programmed parameters gets the user very close, but they may choose to fine tune the contrast and brightness.

Figure 16:
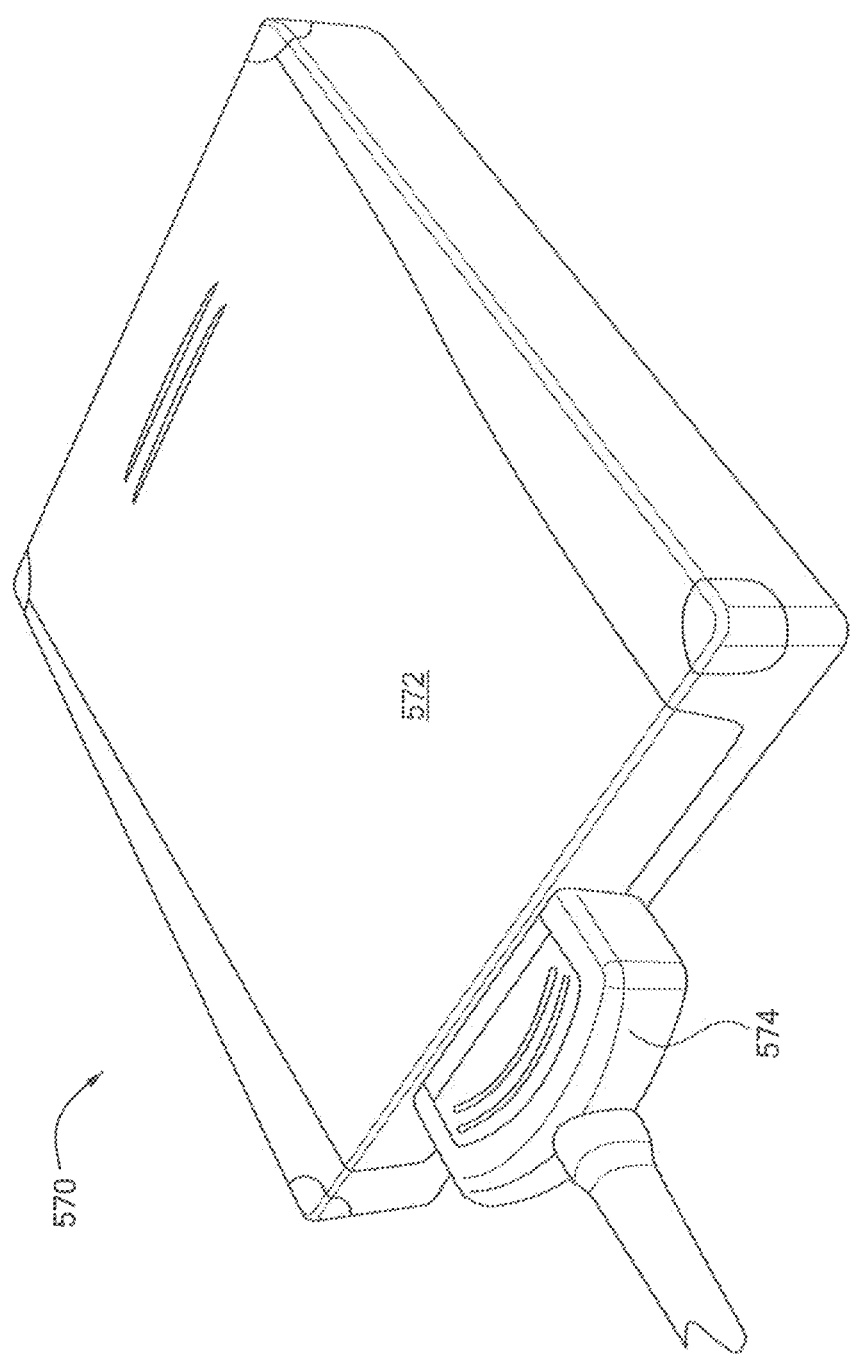
FIG. 16 illustrates an ultrasound processing unit and an ultrasound transducer connector in accordance with a preferred embodiment of the present invention.

FIG. 16 illustrates an ultrasound processing unit and an ultrasound transducer connector in accordance with a preferred embodiment of the present invention. An ultrasound transducer is coupled to its associated ultrasound processing unit 572 via a cable, which is routed into an ultrasound transducer connector assembly 574 and, mates with a corresponding 5 terminal located on ultrasound console. A sliding lever is included to secure the connector to the processing unit.

Figure 17A:
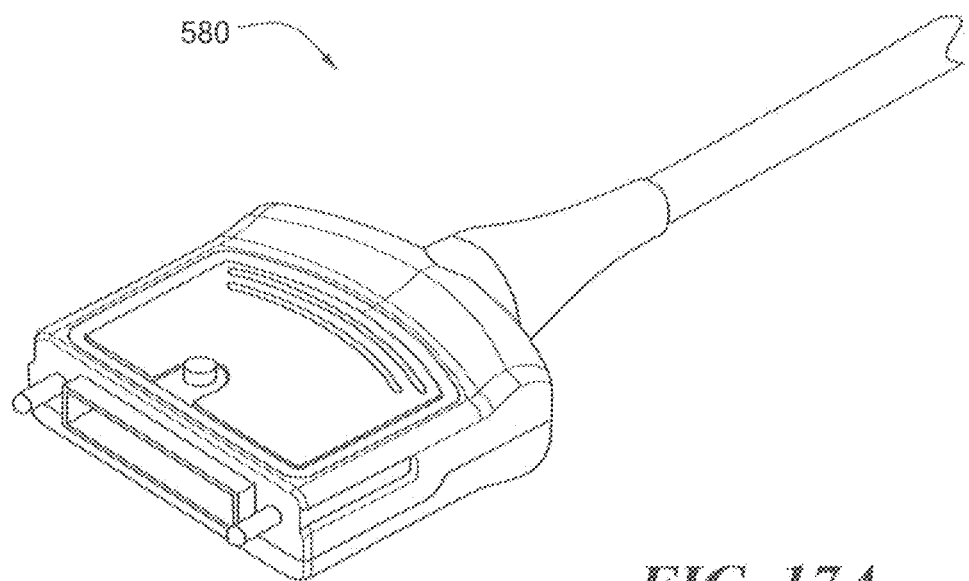
FIGS. 17A and 17B illustrate views of an ultrasound transducer connector assembly in accordance with a preferred embodiment of the present invention.
Figure 17B:
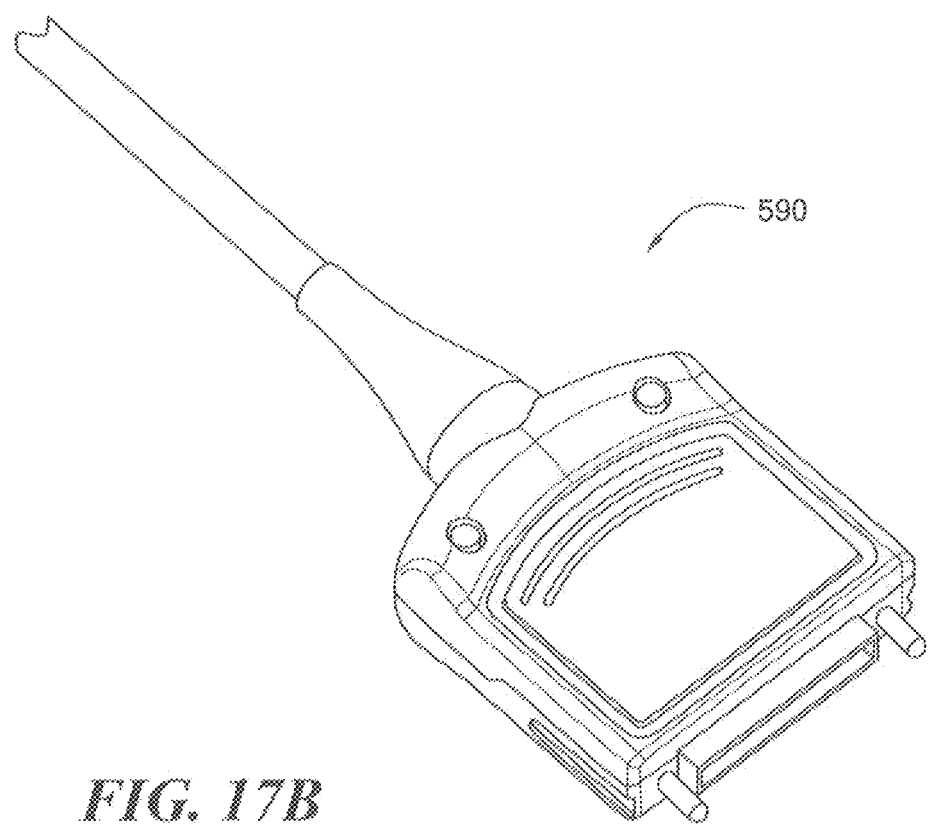
Figure 18:
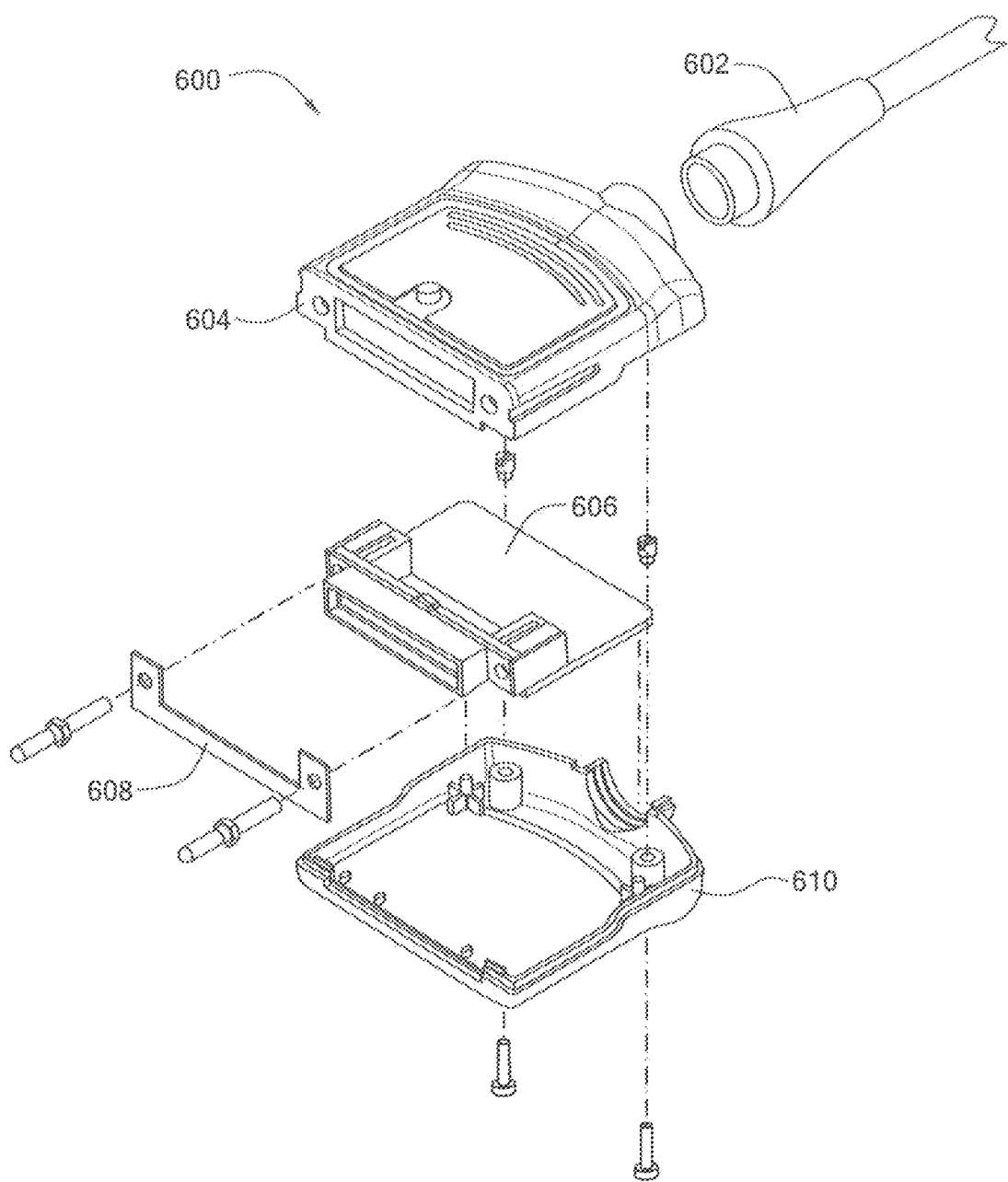
FIG. 18 is an exploded view of the ultrasound transducer connector assembly illustrated in FIGS. 17A and 17B in accordance with a preferred embodiment of the present invention.

FIGS. 17A and 17B illustrate views of an ultrasound transducer connector assembly in accordance with a preferred embodiment of the present invention. The ultrasound transducer connector assembly 18 shows a connector housing. FIG. 18 is an exploded view of the ultrasound transducer connector assembly illustrated in FIGS. 17A and 17B in accordance with a preferred embodiment of the present invention. An electrical connector 606 may have as many as 160 contacts. The connector assembly housing 604, 610 interfaces with a cable 602 which in turn is coupled to an ultrasound transducer.

Figure 19A:
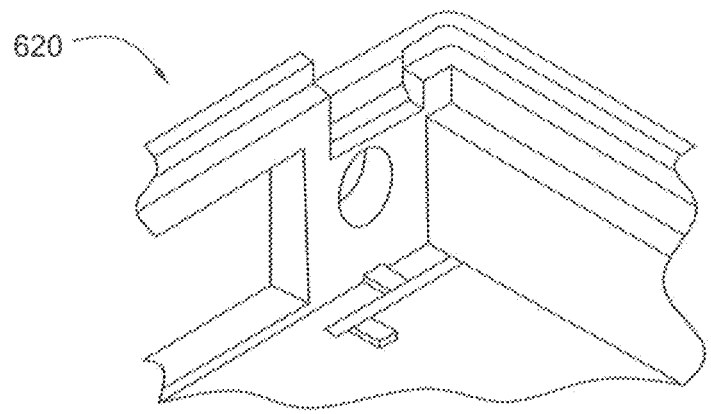
FIGS. 19A, 19B and 19C illustrate detailed views of the ultrasound transducer connector assembly including sectional views in accordance with a preferred embodiment of the present invention.
Figure 19B:
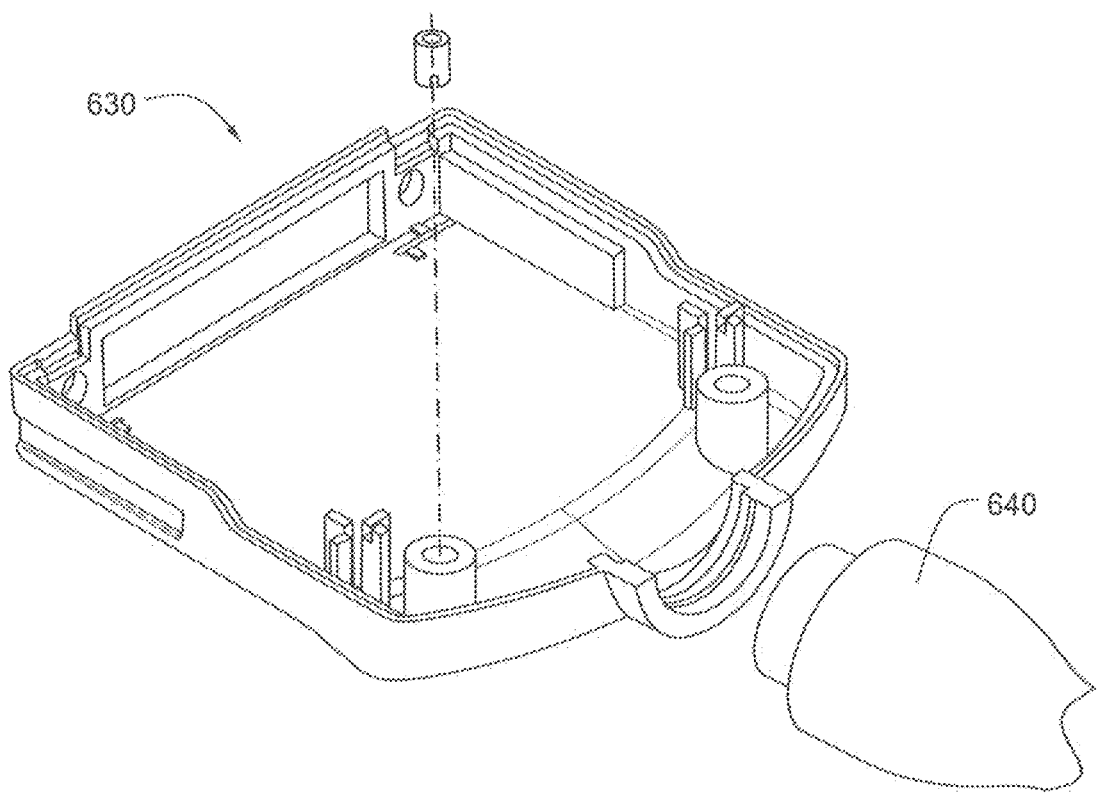
Figure 19C:
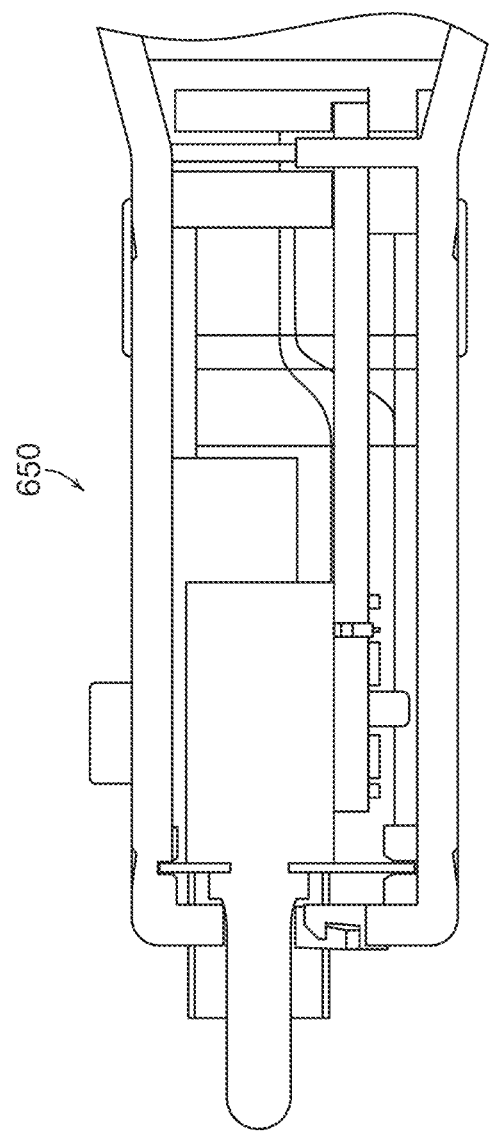

FIGS. 19A, 19B and 19C illustrate detailed views of the ultrasound transducer connector assembly including sectional views in accordance with a preferred embodiment of the present invention. A cable 640 is attached to a first end of connector housing element 630. A close-up view 620 of connector assembly element 620 is seen in FIG. 19A. A side view 650 is shown in FIG. 19C.

The movable connector component has electrical contacts that mate with the stationary connector component having stationary electrical contacts on the processing unit. For mating, the movable connector component is brought towards the stationary connector component. Initially, there is a gap separating the movable electrical contacts from stationary electrical contacts, so that the contacts are not subjected to any friction or insertion force. A locking mechanism draws in the movable connector component which is received in a recess of the stationary connector component. The lever slides from right to left causing the movable connector component to close into the recess and contact the corresponding stationary electrical contacts to make an electrical connection. The ultrasound transducer connectors minimize the physical stress exerted upon their electrical contacts, thus avoiding wear and potential damage to the contacts.

Figure 20:
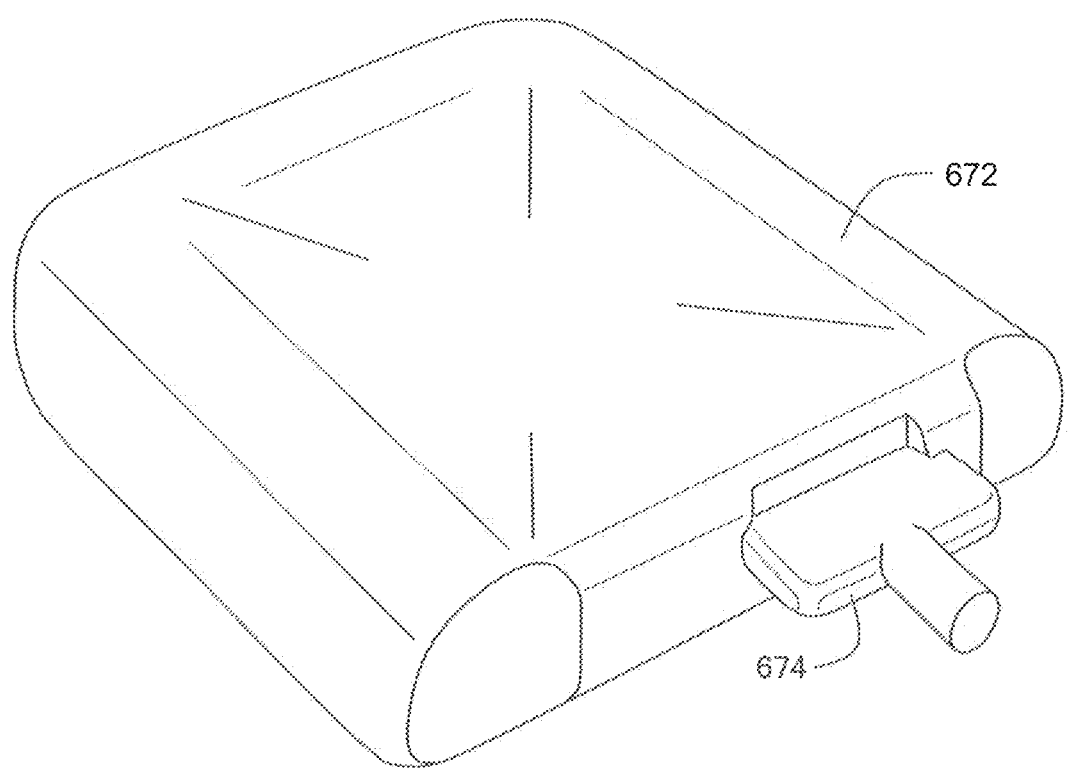
FIG. 20 illustrates a view of an ultrasound processing unit with an ultrasound transducer connector assembly having a lock in accordance with a preferred embodiment of the present invention.
Figure 21A:
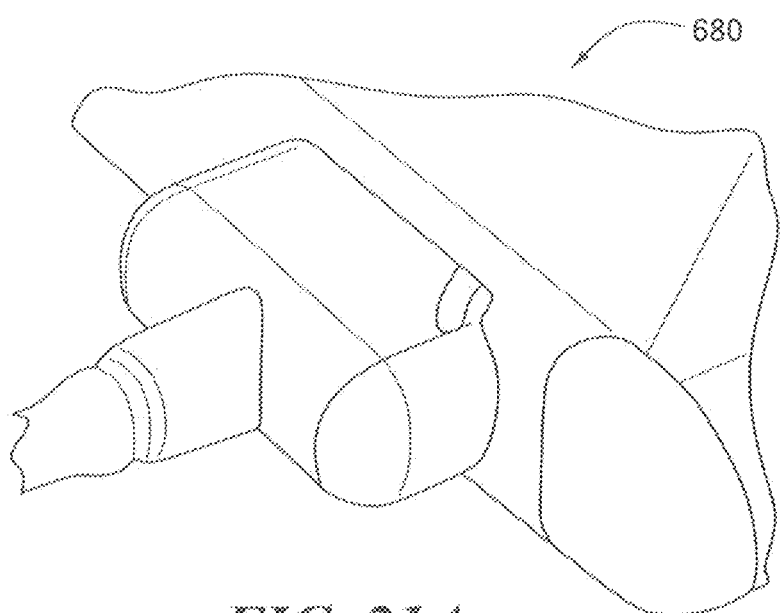
FIGS. 21A and 21B illustrate a close-up view of an ultrasound transducer connector assembly inserted into a ultrasound processing unit and a cut-away view of the inserted ultrasound transducer connector assembly, respectively, showing a sliding lever in accordance with a preferred embodiment of the present invention.
Figure 21B:
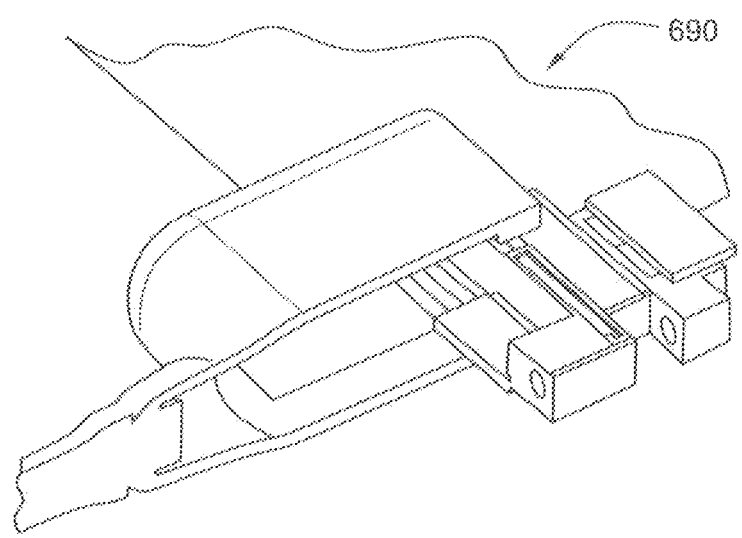

FIG. 20 illustrates a view of an ultrasound processing unit with an ultrasound transducer connector assembly 674 having a lock 672 in accordance with a preferred embodiment of the present invention. FIGS. 21A and 21B illustrate a close-up view of an ultrasound transducer connector assembly inserted into a ultrasound processing unit and a cut-away view of the inserted ultrasound transducer connector assembly, respectively, showing a sliding lever in accordance with a preferred embodiment of the present invention. The connector is drawn in the end of the housing when inserted and locked and is ejected when detached. The connector assembly in accordance with a preferred embodiment of the 5 present invention allows for a one-hand operation. A preferred embodiment of the present invention includes a sash lock similar to a window lock. The lever includes a lever action which also yields a significant mechanical advantage as it translates insertion force to a lateral action of the lock. The lever for the connector assembly is resistant to abusive use as it has rails which act with the lever to eliminate twists applied to the connector. A rotating catch is used to eject the connector after use.

FIGS. 22A and 22B illustrate views of an ultrasound transducer connector assembly inserted into an ultrasound processing unit 700 having a lever 732 shown in the detailed portion 720, to secure the connector assembly in accordance with a preferred embodiment of the present invention.

Figure 23A:
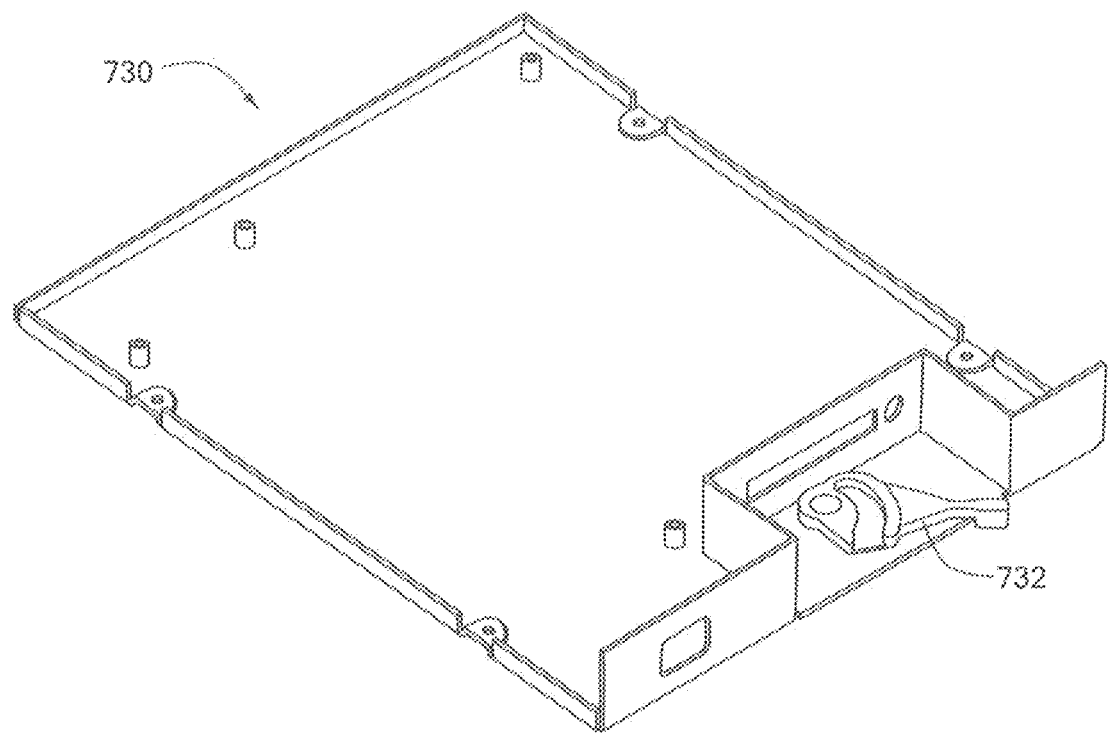
FIGS. 23A and 23B illustrate further details of the lever and an exploded view of the lever assembly of an ultrasound processing unit in accordance with a preferred embodiment of the present invention.
Figure 23B:
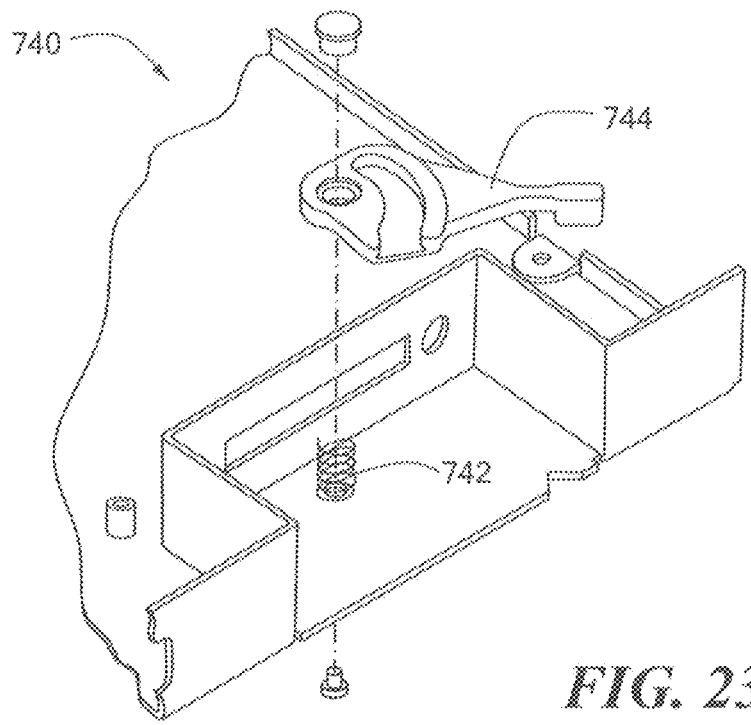

FIGS. 23A and 23B illustrate further details 730 of the lever 732 and an exploded view 740 of the lever assembly of an ultrasound processing unit in accordance with a preferred embodiment of the present invention. The lever assembly includes a spring 742 which being a resilient member, assists in drawing the lever 744 into the locked position. FIGS. 24A-24D illustrate several views of the ultrasound processing unit showing the ultrasound transducer connector assembly in accordance with a preferred embodiment of the present invention. Circuit boards are mounted in FIGS. 24B and 24C along with the connector assembly in accordance with the invention.

Figure 25:
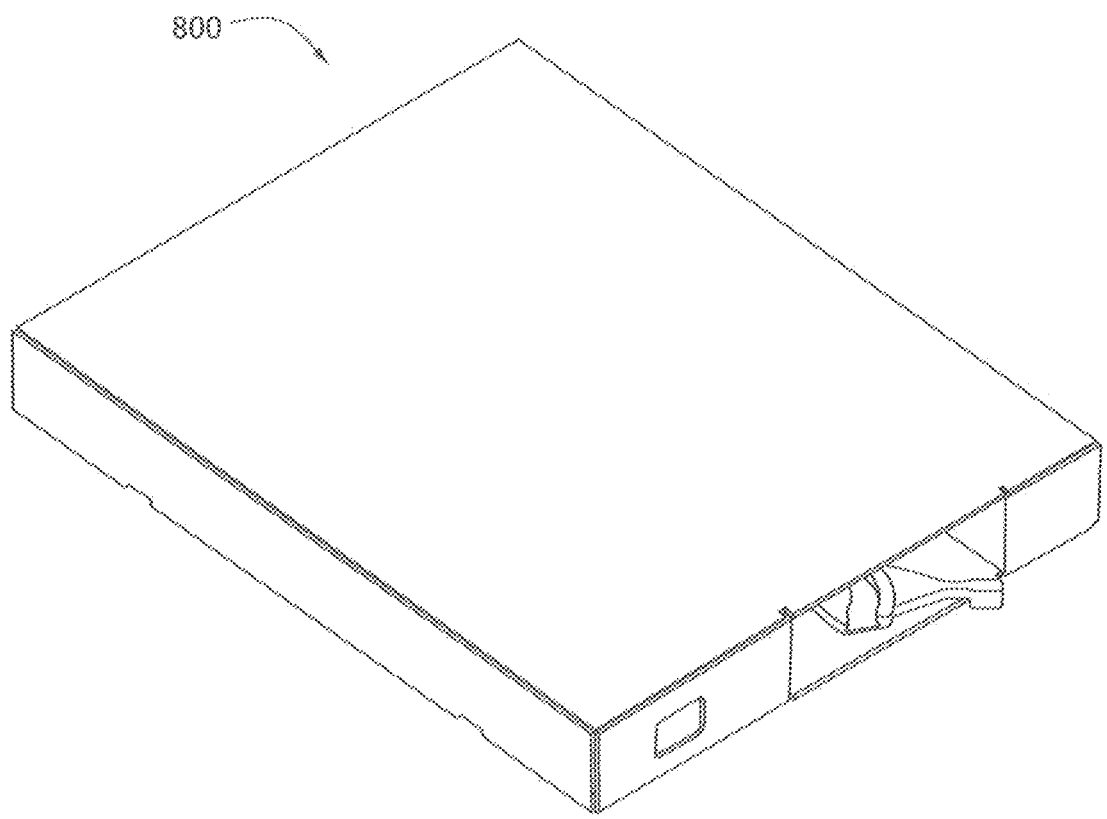
FIG. 25 illustrates a view of the ultrasound processing unit showing a partial view of the lever for the transducer connector assembly in accordance with a preferred embodiment of the present invention.

FIG. 25 illustrates a view of the ultrasound processing unit 800 showing a partial view of the lever for the transducer connector assembly in accordance with a preferred embodiment of the present invention.

Figures 26A, 26B:
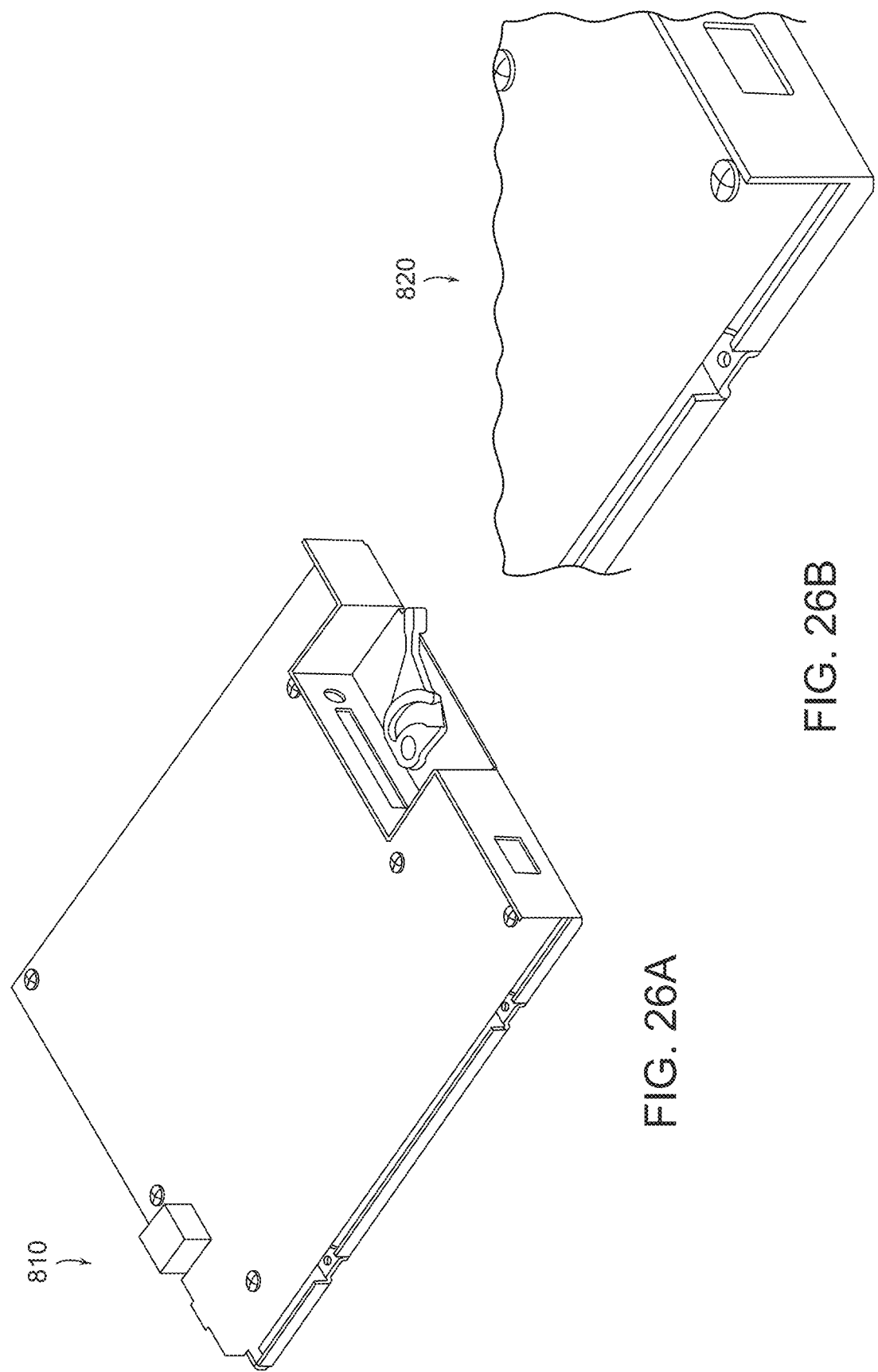
FIGS. 26A and 26B illustrate further views of the ultrasound processing unit showing the ultrasound transducer connector assembly in accordance with a preferred embodiment of the present invention.

FIGS. 26A and 26B illustrate further views 810, 820 of the ultrasound processing unit showing the ultrasound transducer connector assembly in accordance with a preferred embodiment of the present invention.

Figure 27A:
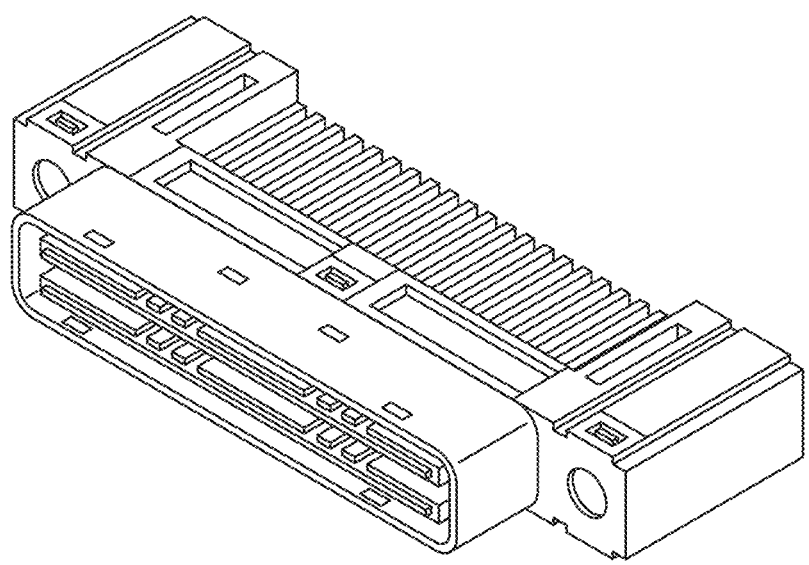

FIGS. 27A, 27B, and 27C illustrate views of an ultrasound transducer connector in accordance with a preferred embodiment of the present invention.

Figure 28A:
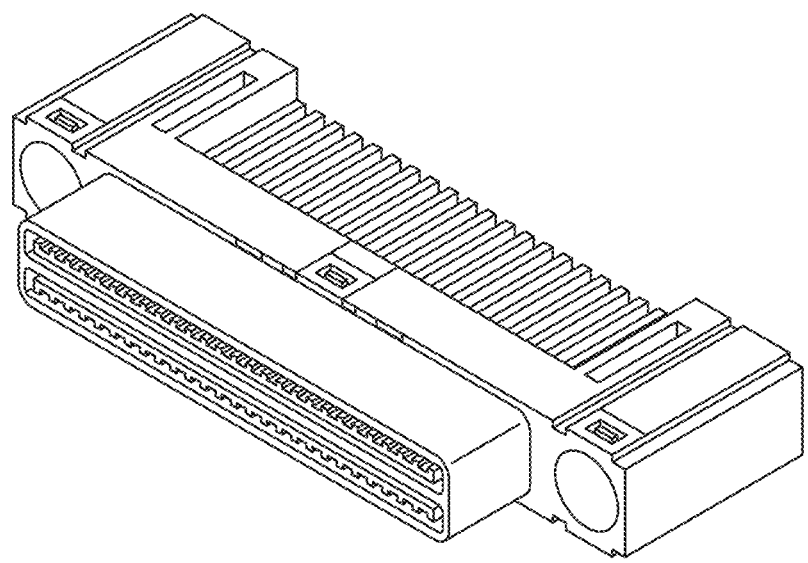

FIGS. 28A-28C illustrate views of an ultrasound transducer connector that mates with the connector of FIGS. 27A-27C in accordance with a preferred embodiment of the present invention. In a preferred embodiment the maximum voltage of the ultrasound transducer connector is 100 volts. The connector can include 160 or 240 circuits. The base plate protects the pins and rises up into position during printed circuit board insertion. In one embodiment the connector assembly includes, but is not limited to, a Molex® 53941 right angle docking station board-to-board shielded plug.

In this preferred embodiment the connector assembly includes, but is not limited to, a Molex® 54145 right angle docking station board-to-board shielded receptacle. The interlock can indicate that a probe has been inserted correctly.

Figure 29:
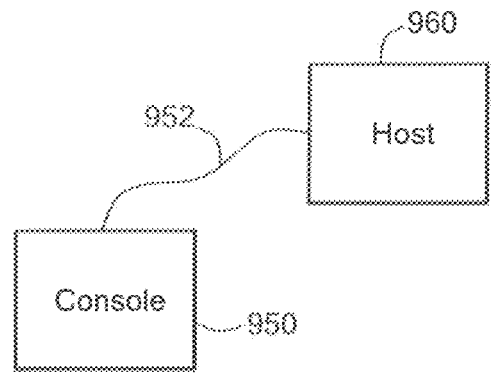
FIG. 29 illustrates a schematic view of an ultrasound system including an ultrasound console having a remote hardware keypad in accordance with a preferred embodiment of the present invention.

FIG. 29 illustrates a system that includes a console 950 connected with a USB/PS/2 interface 952 to a host computer 960.

Figure 30:
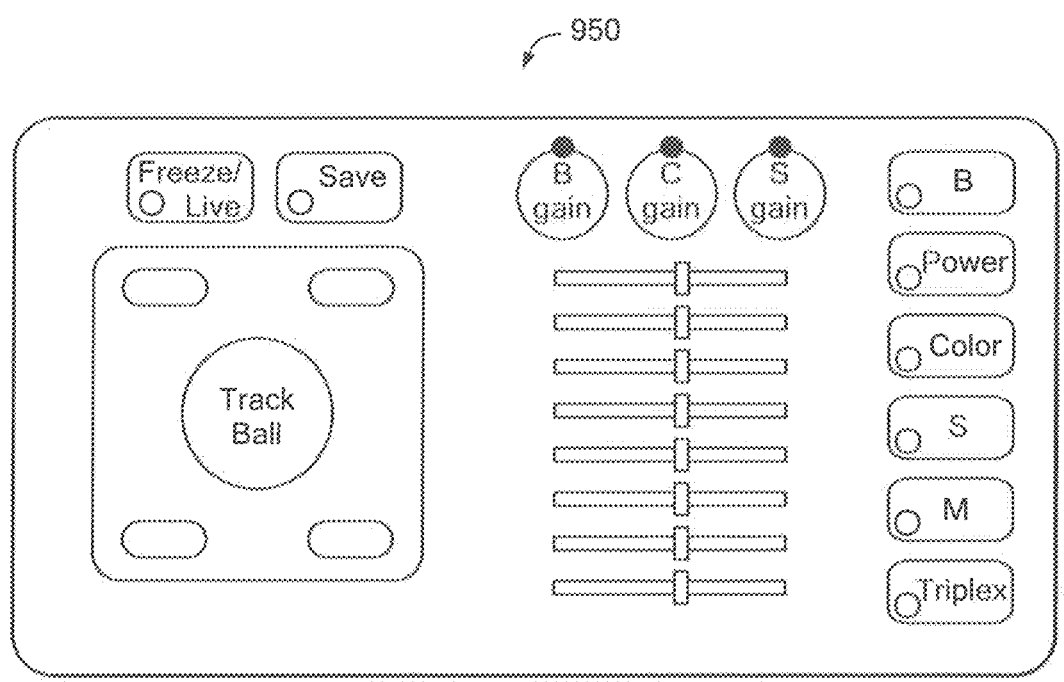
FIG. 30 illustrates a console control keypad in accordance with a preferred embodiment of the present invention.
Figure 32A:
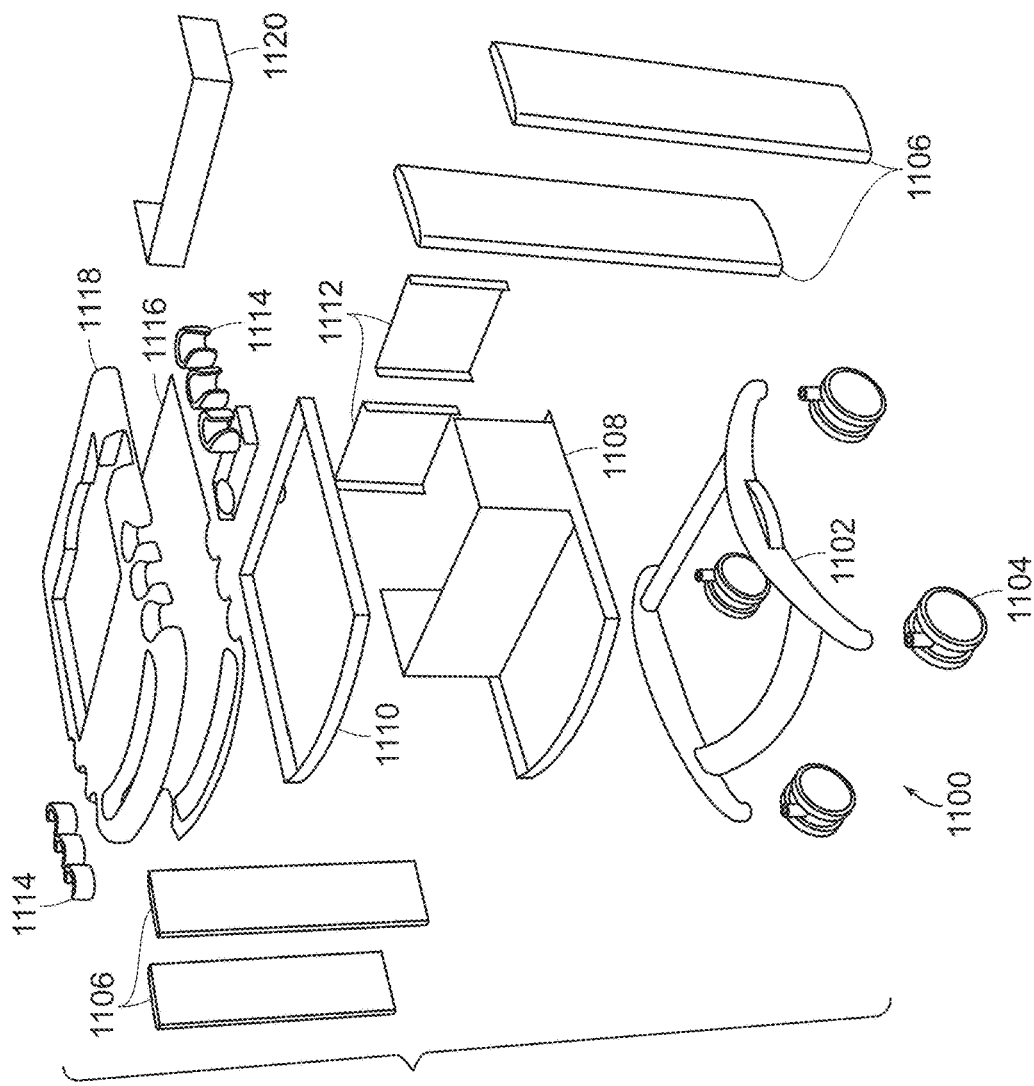
FIGS. 32A-32D illustrate a preferred cart system for use in embodiment of a conjunction with a modular ultrasound imaging system in accordance with the inventors.

FIG. 30 illustrates a schematic diagram of an ultrasound console in accordance with a preferred embodiment of the present invention. A universal serial bus (USB) console is used for a remote hardware keypad. This hardware user interface in accordance with a preferred embodiment of the present invention displaces a software graphical user interface and allows any ultrasound imaging control function to be accessed via a control keypad. The controls are communicated with a host computer through a USB port.

In a preferred embodiment, the ultrasound console includes a USB device and USB Driver which is implemented with a FTDI USB245M controller chip, for example. This integrated chip is simple as it can be integrated into the console without requiring a custom device driver. The USB Console uses the FTDI supplied dynamic link library (DLL) device driver in accordance with a preferred embodiment of the present invention.

The console in accordance with a preferred embodiment of the present invention is made up of at least four types of hardware functions: buttons, potentiometers, trackball, and LEDs. The buttons are momentary switches. The architecture in accordance with a preferred embodiment of the present invention allows for 128 buttons. The potentiometers are either linear slide potentiometers for time gain control (TGC), or rotary dials for GAINs. Each potentiometer can have a position reading between 0 and 255. A digital potentiometer with clickers is considered to be a button, not a potentiometer in the preferred embodiments. One embodiment includes 11 potentiometers: 8 slide switches numbered from 0 to 7, for TGC and three rotary dial potentiometers numbered 8 to 10.

In a preferred embodiment, a trackball is a stand-alone unit which communicates with the host system via a PS/2 interface. The trackball does not go through the USB interface.

In a preferred embodiment, light emitting diodes (LEDs) are provided on the console and can be individually addressed to turn on or off. A preferred embodiment has 8 LEDs, numbered from 0 to 7, and the LEDs are located at the buttons #0 to 7 respectively.

A preferred embodiment includes a software interface protocol from the console to a host system. When a button is pressed or a potentiometer position is changed, a three byte message is sent from the console to the host. Tables 1 and 2 illustrate, respectively, the 5 message sent by using a button and a potentiometer in accordance with a preferred embodiment of the present invention.

TABLE 1

Button Message

| | Bit 7 | 6 | 5 | 4 | 3 | 2 | 1 | 0 |
|---|---|---|---|---|---|---|---|---|
| Byte #0 | 1 | 1 | 1 | 1 | 1 | 1 | 1 | 1 |
| Byte #1 | 0 | | | Button number | | | | |
| Byte #2 | X | X | X | X | X | X | X | X |

TABLE 2

Potentiometer Message

| | Bit 7 | 6 | 5 | 4 | 3 | 2 | 1 | 0 |
|---|---|---|---|---|---|---|---|---|
| Byte #0 | 1 | 1 | 1 | 1 | 1 | 1 | 1 | 1 |
| Byte #1 | 0 | | | Potentiometer number | | | | |
| Byte #2 | | | | Potentiometer position value | | | | |

The host may send a "Query" command to the console, and the console responds by sending Potentiometer Messages for every potentiometer on the console in accordance with a preferred embodiment of the present invention. Messages can be sent back-to-back in a preferred embodiment.

A preferred embodiment also includes a software interface protocol from a host system to a console. The host can send messages to the console to turn LEDs on/off, or to query the current readings of every potentiometer. Tables 3, 4 and 5 provide the LED-On message, LED-Off message and a query message, respectively, in accordance with a preferred embodiment of the present invention.

TABLE 3

LED-ON Message

| | Bit 7 | 6 | 5 | 4 | 3 | 2 | 1 | 0 |
|---|---|---|---|---|---|---|---|---|
| Byte #0 | 1 | 1 | 1 | 1 | 1 | 1 | 1 | 1 |
| Byte #1 | 0 | 0 | 0 | 0 | 0 | 0 | 0 | 1 |
| Byte #2 | 0 | | | LED number | | | | |

TABLE 4

LED-OFF Message

| | Bit 7 | 6 | 5 | 4 | 3 | 2 | 1 | 0 |
|---|---|---|---|---|---|---|---|---|
| Byte #0 | 1 | 1 | 1 | 1 | 1 | 1 | 1 | 1 |
| Byte #1 | 0 | 0 | 0 | 0 | 0 | 0 | 1 | 0 |
| Byte #2 | 0 | | | LED number | | | | |

TABLE 5

Query Message

| | Bit 7 | 6 | 5 | 4 | 3 | 2 | 1 | 0 |
|---|---|---|---|---|---|---|---|---|
| Byte #0 | 1 | 1 | 1 | 1 | 1 | 1 | 1 | 1 |
| Byte #1 | 1 | 0 | 0 | 0 | 0 | 0 | 0 | 0 |
| Byte #2 | 0 | X | X | X | X | X | X | X |

FIG. 30 illustrates the USB console for remote key pad in accordance with a preferred embodiment of the present invention. It is a hardware user interface and allows any ultrasound imaging control function to be accessed via a "traditional" control key pad. The control keys include, trackball with right and left enter keys, dedicated Freeze/live key, dedicated Save key, 8 Slide potentiometers each with a lateral movement to control the TGC gain, dedicated overall B-mode gain control pot, dedicated overall Color Flow Imaging gain control potentiometer, dedicated overall Pulsed Wave Spectral Doppler gain control pot, dedicated B-mode selection key, dedicated Power Doppler-mode selection key, dedicated Color Flowing Imaging-mode selection key, dedicated Pulsed Wave Spectral Doppler selection key, dedicated M-mode selection key, and dedicated Triplex selection key.

An LED is provided on each mode selection key. Once a mode is selected by a user, the selected mode-control key lights up.

The basic module system of the present invention is an external peripheral 16, 26 to a personal computer as shown generally in FIGS. 1-3 or a basic system configuration of the system pairs it with an off-the-shelf notebook computer with a Firewire® port. An important advantage of this configuration is that the system gets its power from the notebook computer via the single Firewire® cable. No additional power supply is needed. The combination of the peripheral 16, 26 and the notebook computer can both run on the battery of the computer, making the system very portable.

The modular system can be structured as a transformable system: a fully portable ultrasound system consisting of the ultrasound module and a notebook computer in a single portable suitcase, and which can be converted into a full feature cart system for stationary use.

The suitcase configuration shown in FIGS. 31A-31F integrates the ultrasound module and the notebook computer into a single suitcase package. An off-the-shelf consumer notebook computer 1004 with control panel or keyboard 1008 and display 1006 is secured to the suitcase using a low cost molded bracket shaped 1005 for the particular notebook model. Alternate notebook computer models can be used with a different molded bracket.

Figure 31A:
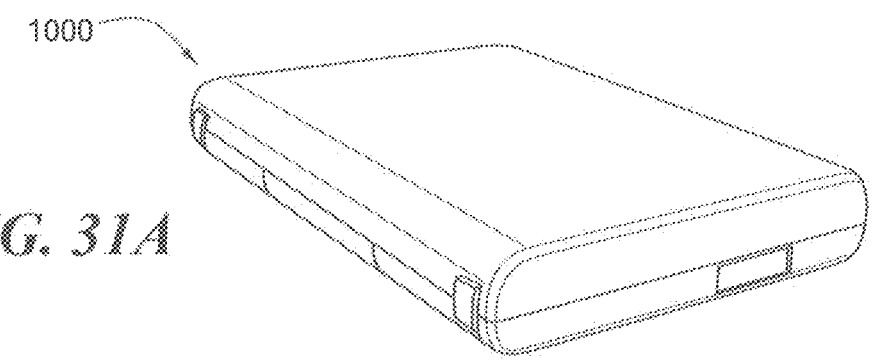
Figure 31B:
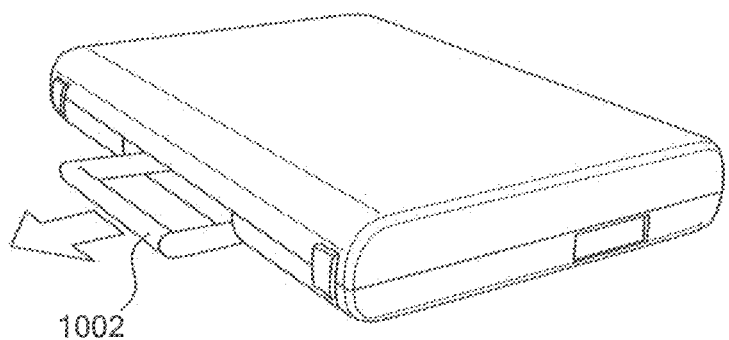
Figure 31C:
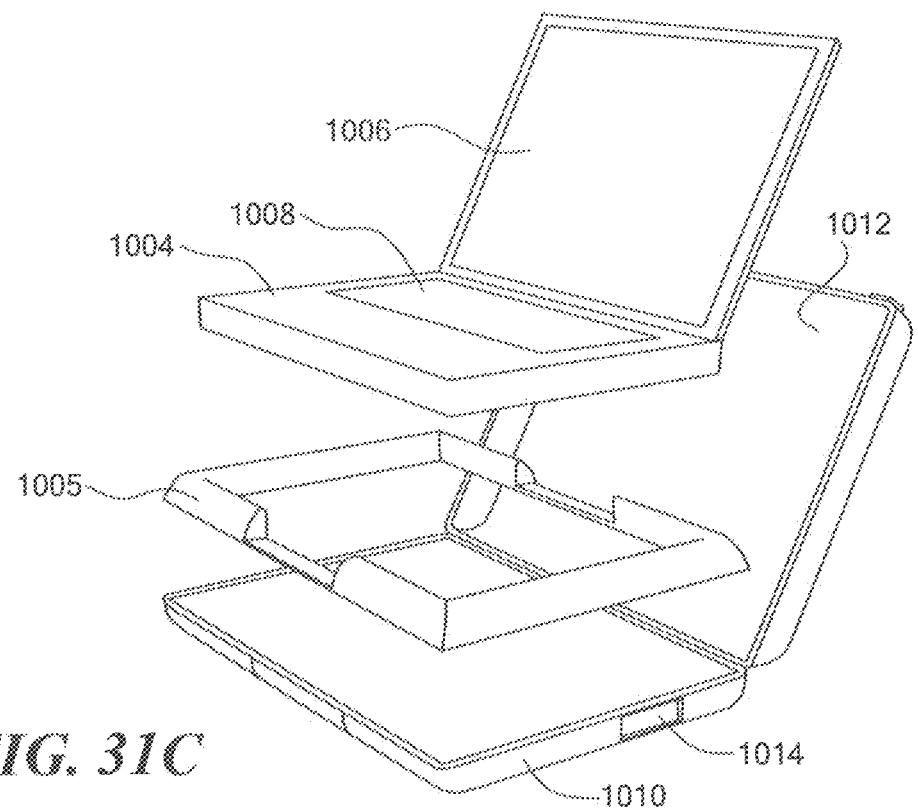
Figure 31D:
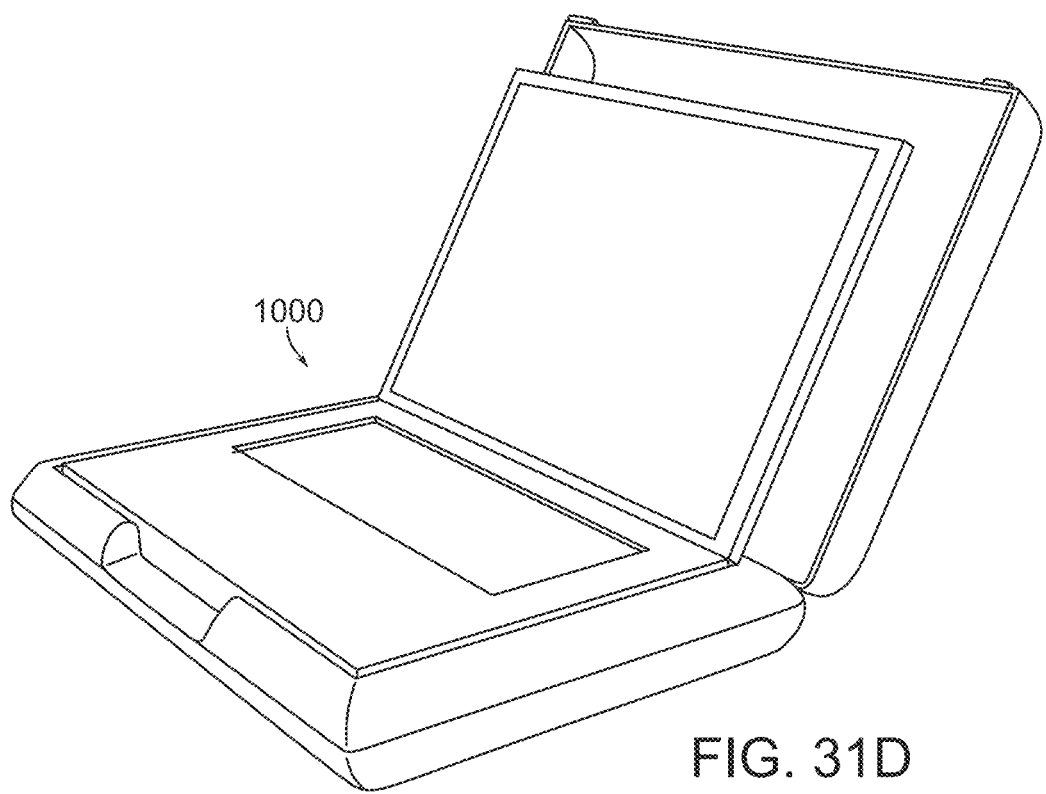
Figure 31F:
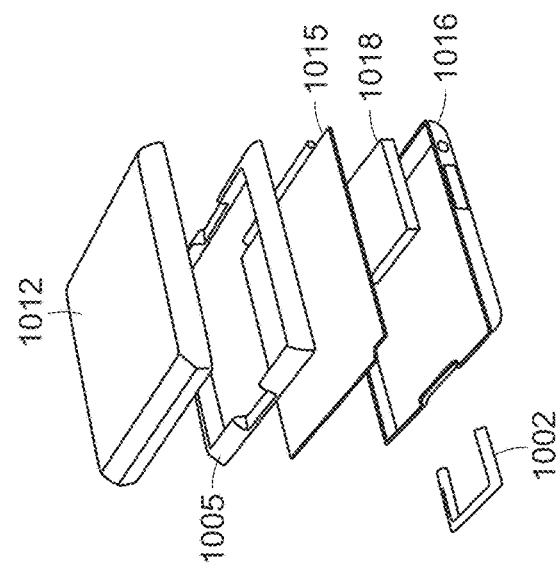
Figure 32B:
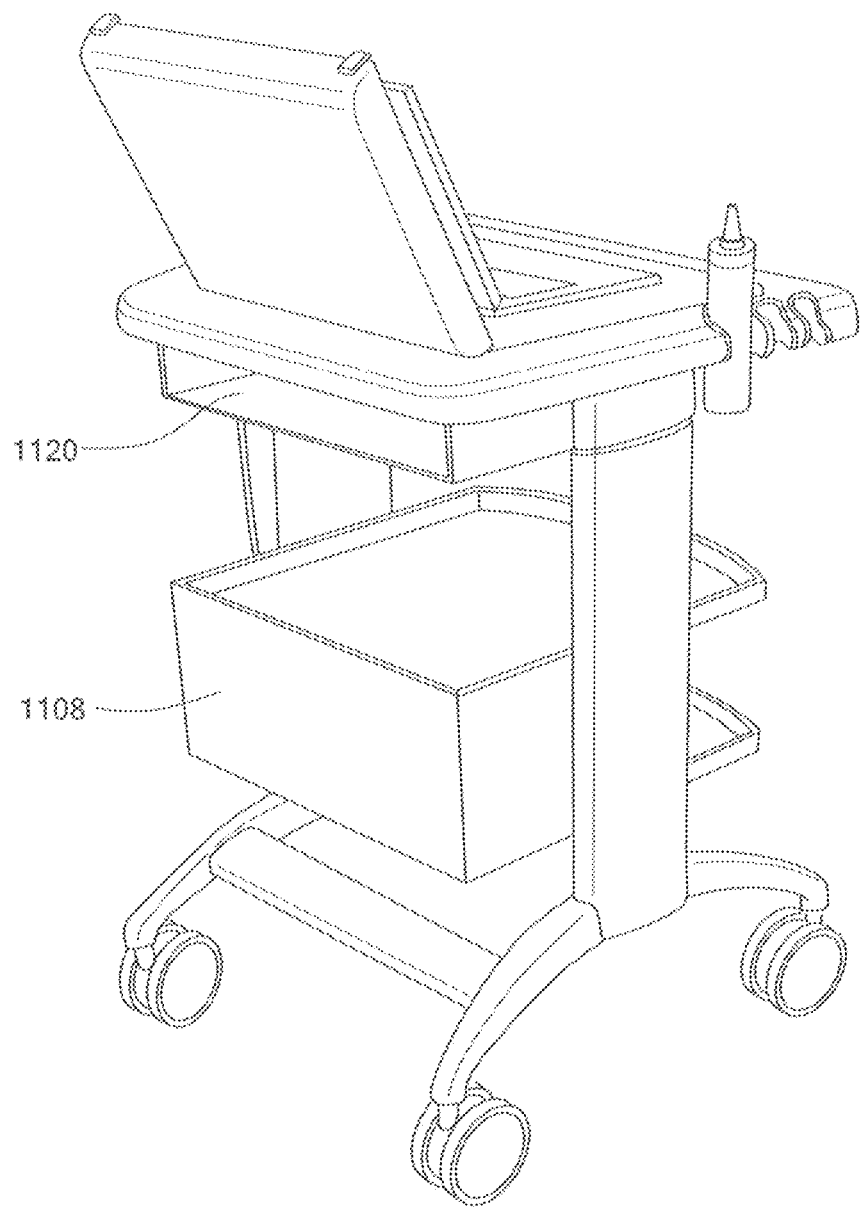
Figure 32C:
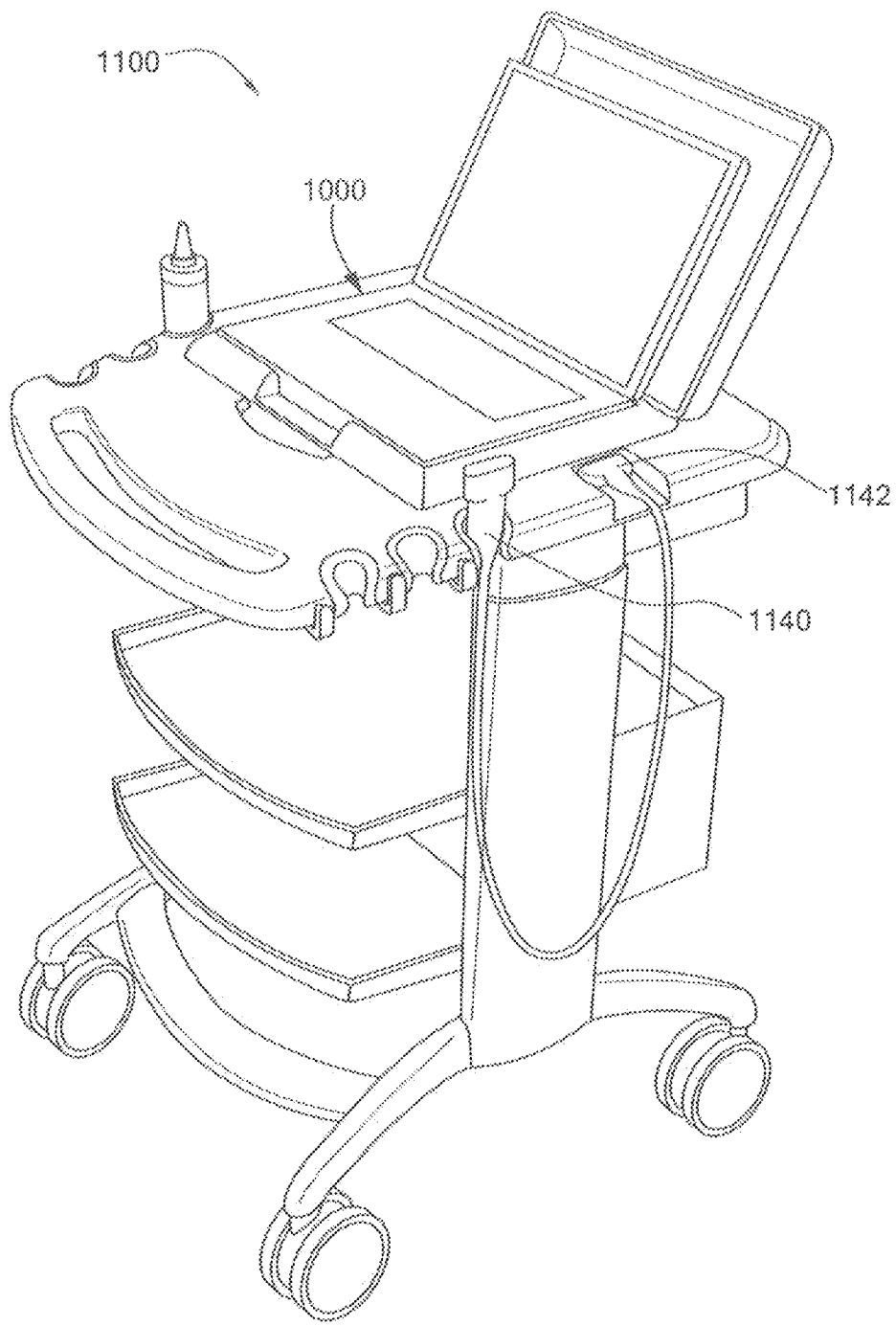
Figure 32D:
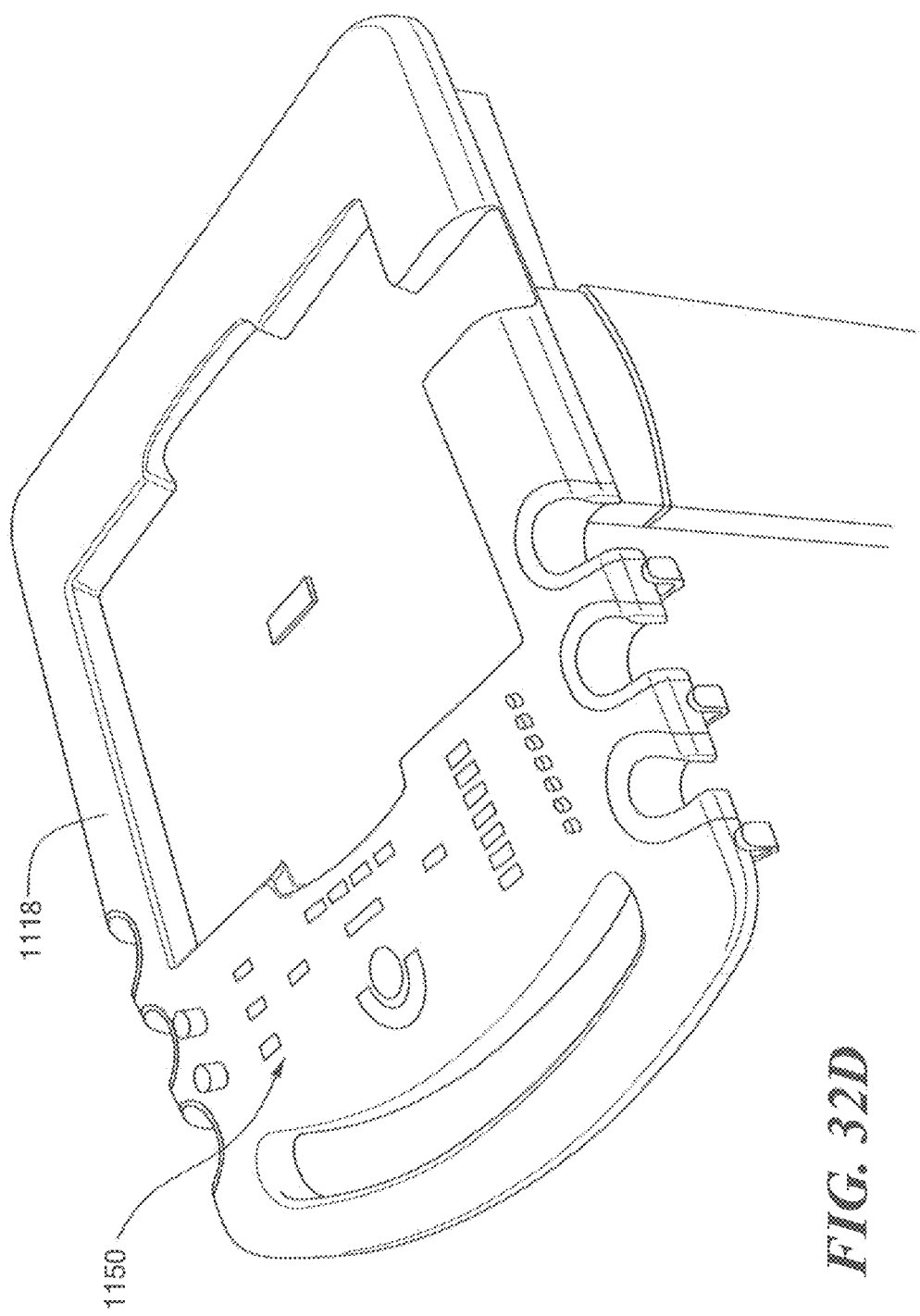
Figure 33:
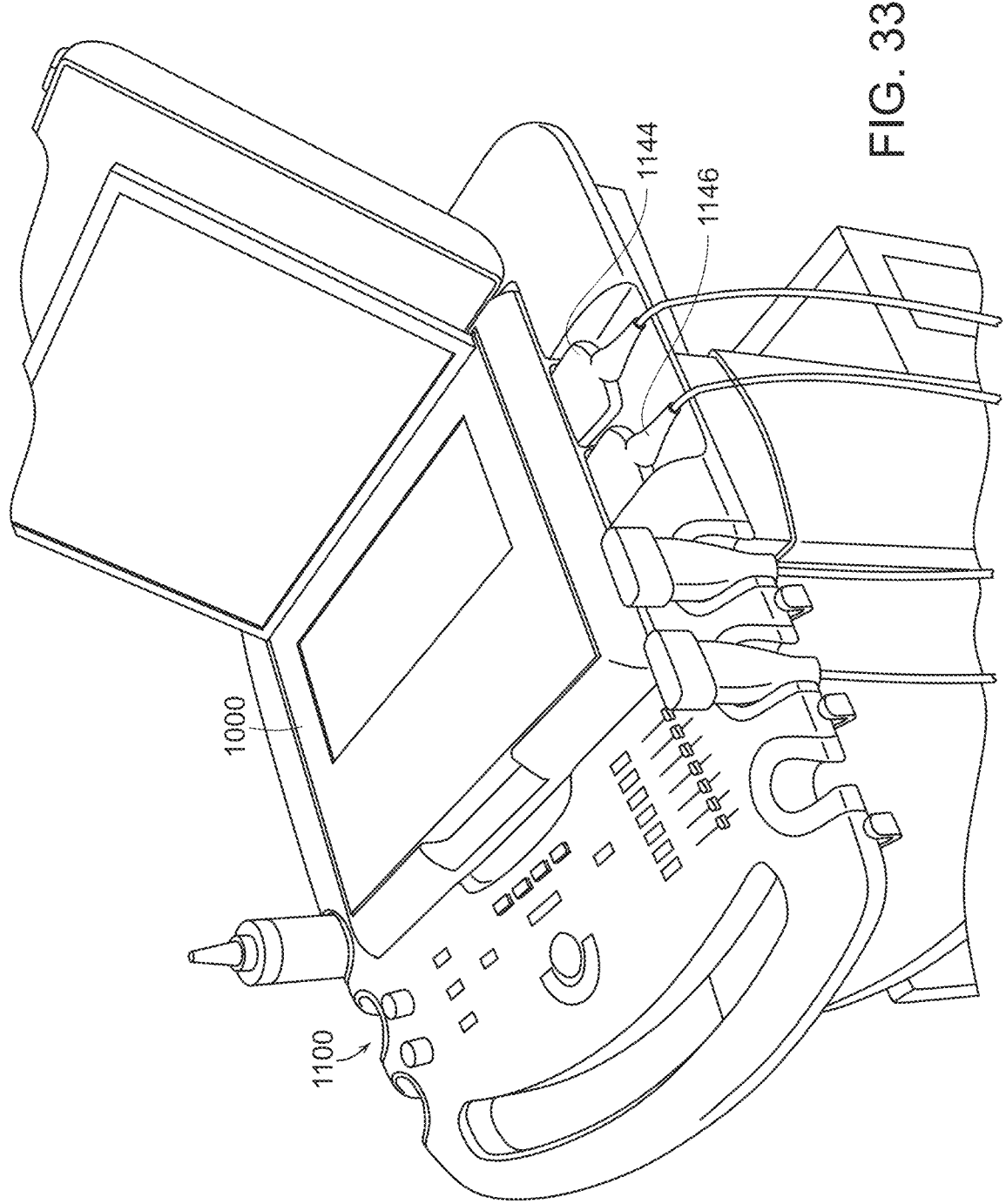
FIG. 33 illustrates a modular cart system having a plurality of transducer connectors.

As seen in FIG. 31F, the ultrasound module 1018 is situated in the base 1016 and base cover 1015 and top 1012. A handle 1002 can be extended from the housing base 1010 so that a user can carry the system with one hand. The system can be connected to, or dock with a console of a cart system seen in FIGS. 32A-32E this embodiment of the invention utilizes a mobile cart system for use in connection with a portable ultrasound imaging system.

The cart system 1100 uses a base assembly 1108 and a USB hub 1220. The base assembly can be connected to a docking bay 1222 that receives the processor housing 1000. A preferred embodiment of the docking bay system provides electrical interface connections between the base assembly and the processor Housing at docking connector 1205. The base assembly can further include a control panel 1150 such that the user can control certain operations of the ultrasound system using control elements on the control panel 1150.

The cart configuration docks the suitcase module 1000 to a cart 1100 with a full operator console 1118. Once docked, the cart and the suitcase together forms a full feature roll-about system that may have other peripherals added, such as printers and video recorders. The docking mechanism is a simple, cable-less mating connection, very much like the desk top docking station for a notebook computer. This easy docking scheme allows the user to quickly attach or detach the suitcase to convert the system between stationary use (cart), and portable use.

The user console 1118 on the cart is designed with a USB interface. The electronics on the console gets its power from the USB bus, eliminating the need of additional power source. The user console is attached to the notebook computer via the USB port of the notebook computer, routed through the docking connector of the suitcase.

An alternate design of the user console 1118 duplicates the cart base console design in a smaller portable console with the same USB interface. This portable console can be 5 plugged into the suitcase without the cart.

With a USB powered console, the cart system can operate solely on notebook computer battery without the need for being connected to the wall AC power outlet, or, when the cart system is running on wall AC power, it can continue to operate during power outage.

Figure 34:
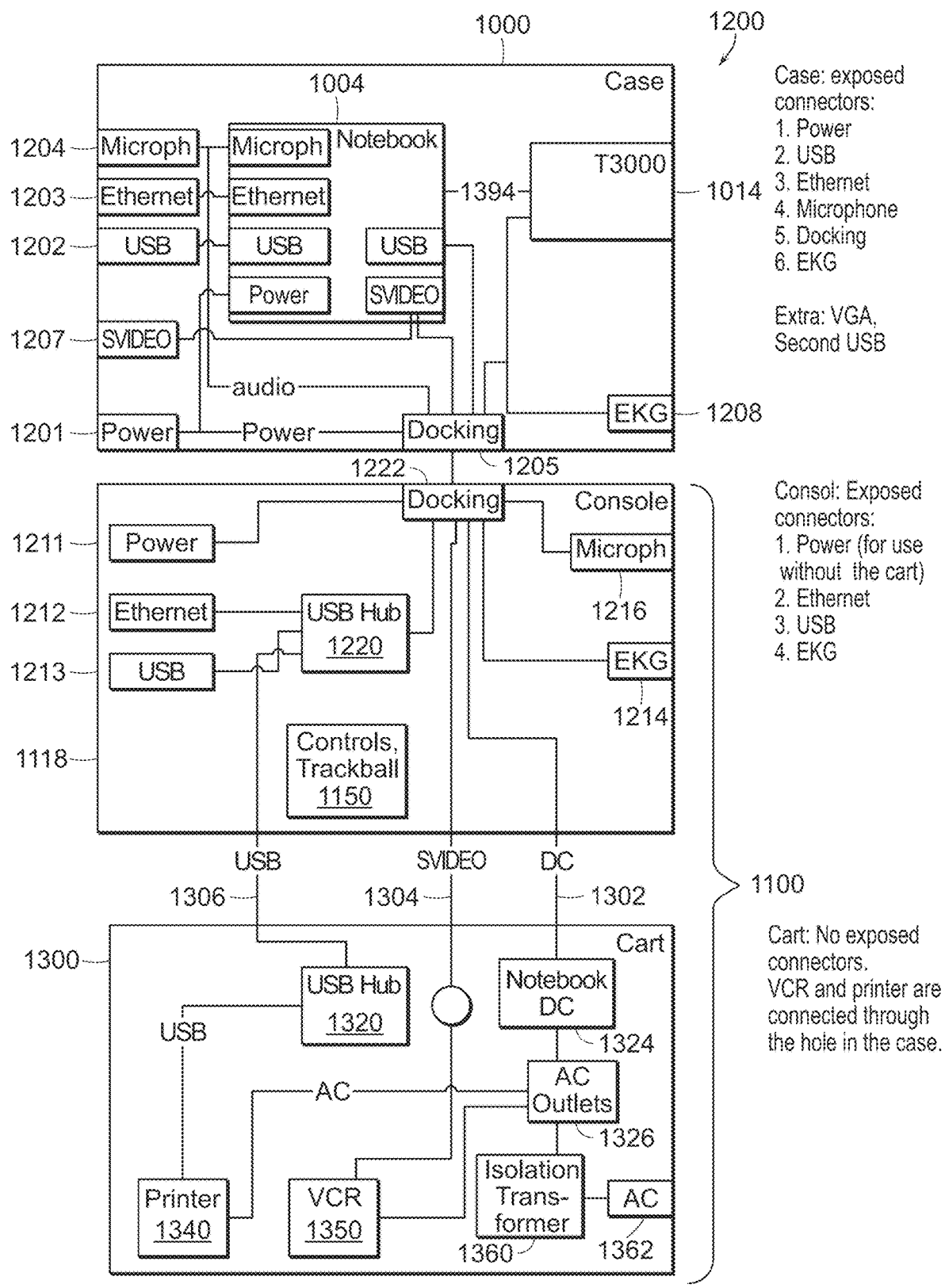
FIG. 34 is a schematic circuit diagram of a modular cart system in accordance with a preferred embodiment of the invention.

The cart system duplicates many of the notebook computer peripheral ports so that the cart system has as much features as a full blown computer, such as network connection and printer ports. As shown in FIG. 34, the cart system includes a portable system 1000 with computer 1004, a power connector 1201, USB connector 1202, ethernet connector 1203, microphone connector 1204, docking connector 1205, EKG connector 1208, and transducer connector 1014. The cart system further includes a cart 1100 having a cart assembly 1300 and a console 1118. The cart assembly 1300 includes a USB hub 1320, a printer 1340, a VCR 1350, an isolation transformer 1360, an AC outlet 1326 and a notebook DC source 1324. The console 1118 includes a power connector 1211, an ethernet connector 1212, a VSB connector 1213, a USB hub 1220, a control trackball 1150, a microphone connector 1218 and an EUG connector 1214.

In view of the wide variety of embodiments to which the principles of the present invention can be applied, it should be understood that the illustrated embodiments are exemplary only, and should not be taken as limiting the scope of the present invention. For example, the steps of the flow diagrams may be taken in sequences other than those described, and more or fewer elements may be used in the block diagrams. While various elements of the preferred embodiments have been described as being implemented in software, other embodiments in hardware or firmware implementations may alternatively be used, and vice-versa.

It will be apparent to those of ordinary skill in the art that methods involved in the system and method for determining and controlling contamination may be embodied in a computer program product that includes a computer usable medium. For example, such a computer usable medium can include a readable memory device, such as, a hard drive device, a CD-ROM, a DVD-ROM, or a computer diskette, having computer readable program code segments stored thereon. The computer readable medium can also include a communications or transmission medium, such as, a bus or a communications link, either optical, wired, or wireless having program code segments carried thereon as digital or analog data signals.

The claims should not be read as limited to the described order or elements unless stated to that effect. Therefore, all embodiments that come within the scope and spirit of the following claims and equivalents thereto are claimed as the invention.

The invention claimed is:

1. An ultrasound imaging system including a mobile cart for a portable ultrasound display and processing device, the ultrasound imaging system comprising:
a handheld display and image processor housing having a first electrical connector;
a computer within the handheld display and image processor housing, the computer configured to operate an ultrasound application program including a transducer identification program segment that detects an attached transducer assembly;
a touch screen graphical user interface operable on the display and image processor housing, a display being mounted within the handheld display and image processor housing over the computer such that a user can view and operate the display;
a virtual control panel to actuate an ultrasound imaging operation using the display within the handheld display and image processor housing;
a beamformer connected to receive image signals from a transducer connector during an imaging procedure;
a memory and a battery within the handheld display and image processor housing;
a base assembly having a second electrical connector configured to electrically connect to the handheld display and image processor housing that can be detachably mounted onto the base assembly such that the handheld display and image processor housing is powered by the battery, the second electrical connector being connected to an external network connection and wherein the base assembly supports a control panel that separately operates the handheld display and image processor housing;
a plurality of transducer connection ports such that a plurality of transducers electrically connect to the ultrasound imaging system, the computer being configured to identify a selected transducer and to adjust system operation based on automatically set transducer parameters for the selected transducer wherein a user selects an anatomic structure for imaging to adjust the automatically set transducer parameters; and
a cart on which the base assembly is mounted, the cart including a wheel assembly.

2. The system of claim 1, further comprising a cable-less interface configured to mate the handheld display and image processor housing to the cart.

3. The system of claim 1, further comprising a plurality of control elements coupled to the cart configured to activate the display of image data on the display being mounted within the handheld display and image processor housing.

4. The system of claim 1, further comprising an operator console coupled to the cart.

5. The system of claim 1, further comprising a control panel configured to receive a user command to control a plurality of control panel elements.

6. The system of claim 1, wherein the cart further comprises a plurality of control elements to actuate the display.

7. The system of claim 1, wherein the display further comprises a finger actuated touchscreen having a minimum display resolution of 1024×768.

8. The system of claim 1, further comprising a modular computer circuit board.

9. The system of claim 1, wherein the transducer connector further comprises a modular transducer connector.

10. The system of claim 1, further comprising a transducer array within a transducer probe that is connected to the transducer connector with a cable.

11. The system of claim 1, wherein the computer further comprises a processor configured to identify a transducer upon being connected to one of the plurality of transducer connector ports.

12. The system of claim 1, wherein the computer further comprises a processor configured to display data on the display.

13. The system of claim 1 further comprising a processor configured to receive data from a plurality of selectable transducers during an ultrasound procedure.

14. The system of claim 1, wherein the control panel further comprises a keypad coupled to the base assembly to actuate an ultrasound imaging operation using the handheld display and image processor housing.

15. The system of claim 1, further comprising a switch to select between the plurality of transducer connectors.

16. The system of claim 1, further comprising a transducer connector having at least a 160 pin socket.

17. The system of claim 1, further comprising a transducer connector having a latching mechanism.

18. The system of claim 1, further comprising a transducer connection circuit having a one wire identification chip.

19. The system of claim 1, further comprising a transducer connector having a single wire connection.

20. The system of claim 1, further comprising a transducer connector configured for bidirectional transfer of data in series between the transducer connector and the handheld display and image processor housing.

21. The system of claim 1, further comprising a battery module for powering an electronic circuit.

22. The system of claim 1, further comprising a battery module wherein a maximum operational power is 12 watts.

23. The system of claim 1, further comprising a multiplexor for selecting a transducer for an imaging procedure.

24. The system of claim 1 wherein the handheld display and processor housing comprises a notebook computer.

25. The system of claim 1 wherein the computer adjusts beamformer operating parameters based on the transducer identification.

26. A handheld medical ultrasound imaging device comprising:
a plurality of handheld transducer assemblies, each transducer assembly including a probe housing, a transducer array, and a cable with a first transducer connector; and
a handheld portable processing unit connectable to each of the handheld transducer assemblies with the cable and the first transducer connector at one or more connectors on the processing unit, the processing unit having an integrated touch screen display that displays an ultrasound image wherein the integrated touch screen display is mounted integral with a processor operative in response to the integrated touch screen display, a memory system, a battery, and an ultrasound beamformer processing circuit wherein the integrated touch screen display and the ultrasound beamformer processing circuit are communicably connected to the processor, the processor being operative in response to finger operation of the integrated touch screen display to operate a graphical user interface that displays a type for an attached transducer assembly and one or more corresponding automatically set imaging parameters, upon connection of the first transducer connector and selection of an anatomic structure to be imaged, on the integrated touch screen display, wherein the portable processing unit further comprises a plurality of computer programs including a scan conversion program, a Doppler processing program and a transducer identification program segment that detects the attached transducer assembly.

27. The handheld medical ultrasound imaging device of claim 26 wherein each transducer assembly further comprises a probe identification circuit that stores probe calibration information.

28. The handheld medical ultrasound imaging device of claim 27 wherein the probe identification circuit further comprises a programmable, writable and readable memory to store calibration information.

29. The handheld medical ultrasound imaging device of claim 26 wherein the handheld portable processing unit has a processor circuit board, a digital circuit board and an analog circuit board that are vertically stacked below the display; and
the handheld portable processing unit has a universal serial bus (USB) port and/or an Ethernet port.

30. The handheld medical ultrasound imaging device of claim 26 wherein the handheld portable processing unit further comprises a system controller connected to the beamformer processing circuit wherein the processing unit further comprises transmit/receive integrated circuits with at least 32 transducer channels; and the processing unit is operable without any controls other than power on/off.

31. The handheld medical ultrasound imaging device of claim 26 wherein the processing unit further comprises buttons adjacent the display, and the processing unit operates at 12 Watts at maximum power and wherein the processing unit is connectable to a keyboard.

32. The handheld medical ultrasound imaging device of claim 26 wherein the transducer array is connected to a transmit and receive circuit which is connected to a digital control circuit and the beamformer processing circuit; and
a first transducer has at least 160 pins with a pin pitch of 1 mm or less or has at least 250 pins with a pin pitch of 0.8 mm or less.

33. The handheld medical ultrasound imaging device of claim 26 wherein a plurality of different transducer assemblies having different operating frequencies and/or geometries can be attached to the processing unit, the processing unit having a plurality of transducer connectors; and
further comprising a transducer connector mechanism including a movable lever.

34. The handheld medical ultrasound imaging device of claim 26 further comprising a handle and a stand.

35. The handheld medical ultrasound imaging device of claim 26 wherein the display is a 10 inch display or wherein the display is a 12 inch display; and
the display has a minimum brightness of 200 Nits for viewing the touchscreen display.

36. The handheld medical ultrasound imaging device of claim 26 wherein the processor is mounted in the portable processing unit with the display, the processor configured to adjust the automatically set imaging parameters using different histograms corresponding to different selectable anatomic structures.

37. The handheld medical ultrasound imaging device of claim 26 further comprising a needle guide device and wherein the processing unit is configured with software instructions to perform a needle guide procedure.

38. The handheld medical ultrasound imaging device of claim 26 further comprising a probe identification circuit in each transducer assembly, the probe identification circuit including a readable, writeable memory, and further including a single wire identification circuit, wherein the probe identification circuit stores usage data, identification data and calibration data, the usage data including dates of use of the transducer assembly.

39. The handheld medical ultrasound imaging device of claim 26, further comprising a base assembly that receives the handheld portable processing unit, the handheld portable processing unit having a first docking connector that electrically connects to a second docking connector on the base assembly, the base assembly further comprising a cart, the cart further includes a power connector.

40. The handheld medical ultrasound imaging device of claim 39, further comprising a control console on the base assembly which is operationally connected to the processor and has a plurality of control elements configured to control an image processing operation of the processor to display ultrasound image data on the display.

41. A handheld medical ultrasound imaging device comprising:
at least one handheld transducer assembly to perform an imaging operation wherein the at least one transducer assembly includes a probe housing, a transducer array, and a cable with a first transducer connector; and
a handheld portable processing unit connectable to the at least one handheld transducer assembly with the cable and the first transducer connector at a processing unit connector, the processing unit having an integrated touch screen display that displays an ultrasound image wherein the integrated touch screen display is mounted integral with a processor operative in response to the integrated touch screen display, a memory system, a battery, the processor configured to communicate with an ultrasound beamformer processing circuit, the processor being operative in response to finger operation of the integrated touch screen display to operate a graphical user interface that displays one or more automatically set imaging parameters of the at least one transducer assembly upon connection of the first transducer connector to the processing unit connector and selection of an anatomical structure to be imaged, wherein the processor is configured to operate a plurality of computer programs including a scan conversion program, a Doppler processing program, an automatically set image parameter module and a transducer identification program segment that detects an attached transducer assembly.

42. The handheld medical ultrasound imaging device of claim 41 wherein each transducer assembly further comprises a probe identification circuit that stores probe calibration information.

43. The handheld medical ultrasound imaging device of claim 41 wherein the probe identification circuit further comprises a programmable, writable and readable memory to store calibration information.

44. The handheld medical ultrasound imaging device of claim 41 wherein the handheld portable processing unit has a processor circuit board, a digital circuit board and an analog circuit board that are vertically stacked below the display; and
the handheld portable processing unit has a universal serial bus (USB) port and/or an Ethernet port.

45. The handheld medical ultrasound imaging device of claim 41 wherein the handheld portable processing unit further comprises a system controller connected to the beamformer processing circuit wherein the processing unit further comprises transmit/receive integrated circuits with at least 32 transducer channels; and the processing unit is operable without any controls other than power on/off.

46. The handheld medical ultrasound imaging device of claim 41 wherein the processing unit further comprises buttons adjacent the display, and the processing unit operates at 12 Watts at maximum power and wherein the processing unit is connectable to a keyboard.

47. The handheld medical ultrasound imaging device of claim 41 wherein the transducer array is connected to a transmit and receive circuit which is connected to a digital control circuit and the beamformer processing circuit; and
a first transducer has at least 160 pins with a pin pitch of 1 mm or less or has at least 250 pins with a pin pitch of 0.8 mm or less.

48. The handheld medical ultrasound imaging device of claim 41 wherein a plurality of different transducer assemblies having different operating frequencies can each be attached to the processing unit, the processing unit having a plurality of transducer connectors; and
further comprising a transducer connector mechanism including a movable lever.

49. The handheld medical ultrasound imaging device of claim 41 further comprising a handle and a stand.

50. The handheld medical ultrasound imaging device of claim 41 wherein the display is a 10 inch display or wherein the display is a 12 inch display; and
the display has a minimum brightness of 200 Nits for viewing the touchscreen display.

51. The handheld medical ultrasound imaging device of claim 41 wherein the processor comprises a single board computer; and the processor processes Doppler image data that is displayed on the display.

52. The handheld medical ultrasound imaging device of claim 41 wherein the processing unit is configured with software instructions to perform a needle guide procedure.

53. The handheld medical ultrasound imaging device of claim 41 further comprising a probe identification circuit in each transducer assembly, the probe identification circuit including a readable, writeable memory, and further including a single wire identification circuit, wherein the probe identification circuit stores usage data, identification data and calibration data, the usage data including dates of use of the transducer assembly.

54. The handheld medical ultrasound imaging device of claim 41, wherein the at least one handheld transducer assembly further comprises the ultrasound beamformer processing circuit.

55. The handheld medical ultrasound imaging device of claim 41, wherein the automatically set imaging parameters for different anatomical structures comprise different histograms.

* * * * *